United States Patent
Kao et al.

(12) United States Patent (10) Patent No.: US 7,635,560 B2
Kao et al. (45) Date of Patent: Dec. 22, 2009

(54) PYGOPUS IN DIAGNOSIS AND TREATMENT OF CANCER

(75) Inventors: Kenneth Kao, St. John's (CA); Catherine Popadiuk, St. John's (CA)

(73) Assignee: Genesis Group Inc., St. John's, Newfoundland (CA)

( * ) Notice: Subject to any disclaimer, the term of this patent is extended or adjusted under 35 U.S.C. 154(b) by 0 days.

(21) Appl. No.: 10/553,661

(22) PCT Filed: Apr. 16, 2004

(86) PCT No.: PCT/CA2004/000571

§ 371 (c)(1),
(2), (4) Date: Oct. 17, 2005

(87) PCT Pub. No.: WO2004/092407

PCT Pub. Date: Oct. 28, 2004

(65) Prior Publication Data

US 2006/0275330 A1 Dec. 7, 2006

Related U.S. Application Data

(60) Provisional application No. 60/463,309, filed on Apr. 17, 2003, provisional application No. 60/496,012, filed on Aug. 19, 2003.

(51) Int. Cl.
*C12Q 1/68* (2006.01)
*G01N 33/53* (2006.01)
(52) U.S. Cl. .......................... 435/6; 435/7.1
(58) Field of Classification Search ................. None
See application file for complete search history.

(56) References Cited

U.S. PATENT DOCUMENTS

| | | | |
|---|---|---|---|
| 4,806,463 A | 2/1989 | Goodchild et al. | |
| 5,004,810 A | 4/1991 | Draper | |
| 5,087,617 A | 2/1992 | Smith | |
| 5,098,890 A | 3/1992 | Gewirtz et al. | |
| 5,135,917 A | 8/1992 | Burch | |
| 5,166,195 A | 11/1992 | Ecker | |
| 5,194,428 A | 3/1993 | Agrawal et al. | |
| 5,264,423 A | 11/1993 | Cohen et al. | |
| 5,276,019 A | 1/1994 | Cohen et al. | |
| 5,286,717 A | 2/1994 | Cohen et al. | |
| 5,366,866 A | 11/1994 | Xu et al. | |
| 5,474,796 A * | 12/1995 | Brennan ................... 427/2.13 | |
| 5,484,704 A | 1/1996 | Dunbar | |
| 5,645,995 A | 7/1997 | Kieback | |
| 5,871,941 A | 2/1999 | Auersperg | |
| 5,932,435 A | 8/1999 | Atkins et al. | |
| 6,048,528 A | 4/2000 | Dunbar | |
| 6,072,034 A | 6/2000 | Kaufman et al. | |
| 6,277,563 B1 | 8/2001 | Shayesteh et al. | |
| 6,300,492 B1 | 10/2001 | Korneluk et al. | |
| 6,350,615 B1 | 2/2002 | Kaufman et al. | |
| 6,376,654 B1 | 4/2002 | Gelber | |
| 6,468,546 B1 | 10/2002 | Mitcham et al. | |
| 6,468,758 B1 | 10/2002 | Benson et al. | |
| 6,475,732 B1 | 11/2002 | Shayesteh et al. | |
| 6,488,931 B1 | 12/2002 | Mitcham et al. | |
| 6,512,102 B1 | 1/2003 | Xu et al. | |
| 6,943,241 B2 * | 9/2005 | Isogai et al. ................ 536/23.1 |
| 2001/0016651 A1 * | 8/2001 | Kennedy .................. 536/24.31 |

OTHER PUBLICATIONS

Thompson et al (Nature Cell Biol. 4: 367-373, 2002).*
McShane, L.M., Altman, D.G., Sauerbrei, W., Taube, S.E., Gion, M., Clark, G.M., for the statistics subcommittee of the NCI-EORTC working group on cancer diagnostics. REporting recommendations for tumor MARKer prognostic studies (REMARK). 2005. European Journal of Cancer. vol. 41, pp. 1690-1696.*
Andrews, P.G.P., Lake, B.B., Popadiuk, C., and Kao, K.R. Requirement of Pygopus 2 in breast cancer. 2007. International Journal of Oncology. vol. 30 No. 2, pp. 357-363.*
Aasland R, Gibson TJ and Stewart AF. (1995). *Trends Biochem Sci,* 20, 56-59.
Aksan, I. & Stinson, J. A. (2002) *Trends Biochem. Sci.* 27, 387-389.
Amit, S. et al. Axin-mediated CKI phosphorylation of beta-catenin at Ser 45: a molecular switch for the Wnt pathway. *Genes Dev.* 16, 1066-1076 (2002).
Baker BF, Condon TP, Koller E, McKay RA, Siwkowski AM, Vickers TA and Monia BP. (2001). *Methods,* 23, 191-198.
Belenkaya, T.Y. et al. pygopus Encodes a nuclear protein essential for wingless/Wnt signaling. *Development* 129, 4089-4101 (2002).
Bienz and Clevers. Cell 103: 311-320. Oct. 13, 2000.
Brown AM. (2001). *Breast Cancer Res,* 3, 351-355.
Cadigan, K. M. (2002) *Trends Genet.* 18, 340-342.
Chou, Y.Y. et al. Differentiation of ovarian mucinous carcinoma and metastatic colorectal adenocarcinoma by immunostaining with beta-catenin. *Histopathology* 43, 151-156 (2003).
Clevers H. (2002). *Mol Cell,* 10, 1260-1261.
Cliffe, A., Hamada, F. & Bienz, M. (2003) *Curr. Biol.* 13, 960-966.
Coqueret O. (2002). *Gene,* 299, 35-55.
Davies, B. R., Worsley, S. D. & Ponder, B. A. (1998) *Histopathology* 32, 69-80.
Delcommenne M, Tan C, Gray V, Rue L, Woodgett J and Dedhar S. (1998). *Proc Natl Acad Sci U S A,* 95, 11211-11216.
Dhar, K. K., Branigan, K., Parkes, J., Howells, R. E., Hand, P., Musgrove, C., Strange, R. C., Fryer, A. A., Redman, C. W. & Hoban, P. R. (1999) *Br. J. Cancer* 81, 1174-1181.
Doble, B. W. & Woodgett, J. R. (2003) *J. Cell Sci.* 116, 1175-1186.
Fanto, M. & McNeill, H. Planar polarity from flies to vertebrates. *J. Cell Sci.* 117, 527-533 (2004).

(Continued)

*Primary Examiner*—David J. Blanchard
*Assistant Examiner*—Anne M. Gussow

(57) ABSTRACT

Expression of pygopus mRNA and Pygopus protein in established cancer cell lines and in patient tumors is described. Pygopus is shown to be a feasible diagnostic and prognostic indicator. Pygopus is also useful in cancer treatment therapy, for example in disrupting strategies that specifically target the activity of pygopus in cancer cells.

20 Claims, 22 Drawing Sheets

OTHER PUBLICATIONS

Furuuchi K, Tada M, Yamada H, Kataoka A, Furuuchi N, Hamada J, Takahashi M, Todo S and Moriuchi T. (2000). *Am J Pathol*, 156, 1997-2005.

Gao, Z.H., Seeling,J.M., Hill,V., Yochum,A., & Virshup,D.M. Casein kinase I phosphorylates and destabilizes the beta-catenin degradation complex. *Proc. Natl. Acad. Sci. U.S.A.* 99, 1182-1187 (2002).

Giles RH, van Es JH and Clevers H. (2003). *Biochim Biophys Acta*, 1653, 1-24.

Greaves. Nature Cell Biol. 4:E124. May 2002.

Green DW, Roh H, Pippin J and Drebin JA. (2000). *J Am Coll Surg*, 191, 93-105.

He TC, Sparks AB, Rago C, Hermeking H, Zawel L, da Costa LT, Morin PJ, Vogelstein B and Kinzler KW. (1998). *Science*, 281, 1509-1512.

Henderson, B.R. Nuclear-cytoplasmic shuttling of APC regulates beta-catenin subcellular localization and turnover. *Nat. Cell Biol.* 2, 653-660 (2000).

Holnthoner W, Pillinger M, Groger M, Wolff K, Ashton AW, Albanese C, Neumeister P, Pestell RG and Petzelbauer P. (2002). *J Biol Chem*, 277, 45847-45853.

Howe LR and Brown AM. (2004). *Cancer Biol Ther*, 3: 36-41.

Huelsken, J. & Behrens, J. The Wnt signalling pathway. *J. Cell Sci.* 115, 3977-3978 (2002).

http://www2.mrc-lmb.cam.ac.uk/research/CB/Bienz.M/BienzM.html [2 page print-out], 2006.

Ju ST, Panka DJ, Cui H, Ettinger R, el Khatib M, Sherr DH, Stanger BZ and Marshak-Rothstein A. (1995). *Nature*, 373, 444-448.

Kikuchi, A. (2003) *Cancer Sci.* 94, 225-229.

Kishida S, Yamamoto H, Hino S, Ikeda S, Kishida M and Kikuchi A. (1999). *Mol Cell Biol*, 19, 4414-4422.

Kishida, S. et al. Axin, a negative regulator of the wnt signaling pathway, directly interacts with adenomatous polyposis coli and regulates the stabilization of beta-catenin. *J. Biol. Chem.* 273, 10823-10826 (1998).

Klingensmith J, Nusse R and Perrimon N. (1994). *Genes Dev*, 8, 118-130.

Korinek et al. Science 275: 1784-1787. 1997.

Kramps, T. et al. Wnt/wingless signaling requires BCL9/legless-mediated recruitment of pygopus to the nuclear beta-catenin-TCF complex. *Cell* 109, 47-60 (2002).

Kuhl, M. The WNT/Calcium pathway: biochemical mediators, tools and future requirements. *Front Biosci.* 9, 967-974 (2004).

Kuhnert, F. et al. Essential requirement for Wnt signaling in proliferation of adult small intestine and colon revealed by adenoviral expression of Dickkopf-1. *Proc. Natl. Acad. Sci. U.S.A.*. 101, 266-271 (2004).

Lake BB and Kao KR. (2003). *Dev Biol*, 261, 132-148.

Lake et al. Development. 128(2): 263-273. Jan. 2001 (Abstract).

Lepourcelet, M., Chen, Y. N., France, D. S., Wang, H., Crews, P., Petersen, F., Bruseo, C., Wood, A. W. & Shivdasani, R. A. (2004) *Cancer Cell* 5, 91-102.

Li, Y. et al. Evidence that transgenes encoding components of the Wnt signaling pathway preferentially induce mammary cancers from progenitor cells. *Proc. Natl. Acad. Sci. U. S. A* 100, 15853-15858 (2003).

Li, H., Pamukcu, R. & Thompson, W. J. (2002) *Cancer Biol. Ther.* 1, 621-625.

Lim SC and Lee MS. (2002). *Oncol Rep*, 9, 915-928.

Lin SY, Xia W, Wang JC, Kwong KY, Spohn B, Wen Y, Pestell RG and Hung MC. (2000). *Proc Natl Acad Sci U S A*, 97, 4262-4266.

Lustig B and Behrens J. (2003). *J Cancer Res Clin Oncol*, 129, 199-221.

Miller, J.R., Hocking,A.M., Brown,J.D., & Moon,R.T. Mechanism and function of signal transduction by the Wnt/beta-catenin and Wnt/Ca2+ pathways. *Oncogene* 18, 7860-7872 (1999).

Moon, R.T., Bowerman,B., Boutros,M., & Perrimon,N. The promise and perils of Wnt signaling through beta-catenin. *Science* 296, 1644-1646 (2002).

Muratovska A, Zhou C, He S, Goodyer P and Eccles MR. (2003). *Oncogene*, 22, 7989-7997.

Nagahata T, Shimada T, Harada A, Nagai H, Onda M, Yokoyama S, Shiba T, Jin E, Kawanami O and Emi M. (2003). *Cancer Sci*, 94, 515-518.

NCBI Sequence Accession No. AY141128 Lake and Kao. Oct. 21, 2002.

NCBI Sequence Accession No. AY141129 Lake and Kao. Oct, 21, 2002.

NCBI Sequence Accession No. AF521655 Belenkaya et al. Aug. 14, 2002.

NCBI Sequence Accession No. AAM94597 Belenkaya et al. Aug. 14, 2002.

Nusse R and Varmus HE. (1982). *Cell*, 31, 99-109.

Orsulic, S., Huber,O., Aberle,H., Arnold,S., & Kemler,R. E-cadherin binding prevents beta-catenin nuclear localization and beta-catenin/LEF-1-mediated transactivation. *J. Cell Sci.* 112 ( Pt 8), 1237-1245 (1999).

Palacios, J. & Gamallo, C. (1998) *Cancer Res.* 58, 1344-1347.

Parker, D.S., Jemison, J., & Cadigan, K.M. Pygopus, a nuclear PHD-finger protein required for Wingless signaling in Drosophila. *Development* 129, 2565-2576 (2002).

Polakis P. (2000). *Genes Dev*, 14, 1837-1851.

Polesskaya, A., Seale,P., & Rudnicki,M.A. Wnt signaling induces the myogenic specification of resident CD45+ adult stem cells during muscle regeneration. *Cell* 113, 841-852 (2003).

Qin C, Burghardt R, Smith R, Wormke M, Stewart J and Safe S. (2003). *Cancer Res*, 63, 958-964.

Rask, K. et al. Wnt-signalling pathway in ovarian epithelial tumours: increased expression of beta-catenin and GSK3beta. *Br. J. Cancer* 89, 1298-1304 (2003).

Reynolds, J.N., Prasad,A., Gillespie,L.L., & Paterno,G.D. Developmental expression of functional GABAA receptors containing the gamma 2 subunit in neurons derived from embryonal carcinoma (P19) cells. *Brain Res. Mol. Brain Res.* 35, 11-18 (1996).

Rorke, S., Murphy,S., Khalifa,M., Chernenko,G., & Tang,S.C. Prognostic significance of BAG-1 expression in nonsmall cell lung cancer. *Int. J. Cancer* 95, 317-322 (2001).

Ryan PJ and Gillespie LL. (1994). *Dev Biol*, 166, 101-111.

Ryo A, Nakamura M, Wulf G, Liou YC and Lu KP. (2001). *Nat Cell Biol*, 3, 793-801.

Scholten,A.N., Creutzberg,C.L., van den Broek,L.J., Noordijk,E.M., & Smit,V.T. Nuclear beta-catenin is a molecular feature of type I endometrial carcinoma. *J. Pathol.* 201, 460-465 (2003).

Schwartz,D.R. et al. Novel candidate targets of beta-catenin/T-cell factor signaling identified by gene expression profiling of ovarian endometrioid adenocarcinomas. *Cancer Res.* 63, 2913-2922 (2003).

Seidman,J.D. & Kurman,R.J. Pathology of ovarian carcinoma. *Hematol. Oncol. Clin. North Am.* 17, 909-25, vii (2003).

Sekiya T, Nakamura T, Kazuki Y, Oshimura M, Kohu K, Tago K, Ohwada S and Akiyama T. (2002). *Cancer Res*, 62, 3322-3326.

Shibamoto S, Hayakawa M, Takeuchi K, Hori T, Oku N, Miyazawa K, Kitamura N, Takeichi M and Ito F. (1994). *Cell Adhes Commun*, 1, 295-305.

Shtutman M, Zhurinsky J, Simcha I, Albanese C, D'Amico M, Pestell R and Ben Ze'ev A. (1999). *Proc Natl Acad Sci U S A*, 96, 5522-5527.

Smalley MJ and Dale TC. (2001). *J Mammary Gland Biol Neoplasia*, 6, 37-52.

Taipale J and Beachy PA. (2001). *Nature*, 411, 349-354.

Tamai K, Semenov M, Kato Y, Spokony R, Liu C, Katsuyama Y, Hess F, Saint-Jeannet JP and He X. (2000). *Nature*, 407, 530-535.

Tetsu O and McCormick F. (1999). *Nature*, 398, 422-426.

Thompson B, Townsley F, Rosin-Arbesfeld R, Musisi H and Bienz M. (2002). *Nat Cell Biol*, 4, 367-373.

Thompson BJ. (2004). *Curr Biol*, 14, 458-466.

Townsley FM, Thompson B and Bienz M. (2004). *J Biol Chem*, 279, 5177-5183.

Townsley FM, Cliffe A and Bienz M. (2004). *Nat Cell Biol*, 6, 626-633.

Tsutsumi K, Belaguli N, Qi S, Michalak TI, Gulliver WP, Pater A and Pater MM. (1992). *Am J Pathol*, 140, 255-261.

van De WM, Barker N, Harkes IC, van der HM, Dijk NJ, Hollestelle A, Klijn JG, Clevers H and Schutte M. (2001). *Cancer Res*, 61, 278-284.

van De WM, Cavallo R, Dooijes D, van Beest M, van Es J, Loureiro J, Ypma A, Hursh D, Jones T, Bejsovec A, Peifer M, Mortin M and Clevers H. (1997). *Cell*, 88, 789-799.

Verma,U.N., Surabhi,R.M., Schmaltieg,A., Becerra,C., & Gaynor,R.B. Small interfering RNAs directed against beta-catenin inhibit the in vitro and in vivo growth of colon cancer cells. *Clin. Cancer Res.* 9, 1291-1300 (2003).

Watts CK, Sweeney KJ, Warlters A, Musgrove EA and Sutherland RL. (1994). *Breast Cancer Res Treat*, 31, 95-105.

Webster MT, Rozycka M, Sara E, Davis E, Smalley M, Young N, Dale TC and Wooster R. (2000). *Genes Chromosomes Cancer*, 28, 443-453.

Wehrli M, Dougan ST, Caldwell K, O'Keefe L, Schwartz S, Vaizel-Ohayon D, Schejter E, Tomlinson A and DiNardo S. (2000). *Nature*, 407, 527-530.

Wheelock, M.J. & Johnson,K.R. Cadherins as modulators of cellular phenotype. *Annu. Rev. Cell Dev. Biol.* 19, 207-235 (2003).

Wheelock MJ and Knudsen KA. (1991). In Vivo, 5, 505-513.

Wiggan,O. & Hamel,P.A. Pax3 regulates morphogenetic cell behavior in vitro coincident with activation of a PCP/non-canonical Wnt-signaling cascade. *J. Cell Sci.* 115, 531-541 (2002).

Willert,K., Shibamoto,S., & Nusse,R. Wnt-induced dephosphorylation of axin releases beta-catenin from the axin complex. *Genes Dev.* 13, 1768-1773 (1999).

Willis TG, Zalcberg IR, Coignet LJ, Wlodarska I, Stul M, Jadayel DM, Bastard C, Treleaven JG, Catovsky D, Silva ML and Dyer MJ. (1998). *Blood*, 91, 1873-1881.

Wissmann C, Wild PJ, Kaiser S, Roepcke S, Stoehr R, Woenckhaus M, Kristiansen G, Hsieh JC, Hofstaedter F, Hartmann A, Knuechel R, Rosenthal A and Pilarsky C. (2003). *J Pathol*, 201, 204-212.

Wong,A.S. & Auersperg,N. Ovarian surface epithelium: family history and early events in ovarian cancer. *Reprod. Biol. Endocrinol.* 1, 70 (2003).

Yam CH, Fung TK and Poon RY. (2002). *Cell Mol Life Sci*, 59, 1317-1326.

Yanagawa S, van Leeuwen F, Wodarz A, Klingensmith J and Nusse R. (1995). *Genes Dev*, 9, 1087-1097.

Yin F, Wakino S, Liu Z, Kim S, Hsueh WA, Collins AR, Van Herle AJ and Law RE. (2001). *Biochem Biophys Res Commun*, 286, 916-922.

Zhai,Y. et al. Role of beta-catenin/T-cell factor-regulated genes in ovarian endometrioid adenocarcinomas. *Am. J. Pathol.* 160, 1229-1238 (2002).

Zhurinsky, J., Shtutman, M. & Ben Ze'ev, A. (2000) *J Cell Sci.* 113 ( Pt 18), 3127-3139.

* cited by examiner

Amino Acid Sequence of hPygo2

MAASAPPPPDKLEGGGGPAPPPAPPSTGRKQGKA<u>GLQMKSPEKK</u>
<u>RRK</u>SNTQGPAYSHLTEFAPPPTPMVDHLVASNPFEDDFGAPKVG
VAAPPFLGSPVPFGGFRVQGGMAGQVPPGYSTGGGGGPQPLRRQ
PPPFPPNPMGPAFNMPPQGPGYPPPGNMNFPSQPFNQPLGQNFS
PPSGQMMPGPVGGFGPMISPTMGQPPRAELGPPSLSQRFAQPGA
PFGPSPLQRPGQGLPSLPPNTSPFPGPDPGFPGPGGEDGGKPLN
PPASTAFPQEPHSGSPAAAVNGNQPSFPPNSSGRGGGTPDANSL
APPGKAGGGSGPQPPPGLVY<u>PCGACRSEVNDDQDAILCEASCQK</u>
<u>WFHRECTGMTESAYGLLTTEASAVWACDLCLKT</u>KEIQSVYIREGM
GQLVAANDG

FIG. 1

ALIGNMENT OF HPYGO1 VS HPYGO2

VERSION BLASTP 2.2.6

Sequence 1 gi 19550449 pygopus 1 [Homo sapiens] Length 419 (1 .. 419)
Sequence 2 gi 21594198 Pygopus 2 [Homo sapiens] Length 406 (1 .. 406)

Score = 240 bits (613)

Identities = 161/439 (36%)
Positives  = 214/439 (48%)
Gaps       = 58/439 (13%)

```
Pygo1:   3  AENSPAPAYKVSSHGGDSGLDG-------LGGPGVQLGSPDKKKRKANTQGPSFPPLSEY   55
            A ++P P K+    GG +           G G+Q+ SP+KK+RK+NTQGP++ L+E+
Pygo2:   2  AASAPPPPPDKLEGGGGPAPPPAPPSTGRKQGKAGLQMKSPEKKRRKSNTQGPAYSHLTEF  61

Pygo1:  56  APPPNPNSDHLVAANPFDDNYNTISYKPLPSSNPYLGPGYPGFGGYSTFR-MPPHVPPRM  114
            APPP P  DHLVA+NPF+D++    + K   ++ P+LG  P FGG+    M   VPP
Pygo2:  62  APPPTPMVDHLVASNPFEDDFG--APKVGVAAPPFLGSPVP-FGGFRVQGGMAGQVPPGY  118

Pygo1: 115  SSPYCG-PYSLRNQPHPFPQNPLGMGFNRP-HAFNFGPHDNSSFGNPSYNNALSQNVNMP  172
            S+    G P  LR QP PFP NP+G  FN P       + P N +F +  +N L QN + P
Pygo2: 119  STGGGGGPQPLRRQPPPFPPNPMGPAFNMPPQGPGYPPPGNMNFPSQPFNQPLGQNFSPP  178

Pygo1: 173  NQHFRQNPAENFSQI-------PPQNASQVSNPDLASNFVPGNNSNFTSPLESNHSFIP-  224
            +     P  F +         PP+  +++  P L+  F          SPL+    +P
Pygo2: 179  SGQMMPGPVGGFGPMISPTMGQPPR--AELGPPSLSQRFAQPGAPFGPSPLQRPGQGLPS  236

Pygo1: 225  -PPNTFGQAKAPPPKQDFTQGATKNTNQNSSAHPPHLNMDDTVNQSNIELKNVNRNNAVN  283
             PPNT    +P P   D    +        +PP             + A
Pygo2: 237  LPPNT-----SPFPGPDPGFPGPGGEDGGKPLNPP-----------------ASTAFP   272

Pygo1: 284  QENSRSSSTEATNNNPANGTQNKPRQPRGAADACTTEKSNKSSLHPNRHGHSSSDP----  339
            QE   S    A NN +  N +   G DA +    K+        G S    P
Pygo2: 273  QEPHSGSPAAAVNGNQPSFPPNSSGRGGGTPDANSLAPPGKAG------GGSGPQPPPGL  326

Pygo1: 340  VYPCGICTNEVNDDQDAILCEASCQKWFHRICTGMTETAYGLLTAEASAVWGCDTCMADK  399
            VYPCG C +EVNDDQDAILCEASCQKWFHR CTGMTE+AYGLLT EASAVW CD C+  K
Pygo2: 327  VYPCGACRSEVNDDQDAILCEASCQKWFHRECTGMTESAYGLLTTEASAVWACDLCLKTK  386
```

PHD-finger.
PHD folds into an i>
330    ****************************************************

```
Pygo1: 400  DVQLMRTRETFGPSAVGSD  418
            ++Q +  RE G      +D
Pygo2: 387  EIQSVYIREGMGQLVAAND  405
```

FIG. 2

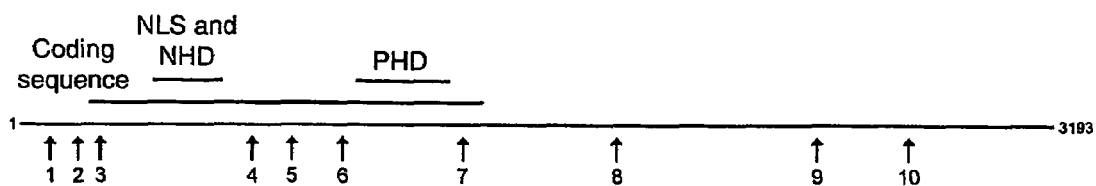
FIG. 3G
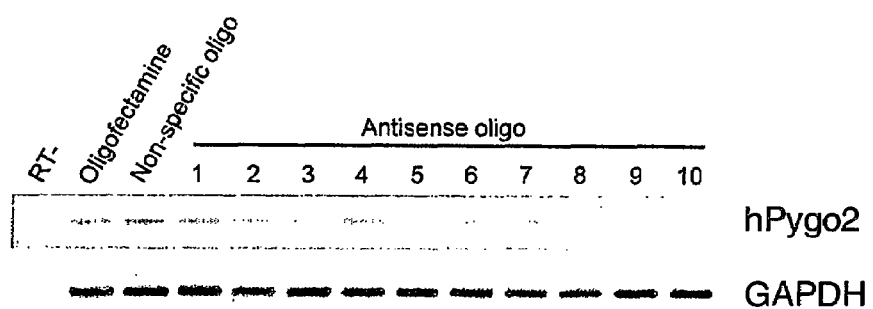
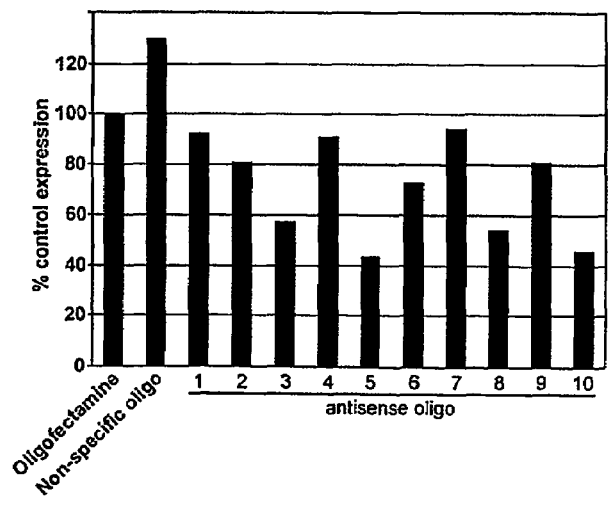
FIG. 3H

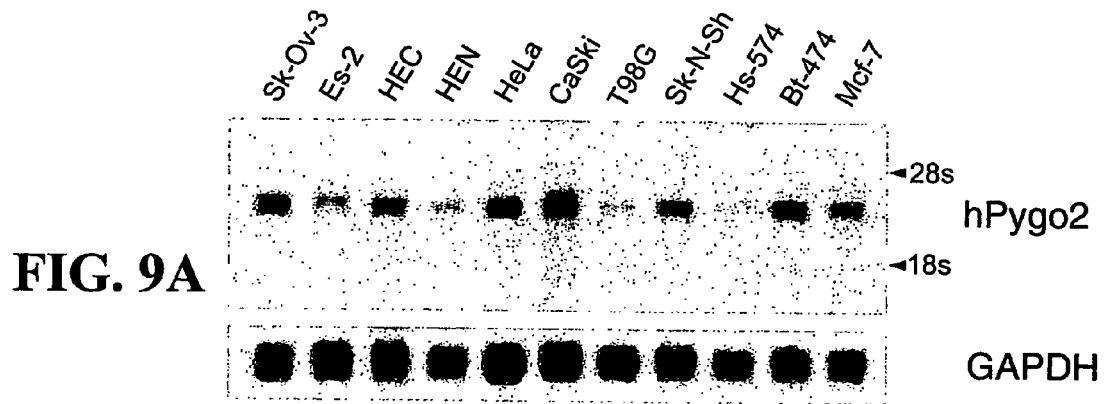
FIG. 9A
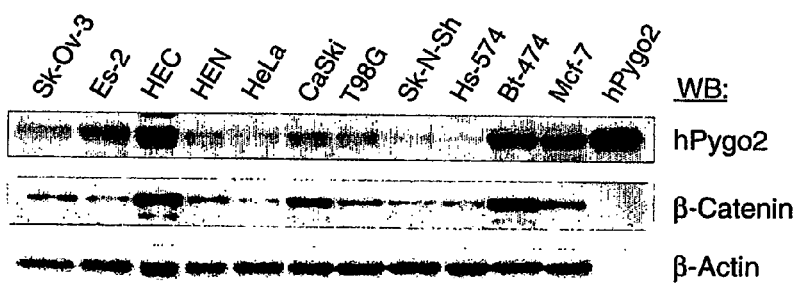
FIG. 9B
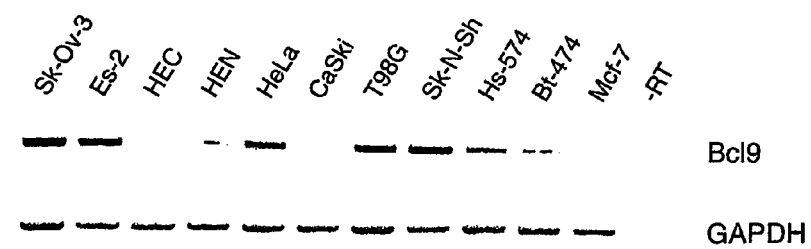
FIG. 9C
FIG. 9D

PYGOPUS IN DIAGNOSIS AND TREATMENT OF CANCER

REFERENCE TO RELATED APPLICATIONS

This application claims the benefit of U.S. Provisional Application No. 60/463,309, filed Apr. 17, 2003, and U.S. Provisional Application No. 60/496,012, filed Aug. 19, 2003, the contents of which are herein incorporated by reference.

FIELD OF INVENTION

The present invention relates to the Pygopus gene and its use in the diagnosis and treatment of cancer.

BACKGROUND OF THE INVENTION

Reliable markers for malignant tumor differentiation are necessary for accurate diagnosis of cancer. In addition, many of these markers may prove useful as targets for therapy, especially if they are required for growth or metastasis of cancer cells. Present therapies for cancer include surgery, radiation and chemotherapy. For the most part, chemotherapy involves the use of general DNA synthesis inhibitors, DNA structure disruptors and DNA adducts in which chemical agents are added to the primary DNA molecule. The problem with these approaches is that they are not specific to cancer cells, so there are many serious negative side effects associated with chemotherapy such as nausea, hair loss, gastrointestinal disorders and disruption of normal brain function.

The Wnt-signaling pathway has been known for some time to be abnormally activated in colon cancer. Pygopus is a downstream effector of this pathway. The problem we faced was to determine how to use human Pygopus in cancer diagnostic and therapy.

The canonical Wnt/β-catenin pathway is normally required for embryonic development and for the controlled proliferation of adult stem cells. The critical mediator of the pathway is β-catenin, a multifunctional protein whose activity depends on its cytoplasmic localization. In the absence of Wnt signaling, the majority of β-catenin is associated with the plasma membrane, where it is required with E-cadherin for cell adhesion. Cytoplasmic levels of free β-catenin are regulated by a destruction complex consisting of tumor suppressor proteins that include Glycogen Synthase Kinase-3 beta (GSK-3β), Axin, Adenomatous Polyposis Coli (APC) and Casein Kinase I which cooperatively direct cytoplasmic β-catenin for proteosome-mediated degradation. The binding of Wnt to its receptor relieves degradation of cytosolic β-catenin, allowing it to accumulate in the nucleus where it assembles into a complex that binds to genes involved in cell cycle progression. This complex is composed of Leukemia Enhancer/T-cell Factor (LEF)/TCF-1, B-cell lymphoma-9 protein (BCL-9) and the nuclear protein, Pygopus. Localized chromatin remodeling effects by Pygopus, specifically bound to BCL-9 are thought to allow access of the basal transcriptional machinery to initiate target gene transcription.

SUMMARY OF THE INVENTION

We describe here the expression of pygopus mRNA and Pygopus protein in established cancer cell lines and in patient tumors to assess its role as a diagnostic and prognostic indicator, as well as disrupting strategies that specifically target the activity of pygopus to determine its role in cancer.

Rational drug design utilizes emerging technologies that target cellular processes uniquely adopted by cancer cells for their survival. Study of the function of genes required for early embryonic development, for instance, is a focal point in biomedical research because developmentally important genes also have a role in cancer. Understandably, controlled embryonic cellular activities such as proliferation and invasion/migration are activities necessary for cancer cell survival. Conversely, many cancers result because of the abnormal activation of cellular processes and functions that were once used in the embryo but are no longer necessary for, and indeed are detrimental to adult cell function.

We have determined, using molecular analyses and antisense RNA techniques, that human Pygopus is a nuclear protein required for cell proliferation of human malignant tumors. This functional data is supported by expression analyses using both nucleic acid probes and Pygopus specific antibodies, which demonstrate that Pygopus is consistently and highly overexpressed in highly malignant cancer cells including those of ovarian, breast, colon and uterine cervix. Unlike any other protein, Pygopus is a novel, generalized marker and factor required for cancer cell survival. Therefore, non-expressing embryonic cells and non-expressing adult cells are insensitive to attempts which deplete Pygopus' function. As such, Pygopus can be used for diagnostic purposes and as a specific pharmacological target to fight a wide range of cancers.

The Pygopus protein has two distinctive domains, a 50 amino acid stretch within the N-terminus referred to as the N-terminal homology domain (NHD) or N box and the C-terminal plant homeodomain (PHD). PHD motifs (also known as leukemia associated protein, or LAP, domains) are zinc finger-like domains of the concensus Cys4-His-Cys3 that are present within a number of chromatin remodeling-type transcriptional regulators (FIG. 1).

The NHD of pygopus is the domain that activates Wnt signalling. This domain comprises the N box (about 47 residues), and may extend to the N-terminal half of pygopus. For example, the NHD of human pygopus may comprise up to about amino acids 1-232. The NHD domain may be used without the endogenous nuclear localization signal (NLS), or the endogenous NLS may be replaced with a heterologous NLS. Thus in one embodiment, the NHD comprises at least about 47 amino acids in the N-terminal half of pygopus, and retains the ability to activate Wnt signalling.

Pygopus and Pygopus-derived peptide and nucleic acid sequences may be used as a therapeutic (eg chemo, hormonal, etc.) target for cancer. Antibodies and other molecular devices related to Pygopus may be used for detection and diagnosis of all pre-tumor and tumor cells for prognostic information. Antisense RNA, RNAi and antibodies may be used to deplete Pygopus function. Pygopus and Pygopus-derived peptide and nucleic acid sequences may be used to screen for cancer and precancer cells.

Our highly sensitive antibodies and nucleic acid probes will be used to specifically detect and differentiate cancer cells in, for instance, a pathological specimen, a surgical biopsy, or other cytological-based diagnostic procedures such as pap smears. Thus new diagnostic reagents for clinical prognostic diagnosis of cancer are provided. Such diagnostic tools may be used to accurately assess tumor grade and stage as a prognostic indicator to more effectively and economically manage cancer and pre-cancer patients.

We demonstrate that depletion of Pygopus specifically stops cancer cell growth. Thus molecules that specifically interact with and inactivate the function of Pygopus would be useful for treating cancer.

We describe a method of screening for inhibitors of pygopus activity by testing for the ability of a candidate inhibitor to bind specifically to NHD. Binding of the candidate to NHD would indicate that the candidate is a potential inhibitor of pygopus activity. That the candidate is a pygopus inhibitor may be confirmed by testing for the candidate's ability to block transcriptional activation of Wnt-responsive genes, such as Cyclin D1, by NHD. One way of testing for transcriptional activation of Wnt-responsive genes is by using the TOPFLASH system (see for example, Korinek et al 1997 Science 275:1784-1787).

We also describe antisense sequences against human pygopus, including hPygo1 (SEQ ID NOs:3 and 4) and hPygo2 (SEQ ID NOs:1 and 2). The antisense sequences may be those sequences specific to pygopus-2; i.e. antisense sequences that would bind to pygopus-2 and not to other human sequences. The antisense sequences include those which bind to the coding region of human pygopus-2, or to the non-coding regions, in particular the 3' non-coding region. The antisense sequences may be at least 10, 12, 15, 18, 20, 25, 30, 35 or 50 nucleotides long. It is noted that hPygo1 is probably functionally interchangeable with hPygo2 (Thompson, B. et al. Nat. Cell Biol. 4, 367-373 (2002)).

We also described proteins, other than full-length human pygopus, which comprise fragments of human pygopus. These fragments are useful at least as antigens to elicit an immune response and produce antibodies. The fragments include regions that are unique to human pygopus-2. The fragments may be derived from amino acids 1-45, or 74-312 of human pygopus-2. The fragments should be of sufficient size as to form a functional epitope to elicit an antibody response. An epitope may be as short as 8 to 10 amino acids.

The proteins comprising the fragments may be a fusion protein which includes a heterologous protein fused in frame to the fragment described above. The fragments, particularly short peptides of 8 to 30 amino acids, may also be crosslinked to carrier molecules for eliciting an antibody response.

We also describe antibodies, both polyclonal and monoclonal, to human pygopus. In one embodiment, the antibody binds to a fragment of human pygopus-2. Such a fragment include regions of pygopus that are unique to human pygopus-2 such as those derived from amino acids 1-45, or 74-312 of human pygopus-2. In a preferred embodiment, the antibody is of sufficient titre as to be able to bind specifically to tumor cells in situ or in vivo.

We also describe methods of making antibodies to human pygopus. The method comprises eliciting an antibody response to a fragment of human pygopus, as described above, or a fusion protein comprising a fragment of human pygopus or a fragment of human pygopus linked to a carrier molecule.

We also describe a method for determining whether a cell is a cancer cell. The method comprises assaying the cell for overexpression of pygopus. In one embodiment, the cell is a human cell. In another embodiment, the cancer is ovarian, ovarian epithelial, breast, uterine cervical, cervical, lung, or colon cancer. The cell may be assayed for pygopus mRNA overexpression, or pygopus protein overexpression.

We also describe methods and kits for diagnosis of cancer. The method and kits test for for overexpression of pygopus. In one embodiment, the cell is a human cell. In another embodiment, the cancer is ovarian, ovarian epithelial, breast, uterine cervical, cervical, lung, or colon cancer. The cell may be assayed for pygopus mRNA overexpression, or pygopus protein overexpression.

We also describe methods for attenuating growth of cancer cells that express pygopus. The method comprises depleting the cell of pygopus activity. In one embodiment, pygopus activity is depleted by means of antisense polynucleotides. In another embodiment, pygopus activity is depleted using RNA interference.

The present invention thus relates to a method for determining the presence or absence of a cancer in a patient, the method comprising the steps of: (a) determining the level of Pygopus gene expression in a biological sample obtained from a patient, and (b) comparing the level of Pygopus gene expression in the biological sample to a predetermined cut-off value, to determine whether Pygopus expression is higher in the biological sample; therefrom determining the presence or absence of cancer in the patient.

The present invention further relates to a method for monitoring the progression of a cancer in a patient, the method comprising the steps of: (a) determining the level of Pygopus gene expression in a biological sample obtained from a patient, and (b) comparing the level of Pygopus gene expression in the biological sample to a predetermined cut-off value, to determine whether Pygopus expression is higher in the biological sample; and therefrom determining the presence or absence of cancer in the patient; (c) repeating steps (a) and (b) using a biological sample obtained from the patient at a subsequent time; and (d) comparing the level of Pygopus gene expression detected in step (c) to the level of Pygopus gene expression detected in step (b); and therefrom monitoring the progression of the cancer in the patient. The predetermined cut-off value may be the level of Pygopus gene expression in a normal biological sample.

In certain embodiments, the cancer is ovarian cancer, and the biological sample is a tissue biopsy containing epithelial ovarian cells; or the cancer is breast cancer, and the biological sample is a tissue biopsy containing mammary cells.

In certain embodiments, the Pygopus gene is hPygo2 as shown in SEQ ID NO:1, or hPygo1 as shown in SEQ ID NO:3.

In certain embodiments, the level of Pygopus gene expression is determined by the amount of Pygopus protein or by the amount of Pygopus mRNA.

The present invention further relates to a kit for determining the presence or absence of a cancer in a patient, the kit comprising a reagent capable of detecting Pygopus protein or mRNA in a biological sample obtained from the patient, and instructions for using the reagent to determine whether the level of Pygopus gene expression in the biological sample is higher compared to a predetermined cut-off value, and therefrom determining the presence or absence of cancer in the patient.

In certain embodiments, the reagent is an antibody specifically reactive to Pygopus protein.

In certain embodiments, the reagent is a polynucleotide capable of binding to a Pygopus gene or to a part of a Pygopus gene.

In certain embodiments, the predetermined cut-off value is the level of Pygopus gene expression in a normal biological sample.

The present invention further relates to human Pygopus polypeptide which lacks the plant homeodomain (PHD) sequence and the N-terminal homology domain (NHD) sequence.

In certain embodiments, the polypeptide is hPygo-2 (SEQ ID NO:2) lacking amino acids 89-328 or hPygo-1 (SEQ ID NO:4) lacking amino acids 85-341.

The present invention further relates to a nucleic acid encoding the polypeptide of the invention, for example comprising nucleotides 437-1156 of SEQ ID NO:1 or nucleotides 253-1023 of SEQ ID NO:3.

The present invention further relates to an antibody specifically reactive with the polypeptide of the invention. The antibody may be a monoclonal antibody.

The present invention further relates to a method for obtaining a compound which inhibits tumor cell proliferation, wherein the tumor cell expresses Pygopus, the method comprising: (a) testing a candidate compound and selecting the compound for binding to an expressed product of a Pygopus gene; (b) testing the compound selected in (a) for its ability to inhibit Pygopus-mediated transcription activation of a Wnt-responsive gene; and optionally (c) testing the compound selected in (b) in epithelial ovarian carcinoma or breast cancer cells for its ability to inhibit proliferation of the cells.

In certain embodiments, in step (a), the candidate compound is tested and selected for binding to a Pygopus protein.

In certain embodiments, in step (a), the candidate compound is tested and selected for binding to a Pygopus mRNA.

In certain embodiments, in step (b), the candidate compound is tested for its ability to inhibit Pygopus-mediated transcription activation of Cyclin D1.

The present invention further relates to a method for obtaining an antisense polynucleotide which inhibits tumor cell proliferation, wherein the tumor cell express Pygopus, the method comprising: (a) providing a polynucleotide which is antisense to a Pygopus gene, or antisense to a portion of a Pygopus gene; (b) delivering the polynucleotide into epithelial ovarian carcinoma or breast cancer cells; and (c) determining whether the delivered polynucleotide inhibits proliferation of the cancer cells.

The present invention further relates to a method for obtaining a compound which inhibits tumor cell proliferation, wherein the tumor cell express Pygopus, the method comprising: (a) providing a short interfering RNA (siRNA) or siRNA-like molecule targeted to a Pygopus gene or to a portion of a Pygopus gene; (b) delivering the siRNA or siRNA-like molecule into epithelial ovarian carcinoma or breast cancer cells; and (c) determining whether the delivered siRNA or siRNA-like molecule inhibits proliferation of the cancer cells.

The present invention further relates to a method for inhibiting tumor cell proliferation, the method comprising contacting the tumor cell with a proliferation-inhibiting amount of a compound which reduces Pygopus activity in the cell.

In certain embodiments, the tumor cell is an epithelial ovarian carcinoma cell or breast cancer cell.

In certain embodiments, the compound reduces the ability of Pygopus to inhibit transcription activation of a Wnt-responsive gene.

In certain embodiments, the Wnt-responsive gene is Cyclin D1.

The present invention further relates to a method for inhibiting tumor cell proliferation, the method comprising delivering to the tumor cell a proliferation-inhibiting amount of a compound which reduces expression of a Pygopus-encoding nucleic acid.

In certain embodiments, the compound is a polynucleotide which is antisense to a Pygopus gene, or antisense to a portion of a Pygopus gene.

In certain embodiments, the compound is a short interfering RNA (siRNA) or siRNA-like molecule targeted to a Pygopus gene or to a portion of a Pygopus gene.

The present invention further relates to an antisense oligonucleotide targeted to hPygo2 (SEQ ID NO:1) in the region from nucleotide 437 to 1156 of SEQ ID NO:1, wherein said antisense oligonucleotide specifically hybridizes with said region and reduces the expression of hPygo2.

The present invention further relates to an antisense oligonucleotide targeted to hPygo1 (SEQ ID NO:3) in the region from nucleotide 253 to 1023 of SEQ ID NO:3, wherein said antisense oligonucleotide specifically hybridizes with said region and reduces the expression of hPygo1.

The present invention further relates to a short interfering RNA (siRNA) or siRNA-like molecule targeted to hPygo2 (SEQ ID NO:1) in the region from nucleotide 437 to 1156 of SEQ ID NO:1, wherein said siRNA or siRNA-like molecule reduces the expression of hPygo2.

The present invention further relates to a short interfering RNA (siRNA) or siRNA-like molecule targeted to hPygo1 (SEQ ID NO:3) in the region from nucleotide 253 to 1023 of SEQ ID NO:3, wherein said siRNA or siRNA-like molecule reduces the expression of hPygo1.

In certain embodiments, the antisense oligonucleotide has the sequence selected from the group consisting of SEQ ID NOS:5-14.

In certain embodiments, the siRNA or siRNA-like molecule has the sequence selected from the group consisting of SEQ ID NOS:15-19.

BRIEF DESCRIPTION OF THE DRAWINGS

FIG. 1: Amino acid sequence of human hPygo2. The putative nuclear localisation signal (KKRRK) is in bold. The C-terminal PHD is double underlined and the NHD is single underlined.

FIG. 2: Sequence alignment of human hPygo1 and hPygo2.

(d) Expression of Pygo binding partner Bcl-9. Total RNA was analyzed by RT-PCR using primers specific to Bcl-9. −RT, negative control, without reverse transcriptase.
(e) Human Pygopus protein is expressed in malignant cancer cell lines independently of Wnt-signalling factors. Total protein was extracted from eight different cell lines representing four different tumor types and processed for Western analysis using antibodies against Wnt target proteins and transducers, as well as anti-hPygo2 antibodies.
(f) Anti-hPygo2 antibodies were used for immuno-histochemical analysis of MCF-7 breast cancer cells and SK-OV-3 ovarian cancer cells. Anti-hPygo2 antibodies stain the nuclei specifically.

Figure 10:
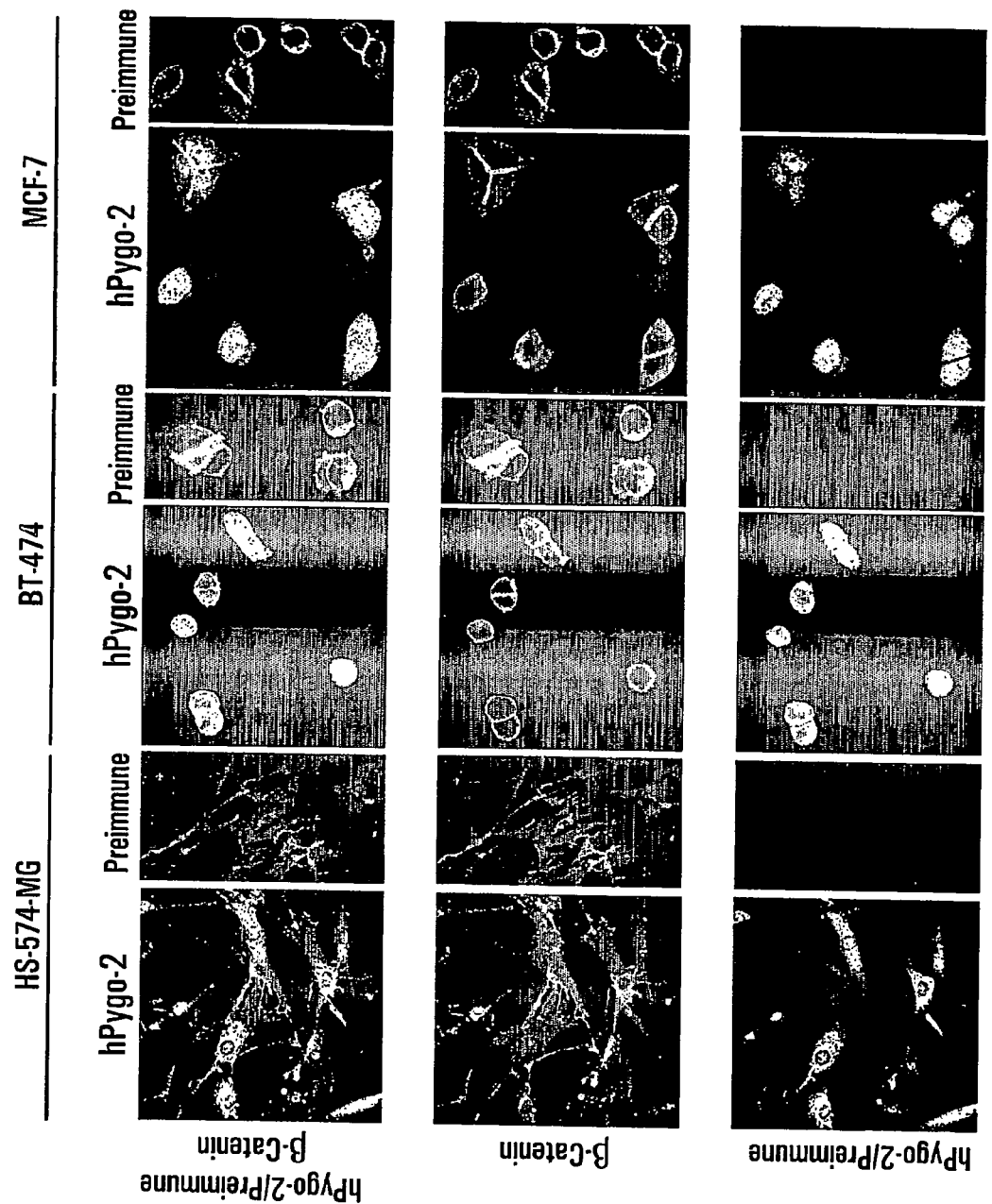

FIG. 10: Subcellular localization of hPygo2 and β-Catenin in normal breast (Hs-574) and malignant breast cancer (Bt-474, Mcf-7) cells using immunofluorescence and confocal microscopy. Preimmune serum used at the same dilution as hPygo2 immune serum for a negative control.

FIG. 11: Knockdown of β-Catenin in Mcf-7 cells by RNAi. Reagent control (the transfection agent Oligofectamine™) and non-specific siRNA controls are indicated.
(a) Western blot analysis showing knockdown of β-Catenin protein in Mcf-7 cells treated with siRNA. Loaded protein was standardized by reprobing blots with β-Actin.
(b) Cell proliferation 72 hours after initial treatment of cells with β-Catenin siRNA. Results indicated are based on three experiments performed in triplicate.

FIG. 12: Knockdown of endogenous hPygo2 mRNA and protein using antisense ON performed in HeLa cells. Reagent control (Oligofectamine™), antisense *Xenopus* Pygopus2 (non-specific), and four base mismatch (mismatch) controls are indicated. Levels of cDNA and protein were standardized with GAPDH and b-Actin. Experiments were performed in triplicate.
(a) RT-PCR analysis of both human Pygo family members that were previously treated with antisense ON, showing specific knockdown of hPygo2. RT−, negative control, without reverse transcriptase.
(b) Western blot analysis showing knockdown of hPygo2 protein.

FIG. 13: Knockdown of hPygo2 in Mcf-7 cells using antisense ONs. Reagent control (Oligofectamine™), antisense *Xenopus* Pygopus2 (non-specific), and four base mismatch (mismatch) controls are indicated.
(a) Confirmation of hPygo2 protein knockdown by western blot analysis of Mcf-7 total cell lysate that was treated with antisense ON.
(b) Cell proliferation 72 hours after initial treatment of cells with antisense ON. Results indicated are based on three experiments performed in triplicate.

Figure 14A:
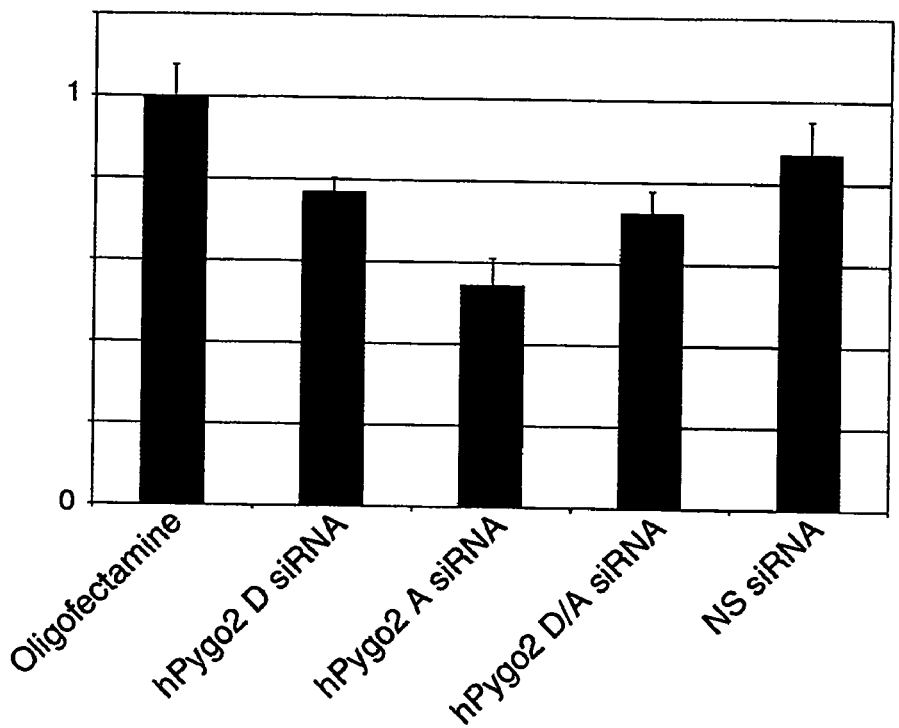
Figure 14B:
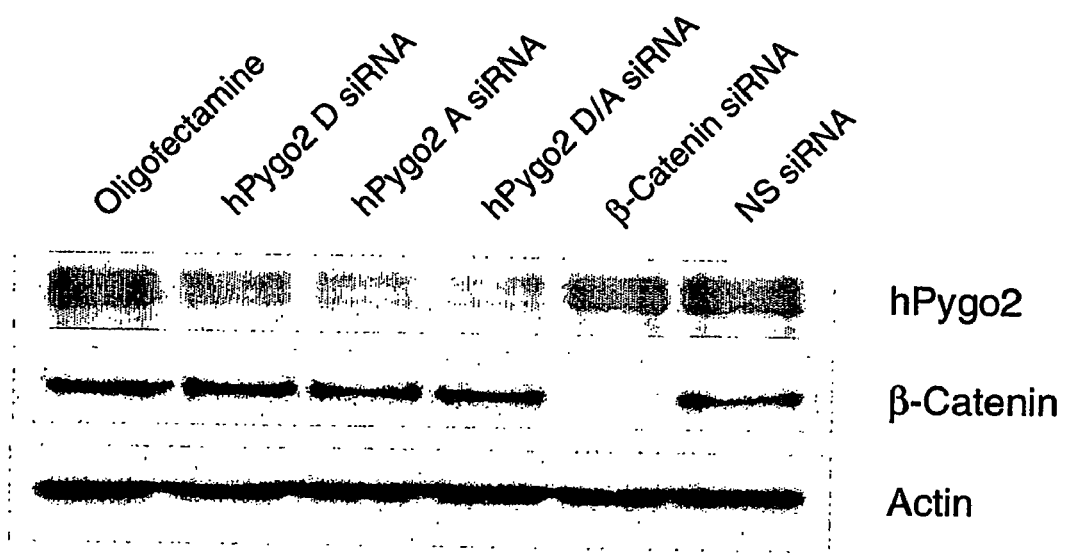

FIG. 14: (A and B) Knockdown of hPygo2 in Mcf-7 cells with siRNA. Reagent control (Oligofectamine™), Non-specific control siRNA (NS), β-Catenin and hPygo2A and hPygo2D siRNAs are indicated. Cell growth and knockdown of protein was assayed at 72 hrs after transfection. Results indicated are based on three experiments performed in triplicate.

FIG. 15: Anti-hPygo2 antibodies are used in immuno-histochemical analysis to identify malignant tumor cells from ovarian epithelial, breast, and lung cancer. Staining of archived tumors, as determined by a licenced pathologist, using anti-hPygo2 antibodies, indicates that Pygopus is specifically overexpressed in a variety of ovarian epithelial (A,C) tumors and in malignant breast (G) and lung cancer (H). Negative staining with pre-immune and secondary antibody alone demonstrates specificity of the antibody.

Figure 16A:
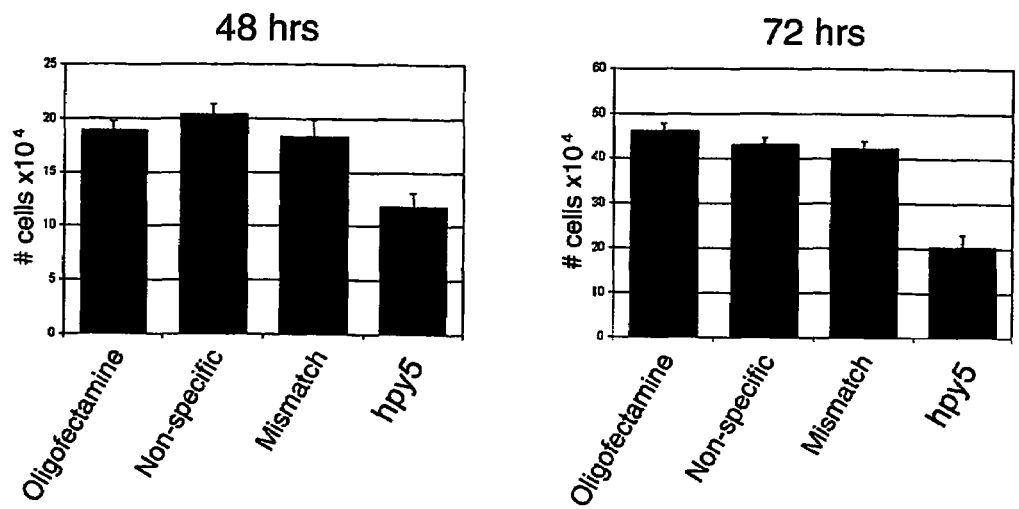
Figure 16B:
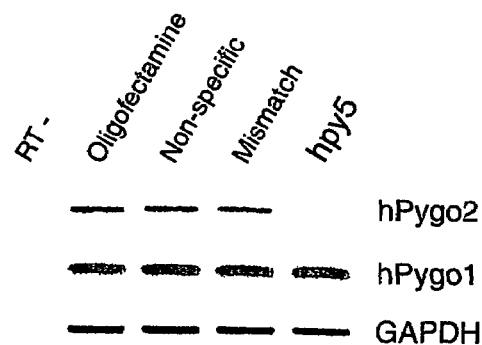
Figure 16C:
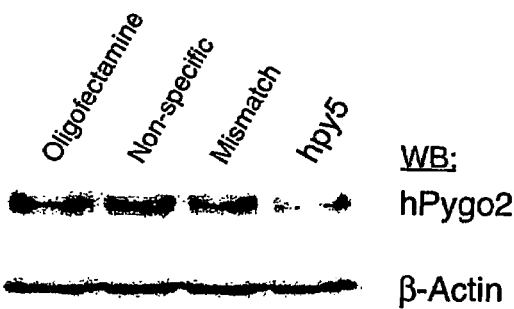

FIG. 16: Knockdown of endogenous hPygo2 using antisense ON in HeLa cervical cancer cells. Reagent control (Oligofectamine™), antisense *Xenopus* Pygopus2 (non-specific), and four base mismatch (mismatch) controls are indicated.

(a) HeLa cell numbers 48 and 72 hours after transfection with antisense ON.

(b) RT-PCR analysis of hPygo2 mRNA and of the related Pygo family member, hPygo1. RT−, negative control, without reverse transcriptase.

(c) Western blot analysis of endogenous hPygo2 protein. Levels of cDNA and protein were standardized using GAPDH and β-Actin.

DETAILED DESCRIPTION OF EMBODIMENTS (I) Polypeptides, Nucleic Acids and Uses:

The term "Pygopus" in the present context means nucleic acids and polypeptides which are homologs of the gene identified as SEQ ID NO:1. In humans, there are at least two Pygopus genes, hPygo1 (SEQ ID NOS:3 and 4) and hPygo2 (SEQ ID NOS:1 and 2); see FIGS. 1 and 2. Pygopus also refers to variants of the naturally occurring form of the gene, where the variants closely resemble the naturally occurring gene and retain the function(s) of the naturally occurring gene.

The term "isolated polynucleotide or polypeptide" is defined as a polynucleotide or polypeptide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. By "polypeptide" or "protein" is meant any chain of amino acids, regardless of length or post-translational modification (e.g., glycosylation or phosphorylation). Both terms are used interchangeably in the present application.

As used herein, "homologous amino acid sequence" is any polypeptide which is encoded, in whole or in part, by a nucleic acid sequence which hybridizes at 25-35° C. below critical melting temperature (Tm), to any portion of the nucleic acid sequence of SEQ ID No: 1 or 3. A homologous amino acid sequence is one that differs from an amino acid sequence shown in SEQ ID No: 2 or 4 by one or more conservative amino acid substitutions. Such a sequence encompasses those which retain inherent characteristics of the polypeptide such as immunogenicity. Preferably, such a sequence is at least 75%, more preferably 80%, and most preferably 90% identical to SEQ ID No: 2 or 4.

Homologous amino acid sequences include sequences that are identical or substantially identical to SEQ ID No:2 or 4. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions, i.e. substitutions among amino acids of the same class.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment.

In the present context, stringent conditions are achieved for both pre-hybridizing and hybridizing incubations (i) within 4-16 hours at 42° C., in 6×SSC containing 50% formamide, or (ii) within 4-16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

Partial sequences of SEQ ID No: 2 or 4 or their homologous amino acid sequences are inherent to the full-length sequences. Such polypeptide fragments preferably are at least 12 amino acids in length, preferably at least 15, 20, 25, 30, 35, 40, 45, 50 amino acids, more preferably at least 55, 60, 65, 70, 75 amino acids, and most preferably at least 80, 85, 90, 95, 100 amino acids in length.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources.

In the present context, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available.

The nucleic acid molecules encoding Pygopus and variants and fragments thereof, are useful for probes, primers, chemical intermediates, and in biological assays. The nucleic acid molecules are useful as a hybridization probe for messenger RNA, transcript/cDNA and genomic DNA and to isolate cDNA and genomic clones that correspond to variants (alleles, orthologs, etc.) producing the same or related peptides.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are useful for expressing antigenic portions of the proteins, as well as for designing antisense polynucleotides, siRNA-like molecules, or ribozymes corresponding to all, or a part, of the mRNA produced from the nucleic acid molecules described herein.

The nucleic acid molecules are also useful for making vectors that express part, or all, of Pygopus, and are also useful for constructing host cells expressing a part, or all, of the nucleic acid molecules and peptides.

The nucleic acid molecules are also useful as hybridization probes for determining the presence, level, form and distribution of nucleic acid expression. Experimental data as provided herein indicates that Pygopus is over-expressed in various human tumours. Accordingly, the probes can be used to detect the presence of, or to determine levels of, Pygopus in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Pygopus expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express Pygopus, such as by measuring a level of nucleic acid encoding Pygopus in a sample of cells from a subject e.g., mRNA or genomic DNA, or determining if the Pygopus gene has been mutated.

Nucleic acid expression assays are useful for drug screening to identify compounds that modulate Pygopus gene expression. The invention thus provides a method for identifying a compound that can be used to treat a disorder associated with expression of the Pygopus gene, particularly biological and pathological processes that are mediated by Pygopus in cells and tissues that express it. The method typically includes assaying the ability of the compound to modulate the expression of the Pygopus gene and thus identify a compound that can be used to treat a disorder characterized by undesired Pygopus gene expression. The assays can be performed in cell-based and cell-free systems. Cell-based assays include cells naturally expressing the Pygopus gene or recombinant cells genetically engineered to express specific Pygopus sequences.

The assay for Pygopus gene expression can involve direct assay of nucleic acid levels, such as mRNA levels, or on collateral compounds involved in the Wnt-signalling pathway. Further, the expression of genes that are up- or down-regulated in response to Wnt signalling pathway can also be assayed. In this embodiment the regulatory regions of these genes can be operably linked to a reporter gene such as luciferase.

Thus, modulators of Pygopus gene expression can be identified in a method wherein a cell is contacted with a test compound and the expression of mRNA determined. The level of expression of Pygopus mRNA in the presence of the test compound is compared to the level of expression of Pygopus mRNA in the absence of the test compound. The test compound can then be identified as a modulator of nucleic acid expression based on this comparison and be used, for example to treat a disorder characterized by aberrant nucleic acid expression. When expression of mRNA is statistically significantly greater in the presence of the test compound than in its absence, the test compound is identified as a stimulator of nucleic acid expression. When nucleic acid expression is statistically significantly less in the presence of the test compound than in its absence, the test compound is identified as an inhibitor of nucleic acid expression.

The nucleic acid molecules are also useful in diagnostic assays for qualitative changes in Pygopus gene expression, and particularly in qualitative changes that lead to cancer pathology. The nucleic acid molecules can be used to detect mutations in Pygopus genes and gene expression products such as mRNA. The nucleic acid molecules can be used as hybridization probes to detect naturally occurring genetic mutations in the Pygopus gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the Pygopus gene associated with a dysfunction provides a diagnostic tool for an active disease or susceptibility to disease when the disease results from overexpression, underexpression, or altered expression of Pygopus.

Sequence changes at specific locations can also be assessed by nuclease protection assays such as RNase and S1 protection or the chemical cleavage method. Furthermore, sequence differences between a mutant Pygopus gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127-162 (1996); and Griffin et al., Appl. Biochem. Biotechnol. 38:147-159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286-295 (1992)), electrophoretic mobility of mutant and wild type nucleic acid is compared (Orita et al, PNAS 86:2766 (1989); Cotton et al., Mutat. Res. 285:125-144 (1993); and Hayashi et al., Genet. Anal. Tech. Appl. 9:73-79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The invention also encompasses kits for detecting the presence of a pygopus nucleic acid in a biological sample. The kit can comprise reagents such as a labeled or labelable nucleic acid or agent capable of detecting Pygopus-2 gene or mRNA in a biological sample; means for determining the amount of Pygopus mRNA in the sample; and means for comparing the amount of Pygopus mRNA in the sample with a standard. The compound or agent can be packaged in a suitable container. The kit can further comprise instructions for using the kit to detect Pygopus mRNA or DNA.

II. Antisense Polynucleotides

In alternative embodiments, the invention provides antisense molecules and ribozymes for exogenous administration to effect the degradation and/or inhibition of the translation of Pygopus mRNA. Examples of therapeutic antisense oligonucleotide applications, incorporated herein by reference, include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423.

Preferably, in antisense molecules, there is a sufficient degree of complementarity to the Pygopus mRNA to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules is disclosed in U.S. Pat. No. 5,932,435.

As used herein, the term "target nucleic acid" encompass DNA encoding RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translocation of the RNA to sites within the cell which are distant from the site of RNA synthesis, translation of protein from the RNA, splicing of the RNA to yield one or more mRNA species, and catalytic activity which may be engaged in or facilitated by the RNA. The overall effect of such interference with target nucleic acid function is modulation of the expression of Pygopus. In the context of the present invention, "modulation" means either an increase (stimulation) or a decrease (inhibition) in the expression of a gene. In the context of the present invention, inhibition is the preferred form of modulation of gene expression and mRNA is a preferred target.

"Targeting" an antisense compound to a particular nucleic acid, in the context of this invention, is a multistep process. The process usually begins with the identification of a nucleic acid sequence whose function is to be modulated. In the present invention, the target is a nucleic acid molecule encoding Pygopus. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Pygopus, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA.

These alternative transcripts are generally known as "mRNA variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are complementary are hereinbelow referred to as "hybridization-accessible sites" and are therefore preferred sites for targeting. As used herein the term "hybridization-accessible site" is defined as at least an 8-nucleobase portion of a region of a gene that is accessible for hybridization with a complementary sequence of nucleic acid.

While the specific sequences of particular hybridization-accessible sites can be represented by the reverse complement of the antisense oligonucleotides set forth in Table 2, one of skill in the art will recognize that these serve to illustrate and describe particular embodiments within the scope of the present invention. Additional hybridization-accessible sites may be identified by one having ordinary skill.

Stretches of at least eight (8) consecutive nucleobases selected from within the illustrative hybridization-accessible sites are considered to be suitable hybridization-accessible sites as well, albeit exhibiting lower Tm values. Also, stretches of DNA or RNA that are about 8 to about 80 consecutive nucleobases and that comprise some portion of the 5'- or 3'-terminal sequence of a hybridization-accessible site will also be considered hybridization-accessible site for purposes of this invention. Exemplary good hybridization-accessible sites include DNA or RNA sequences that comprise at least the 8 consecutive nucleobases from the 5'-terminus of one a hybridization-accessible site (the remaining nucleobases being a consecutive stretch of the same DNA or RNA beginning immediately upstream of the 5'-terminus of the hybridization-accessible site and continuing until the DNA or RNA contains about 8 to about 80 nucleobases). Similarly good hybridization-accessible sites are represented by DNA or RNA sequences that comprise at least the 8 consecutive nucleobases from the 3'-terminus of a hybridization-accessible site (the remaining nucleobases being a consecutive stretch of the same DNA or RNA beginning immediately upstream of the 3'-terminus of the hybridization-accessible site and continuing until the target site contains about 8 to about 80 nucleobases).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 80 nucleobases (i.e. from about 8 to about 80 linked nucleosides). Particularly preferred antisense compounds are antisense oligonucleotides from about 8 to about 50 nucleobases, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases).

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. In addition, linear structures may also have internal nucleobase complementarity and may therefore fold in a manner as to produce a double stranded structure. Within the oligonucleotide structure, the phosphate groups are commonly referred to as forming the internucleoside backbone of the oligonucleotide. The normal linkage or backbone of RNA and DNA is a 3' to 51 phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene (methylimino) or MMI backbone), $CH_2$—O—N($CH_3$)—$CH_2$, $CH_2$—N($CH_3$)—N($CH_3$)—$CH_2$ and 0—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2 CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

The antisense compounds used in accordance with this invention may be conveniently and routinely made through the well-known technique of solid phase synthesis. Any other means for such synthesis known in the art may additionally or alternatively be employed. It is well known to use similar techniques to prepare oligonucleotides such as the phosphorothioates and alkylated derivatives.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

III. RNA Interference

Expression of a Pygopus-encoding nucleic acid or fragment thereof may be inhibited or prevented using RNA interference (RNAi) technology, a type of post-transcriptional gene silencing. RNAi may be used to create a pseudo "knockout" or "knock down", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example Hammond et al. (2001), Sharp (2001), Caplen et al. (2001), Sedlak (2000) and published US patent applications 20020173478 (Gewirtz; published Nov. 21, 2002) and 20020132788 (Lewis et al.; published Nov. 7, 2002), all of which are herein incorporated by reference. Reagents and kits for performing RNAi are available commercially from for example Ambion Inc. (Austin, Tex., USA) and New England Biolabs Inc. (Beverly, Mass., USA).

This invention relates to compounds, compositions, and methods useful for modulating expression of Pygopus by RNA interference (RNAi) using short interfering nucleic acid (siNA). A siNA of the invention can be unmodified or chemically modified. A siNA of the instant invention can be chemically synthesized, expressed from a vector, or enzymatically synthesized. The use of chemically-modified siNA is expected to improve various properties of native siNA molecules through increased resistance to nuclease degradation in vivo and/or improved cellular uptake. The siNA molecules of the instant invention provide useful reagents and methods for a variety of therapeutic and diagnostic applications.

The invention features one or more siNA molecules and methods that independently or in combination modulate the expression of Pygopus.

The invention also features a siNA molecule comprising 2'-5' internucleotide linkages. The 2'-5' internucleotide linkage(s) can be at 3'-end the 5'-end, the 3'-end, or both of the 5'- and 3'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In another embodiment, a chemically-modified siNA molecule of the invention comprises a duplex having two strands, one or both of which can be chemically modified, wherein each strand is between about 18 and about 27 (e.g., about 18, 19, 20, 21, 22, 23, 24, 25, 26, or 27) nucleotides in length, wherein the duplex has between about 18 and about 23 (e.g., about 18, 19, 20, 21, 22, or 23) base pairs.

In another embodiment, a siNA molecule of the invention comprises a single-stranded hairpin structure, wherein the siNA is between about 36 and about 70 (e.g., about 36, 40, 45, 50, 55, 60, 65, or 70) nucleotides in length having between about 18 and about 23 (e.g., about 18, 19, 20, 21, 22, or 23) base pairs, and wherein the siNA can include a chemical modification to improve various properties of native siNA molecules.

In another embodiment, a linear hairpin siNA molecule of the invention contains a stem loop motif, wherein the loop portion of the siNA molecule is biodegradable. For example, a linear hairpin siNA molecule of the invention is designed such that degradation of the loop portion of the siNA molecule in vivo can generate a double-stranded siNA molecule with 3'-terminal overhangs, such as 3'-terminal nucleotide overhangs comprising about 2 nucleotides.

In another embodiment, a siNA molecule of the invention comprises a circular nucleic acid molecule, wherein the siNA is between about 38 and about 70 (e.g., about 38, 40, 45, 50, 55, 60, 65, or 70) nucleotides in length having between about 18 and about 23 (e.g., about 18, 19, 20, 21, 22, or 23) base pairs, and wherein the siNA can include a chemical modification to improve various properties of native siNA molecules.

In another embodiment, a circular siNA molecule of the invention contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of mediating RNA interference or gene silencing. For example the siNA can be a double-stranded polynucleotide molecule comprising self-complementary sense and antisense regions, wherein the antisense region comprises complementarity to a target nucleic acid molecule. The siNA can be a single-stranded hairpin polynucleotide having self-complementary sense and antisense regions, wherein the antisense region comprises complementarity to a target nucleic acid molecule. The siNA can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active siNA capable of mediating RNAi. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In certain embodiments short interfering nucleic acids do not require the presence of nucleotides having a 2'-hydroxy group for mediating RNAi and as such, short interfering nucleic acid molecules of the invention optionally do not contain any ribonucleotides (e.g., nucleotides having a 2'-OH group). The modified short interfering nucleic acid molecules of the invention can also be referred to as short interfering modified oligonucleotides "siMON". As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA, short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post-transcriptional gene silencing.

By "modulate" is meant that the expression of the gene, or level of RNA molecule or equivalent RNA molecules encoding one or more proteins, or activity of one or more proteins is up-regulated or down-regulated, such that expression, level, or activity is greater than or less than that observed in the absence of the modulator. For example, the term "modulate" can mean "inhibit" but the use of the word "modulate" is not limited to this definition.

By "inhibit" is meant that the activity of a gene expression product or level of RNAs or equivalent RNAs encoding one or more gene products is reduced below that observed in the absence of the nucleic acid molecule of the invention. In one embodiment, inhibition with a siNA molecule preferably is below that level observed in the presence of an inactive or attenuated molecule that is unable to mediate an RNAi response.

The initial agent for RNAi in some systems is thought to be dsRNA molecule corresponding to a target nucleic acid. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

The siNA molecules of the invention can be designed to inhibit Pygopus gene expression through RNAi targeting of a variety of RNA molecules. In one embodiment, the siNA molecules of the invention are used to target various RNAs corresponding to a Pygopus gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, gene expression can be inhibited through the appropriate exons to specifically inhibit or to distinguish among the functions of gene family members.

In another embodiment, the siNA molecules of the invention are used to target conserved sequences corresponding to a family of Pygopus genes. As such, siNA molecules targeting multiple Pygopus genes can provide increased effect.

RNAi may be effected by the introduction of suitable in vitro synthesized siRNA or siRNA-like molecules into cells. RNAi may for example be performed using chemically-synthesized RNA. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods are described in the art. Various methods for introducing such vectors into cells, either in vitro or in vivo (e.g. gene therapy) are known in the art.

Accordingly, in some embodiments Pygopus expression may be inhibited by introducing into or generating within a cell an siRNA or siRNA-like molecule corresponding to a Pygopus-encoding nucleic acid or fragment thereof, or to an nucleic acid homologous thereto. "siRNA-like molecule" refers to a nucleic acid molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a Pygopus-encoding nucleic acid or a fragment or variant (or a fragment of a variant) thereof. Such a variant is capable of encoding a protein having Pygopus-like activity. In embodiments, the sense strand of the siRNA or siRNA-like molecule is substantially identical to the Pygopus nucleotide sequence, or a fragment thereof (RNA having U in place of T residues of the DNA sequence).

IV. Delivery of Nucleic Acid Molecules into Cells

A siNA molecule of the invention can be adapted for use to inhibit cancer cell proliferation, alone or in combination with other therapies. For example, a siNA molecule can comprise a delivery vehicle, including liposomes, for administration to a subject, carriers and diluents and their salts, and/or can be present in pharmaceutically acceptable formulations.

Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713, and Sullivan et al., PCT WO 94/02595, further describe the general methods for delivery of nucleic acid molecules. These protocols can be utilized for the delivery of virtually any nucleic acid molecule.

Nucleic acid molecules can be administered to cells by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a patient.

Thus, the invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

By "pharmaceutically acceptable formulation" is meant, a composition or formulation that allows for the effective distribution of the nucleic acid molecules of the instant invention in the physical location most suitable for their desired activity.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug. Such liposomes have been shown to accumulate selectively in tumors, presumably by extravasation and capture in the neovascularized target tissues. The long-circulating liposomes enhance the pharmacokinetics and pharmacodynamics of DNA and RNA, particularly compared to conventional cationic liposomes which are known to accumulate in tissues of the MPS. Long-circulating liposomes are also likely to protect drugs from nuclease degradation to a greater extent compared to cationic liposomes, based on their ability to avoid accumulation in metabolically aggressive MPS tissues such as the liver and spleen.

V. Screening Assays

In another aspect, the invention relates to the use of Pygopus as a target in screening assays that may be used to identify compounds that are useful as inhibitors of Pygopus for the prevention or treatment of cancer. In some embodiments, such an assay may comprise the steps of:

(a) providing a test compound;
(b) providing a source of Pygopus; and
(c) measuring Pygopus activity in the presence versus the absence of the test compound, wherein a lower measured activity in the presence of the test compound indicates that the compound is an inhibitor of Pygopus-dependent signal and may be useful for the prevention and/or treatment of cancer.

"Pygopus activity" as used herein refers to any type of observed phenomenon which can be attributed to Pygopus, via for example the transcriptional activation of Wnt-responsive genes or inhibition of cancer cell proliferation. Transcriptional activation of Wnt-responsive genes may be assayed using any methods known in the art. Usually such methods involve measuring the activity of a reporter gene operably linked to a promoter, itself operably linked to Wnt-responsive regulatory regions normally present in genes activated by the Wnt pathway. In one embodiment, this transcriptional activity is measured with a luciferase reporter (TOPFLASH, provided by Upstate: Cell Signalling Solutions, Charlottesville Va., USA; B-catenin Luciferase reporter construct; Korinek, V. et al., 1997, Science 275: 1784-1787, incorporated herein by reference) that contains multiple T-cell Factor (TCF) binding sites, which are directly activated by the TCF/b-catenin complex. To control for non-specific repression or activation, a reporter with mutant Lef-1 binding sites (FOPFLASH) was substituted for TOPFLASH, and luciferase activity measured from the TOPFLASH reporter is normalized accordingly.

The assay methods of the invention may be used to identify compounds capable of modulating, e.g. inhibiting, Pygopus, in a biological system. In embodiments, the above noted biological system may be a mammal, such as a human, or a suitable animal model system such as *Xenopus*.

The invention further provides a method of identifying a compound for the prevention and/or treatment of cancer based on the identification of a compound capable of modulating (e.g. inhibiting) Pygopus expression. Such a method may comprise assaying Pygopus gene expression in the presence versus the absence of a test compound. Such gene expression may be measured by detection of the corresponding RNA or protein, or via the use of a suitable reporter construct comprising a transcriptional regulatory element(s) normally associated with such a Pygopus gene, operably-linked to a reporter gene. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

"Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) *Antibodies: A Laboratory Manual*, Cold Spring Harbor Laboratory Press, Cold Spring Harbor, N.Y.]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, or green fluorescent protein.

The above-noted methods and assays may be employed either with a single test compound or a plurality or library (e.g. a combinatorial library) of test compounds. In the latter case, synergistic effects provided by combinations of compounds may also be identified and characterized. The above-mentioned compounds may be used for inhibiting Pygopus, and for the prevention and/or treatment of cancer, or may be used as lead compounds for the development and testing of additional compounds having improved specificity, efficacy and/or pharmacological (e.g. pharmacokinetic) properties. In certain embodiments, one or a plurality of the steps of the screening/testing methods of the invention may be automated.

Such assay systems may comprise a variety of means to enable and optimize useful assay conditions. Such means may include but are not limited to: suitable buffer solutions, for example, for the control of pH and ionic strength and to provide any necessary components for optimal Pygopus activity and stability (e.g. protease inhibitors), temperature control means for optimal Pygopus activity and or stability, and detection means to enable the detection of the Pygopus activity. A variety of such detection means may be used, including but not limited to one or a combination of the following: radiolabelling (e.g. $^{32}P$), antibody-based detection, fluorescence, chemiluminescence, spectroscopic methods (e.g. generation of a product with altered spectroscopic properties), various reporter enzymes or proteins (e.g. horseradish peroxidase, green fluorescent protein), specific binding reagents (e.g. biotin/(streptavidin), and others. Binding may also be analysed using generally known methods in this area, such as electrophoresis on native polyacrylamide gels, as well as fusion protein-based assays such as the yeast 2-hybrid system or in vitro association assays, or proteomics-based approachs to identify Pygopus binding proteins.

The assay may be carried out in vitro utilizing a source of Pygopus which may comprise naturally isolated or recombinantly produced Pygopus, in preparations ranging from crude to pure. Recombinant Pygopus may be produced in a number of prokaryotic or eukaryotic expression systems which are well known in the art. Such assays may be performed in an array format. In certain embodiments, one or a plurality of the assay steps are automated.

A homolog, variant and/or fragment of Pygopus which retains activity, particularly the ability to activate Wnt-responsive genes or inhibit cancer cell proliferation, may also be used in the methods of the invention. Homologs includes protein sequences which are substantially identical to the amino acid sequence of a Pygopus, sharing significant structural and functional homology with a Pygopus. Variants include, but are not limited to, proteins or peptides which differ from a Pygopus by any modifications, and/or amino acid substitutions, deletions or additions. Such variants include fusion proteins, for example a protein of interest or portion thereof fused with a suitable fusion domain (such as glutathione-S-transferase fusions, and others). Modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of Pygopus or a fragment or a portion of a homolog or variant of Pygopus.

The assay may in an embodiment be performed using an appropriate host cell as a source of Pygopus. Such a host cell may be prepared by the introduction of DNA encoding Pygopus into the host cell and providing conditions for the expression of Pygopus. Such host cells may be prokaryotic or eukaryotic, bacterial, yeast, amphibian or mammalian.

The above-described assay methods may further comprise determining whether any compounds so identified can be used for the prevention or treatment of cancer, such as examining their effect(s) on disease symptoms in suitable cancer animal model systems. The above-mentioned methods may similarly be used to identify and characterize compounds for the modulation of Pygopus in a system.

VI. Binding Assays

Pygopus can be used in assays related to the functional information provided herein; to raise antibodies or to elicit another immune response; as a reagent (including the labeled reagent) in assays designed to quantitatively determine levels of the protein in biological fluids; and as markers for tissues in which the corresponding protein is preferentially expressed (either constitutively or at a particular stage of tissue differentiation or development or in a disease state). Where the protein binds or potentially binds to another protein or ligand, the protein can be used to identify the binding partner/ligand so as to develop a system to identify inhibitors of the binding interaction. Any or all of these uses are capable of being developed into reagent grade or kit format as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The Pygopus proteins of the present invention (including variants and fragments that may have been disclosed prior to the present invention) are useful for biological assays related to Wnt-signalling and to cancer. Such assays involve Pygopus functions or activities or properties useful for diagnosis and treatment of cancer, particularly in cells and tissues that express Pygopus. Experimental data as provided herein indicates that Pygopus is over-expressed in human tumour tissue.

Pygopus and fragments, particularly the NHD region, are also useful in drug screening assays, in cell-based or cell-free systems. Cell-based systems can be native, i.e., cells that normally express Pygopus, as a biopsy or expanded in cell culture. In an alternate embodiment, cell-based assays involve recombinant host cells expressing Pygopus or its fragments, particularly the NHD region.

Pygopus and fragments, particularly the NHD region, can be used to identify compounds that modulate the Wnt-signalling activation function of the protein in its natural state or an altered form. Pygopus and appropriate variants and fragments can be used in high-throughput screens to assay candidate compounds for the ability to bind to Pygopus and fragments, particularly the NHD region. These compounds can be further screened against a functional Pygopus to determine the effect of the compound on Pygopus activity. Further, these compounds can be tested in animal or invertebrate systems, particularly *Xenopus*, or in cancer cell lines, to determine activity/effectiveness. Compounds can be identified that activate (agonist) or inactivate (antagonist) Wnt signalling to a desired degree.

Further, Pygopus and fragments, particularly the NHD region, can be used to screen a compound for the ability to stimulate or inhibit interaction between Pygopus and a molecule (binding partner) that normally interacts with Pygopus, e.g. Bcl-2. Such assays typically include the steps of combining Pygopus and fragments, particularly the NHD region, with a test compound under conditions that allow Pygopus and fragments, particularly the NHD region, to interact with the binding partner, and to detect the formation of a complex between Pygopus and the binding partner, or to detect the biochemical consequence of the interaction, such as activation of Wnt signalling.

Test compounds include, for example, 1) peptides such as soluble peptides, including Ig-tailed fusion peptides and members of random peptide libraries and combinatorial chemistry-derived molecular libraries made of D- and/or L-configuration amino acids; 2) phosphopeptides (e.g., members of random and partially degenerate, directed phosphopeptide libraries); 3) antibodies (e.g., polyclonal, monoclonal, humanized, anti-idiotypic, chimeric, and single chain antibodies as well as Fab, F(ab').sub.2, Fab expression library fragments, and epitope-binding fragments of antibodies); and 4) small organic and inorganic molecules (e.g., molecules obtained from combinatorial and natural product libraries).

Binding and/or activating compounds can also be screened by using fusion proteins in which the amino terminal domain, or parts thereof, and the carboxy terminal domain, or parts thereof, can be replaced by heterologous polypeptides. These are generally referred to as chimeric or fusion proteins.

Chimeric and fusion proteins comprise Pygopus and fragments, particularly the NHD region, operatively linked to a heterologous protein having an amino acid sequence not substantially homologous to the Pygopus in the fusion. "Operatively linked" indicates that the Pygopus in the fusion and the heterologous protein are fused in-frame. The heterologous protein can be fused to the N-terminus or C-terminus of the Pygopus in the fusion.

In some uses, the fusion protein does not affect the activity of the Pygopus in the fusion. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Pygopus and fragments, particularly the NHD region. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence. Moreover, many expression vectors are commercially available that already encode a fusion moiety (e.g., a GST protein). A nucleic acid encoding Pygopus and fragments, particularly the NHD region, can be cloned into such an expression vector such that the heterologous moiety is linked in-frame to Pygopus.

Pygopus and fragments, particularly the NHD region, are also useful in competition binding assays in methods designed to discover compounds that interact with Pygopus (e.g. binding partners and/or ligands). Thus, a compound is exposed to Pygopus and fragments, particularly the NHD region, under conditions that allow the compound to bind or to otherwise interact with the polypeptide. A known binding partner such as Bcl-9 or an antibody, particularly a monoclonal antibody to Pygopus, is also added to the mixture. If the test compound interacts with Pygopus, it may decrease the amount of complex formed between Pygopus and the known binding partner. This type of assay is particularly useful in cases in which compounds are sought that interact with specific regions of Pygopus. Thus, the binding partner that competes with the test compound is designed to bind to peptide sequences corresponding to the region of interest in Pygopus.

In one embodiment, the competitor is a binding partner known to bind to Pygopus, such as an antibody, peptide, ligand, etc. Under certain circumstances, there may be competitive binding as between the test compound and the binding partner, with the binding moiety displacing the candidate agent.

Competitive screening assays may be done by combining Pygopus and fragments, particularly the NHD region, and a test compound in a first sample. A second sample comprises the test compound, Pygopus and fragments, particularly the NHD region, and a known binding partner. The binding of the binding partner with Pygopus is determined for both samples, and a change, or difference in binding between the two samples indicates the presence of an agent capable of binding to Pygopus and potentially modulating its activity, i.e its interaction with the known binding partner. That is, if the binding of the candidate agent is different in the second sample relative to the first sample, the test compound is capable of binding to Pygopus.

In one embodiment, the test compound is labeled. Either the test compound, or the binding partner, or both, is added first to Pygopus and fragments, particularly the NHD region, for a time sufficient to allow binding. Incubations may be performed at any temperature which facilitates optimal activity, typically between 4 and 40 degree C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the binding partner is added first, followed by the test compound. Displacement of the binding partner is an indication the test compound is binding to Pygopus and thus is capable of binding to, and potentially modulating, the activity of Pygopus. In this embodiment, either component can be labeled. Thus, for example, if the binding partner is labeled, the presence of label in the wash solution indicates displacement by the test compound. Alternatively, if the test compound is labeled, the presence of the label on the support indicates displacement.

In an alternative embodiment, the test compound is added first, with incubation and washing, followed by the binding partner. The absence of binding by the binding partner may indicate the test compound is bound to Pygopus with a higher affinity. Thus, if the test compound is labeled, the presence of the label on the support, coupled with a lack of binding by the binding partner, may indicate the test compound is capable of binding to Pygopus.

To perform cell free drug screening assays, it is sometimes desirable to immobilize either Pygopus and fragments, particularly the NHD region, or its binding partner, to facilitate separation of complexes from uncomplexed forms of one or both components, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads or glutathione derivatized microtitre plates, which are then combined with the cell lysates (e.g., 35 S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Pygopus-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a binding partner and a test compound are incubated in the Pygopus2-presenting wells and the amount of complex trapped in the well can be quantitated. Methods for detecting such complexes, in addition to those described above for the GST-immobilized complexes, include immunodetection of complexes using antibodies, as well as enzyme-linked assays which rely on detecting an enzymatic activity associated with the complex.

Agents that modulate or inhibit Pygopus and fragments, particularly the NHD region, can be identified using one or more of the above assays, alone or in combination. It is generally preferable to use a cell-based or cell free system first and then confirm activity in an animal or other model system. Such model systems are well known in the art and can readily be employed in this context.

In yet another aspect of the invention, Pygopus and fragments, particularly the NHD region, can be used as "bait proteins" in a two-hybrid assay or three-hybrid assay to identify other proteins, which bind to or interact with Pygopus and fragments, particularly the NHD region. Such binding proteins are likely to be involved in the propagation of signals of the Wnt pathway. Alternatively, such binding proteins are also likely to be inhibitors of Pygopus.

The two-hybrid system is based on the modular nature of most transcription factors, which consist of separable DNA-binding and activation domains. Briefly, the assay utilizes two different DNA constructs. In one construct, the gene that codes for Pygopus and fragments, particularly the NHD region, is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with Pygopus and fragments, particularly the NHD region.

This invention further pertains to agents identified by the above-described screening assays. Accordingly, it is within the scope of this invention to further use an agent identified as described herein in an appropriate animal model. For example, an agent identified as described herein (e.g., Pygopus-modulating agent, an antisense Pygopus nucleic acid molecule, a Pygopus-specific antibody, or a Pygopus-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

Pygopus and fragments, particularly the NHD region, are also useful to provide a target for diagnosing cancer or predisposition to cancer. Accordingly, the invention provides methods for detecting the presence, or levels of, the protein (or encoding mRNA) in a cell, tissue, or organism. Experimental data as provided herein indicates Pygopus over-expression in humans in various tumour tissues. The method involves contacting a biological sample with a compound capable of interacting with Pygopus and fragments, particularly the NHD region, such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

Pygopus and fragments, particularly the NHD region, also provide targets for diagnosing active protein activity, disease, or predisposition to disease. Thus, Pygopus can be isolated from a biological sample and assayed for the presence of a genetic mutation that results in aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered activation of Wnt-signalling activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of Pygopus or fragments include enzyme linked immunosorbent assays (ELISAs), Western blots, immunoprecipitations and immunofluorescence using a detection reagent, such as an antibody or protein binding agent. Alternatively, the protein can be detected in vivo in a subject by introducing into the subject a labeled antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

Pygopus and fragments, particularly the NHD region, are also useful in cancer-related pharmacogenomic analysis. Pharmacogenomics deal with clinically significant hereditary variations in the response to drugs due to altered drug disposition and abnormal action in affected persons. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of Pygopus-2 in which one or more of the Pygopus-2 functions in one population is different from those in another population. Accordingly, dosage of a certain drug may be modified to maximize the therapeutic effect within a given population containing a polymorphism. As an alternative to genotyping, specific polymorphic peptides could be identified.

VII. Antibodies

The invention also provides antibodies that selectively bind to Pygopus as well as variants and fragments thereof (the target peptide). As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target such that there are shared epitopes. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given antigen. Antibodies are generated by immunization of a mammal with Pygopus or a fragment thereof. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680. For monoclonal antibodies, see Kohler & Milstein (1975) Nature 256:495-497.

In general, to generate antibodies, an isolated peptide is used as an immunogen and is administered to a mammalian organism, such as a rat, rabbit or mouse. The antibodies may then be harvested from the organism. The full-length protein, an antigenic peptide fragment or a fusion protein can be used. Particularly important fragments are those covering functional domains, such as the NHD domain, and regions unique to Pygopus or fragments thereof, such as those that can readily be identified using protein alignment methods and as presented herein.

In one embodiment, a monoclonal antibody is produced which binds specifically to Pygopus or fragments thereof. The method comprises immunizing an animal with Pygopus or fragments thereof to produce immunocytes for harvesting; obtaining immunocytes, such as splenocytes, from the immunized animal; and fusing the immunocytes with myeloma cell, whereby screening for fused cells identifies hybridomas which produce the monoclonal antibody.

Antibodies are preferably prepared from regions or discrete fragments of Pygopus or fragments thereof. Antibodies can be prepared from any region of the peptide as described herein. However, preferred regions will include those unique to Pygopus, such as regions outside of the N-box and the PHD domain.

An immunogenic epitope will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{13}$I, $^{35}$S or $^{3}$H.

VIII. Antibody Uses

The antibodies can be used to isolate Pygopus or fragments thereof by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development.

Experimental data as provided herein indicates that Pygopus is over-expressed in humans in various tumour tissues. Such antibodies can be used to detect protein in situ, in vitro, or in a cell lysate or supernatant in order to evaluate the abundance and pattern of expression. Detection of Pygopus overexpression can be used to diagnose cancer. Such antibodies can also be used to assess abnormal tissue distribution or abnormal expression during development or progression of a biological condition.

Further, the antibodies can be used to assess expression in disease states such as in active stages of cancer or in an individual with a predisposition toward disease related to the protein's function. When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies are also useful for inhibiting protein function, for example, blocking the binding of Pygopus or fragments thereof to a binding partner such as Bcl-9. These uses can also be applied in a therapeutic context in which treatment involves inhibiting the protein's function. An antibody can be used, for example, to block binding, thus modulating (agonizing or antagonizing) Pygopus activity. Antibodies can be prepared against specific fragments containing sites required for function or against intact protein that is associated with a cell or cell membrane.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays have been described in detail for nucleic acid arrays and similar methods have been developed for antibody arrays.

EXAMPLE 1

Pygopus is a Diagnostic and Therapeutic Target in Epithelial Ovarian Carcinoma (1) Detailed Protocols
(a) Cell culture: Cell lines were obtained from American Type Culture Collection (ATCC, USA) and were cultured in DMEM (GIBCO BRL, USA) containing 10% Fetal calf serum (FCS), 100 U/ml of penicillin, 100 µg/ml of streptomycin. Normal ovarian surface epithelial (OSE) cells were scraped from ovaries (patient consent approval) and cultured in MCDB105 (Sigma, USA) and 199 (Sigma, USA) (1:1) containing 15% FCS, 100 U/ml of penicillin and 100 µg/ml of streptomycin as described (Wong, A. S. & Auersperg, N. Ovarian surface epithelium: family history and early events in ovarian cancer. *Reprod. Biol. Endocrinol.* 1, 70 (2003)). Cells were counted using a hemacytometer.

TABLE 1

Characteristics of various epithelial ovarian cell (EOC) lines

| EPITHELIAL OVARIAN CELL LINES | Tissue |
| --- | --- |
| OVCAR-3 | Ovary; epithelial; adenocarcinoma |
| OV-90 | Ovary; metastatic site: ascites malignant papillary serous adenocarcinoma |
| TOV-21G | Ovary; clear cell carcinoma |
| ES-2 | Ovary; clear cell carcinoma |
| TOV-112D | Ovary; endometrioid carcinoma |
| SKOV-3 | Ovary; metastatic site: ascites adenocarcinoma |
| OSE-2 | Ovary; epithelial, normal |
| IOSE-397 | Ovary; epithelial, immortalized |

(b) RNA extraction and Northern Blotting: Total cellular RNA was extracted using the RNA purification kit RNeasy™ Mini Kit (Qiagen, QP, CANADA). Northern blot analysis was performed using a 32P-dCTP-labelled cDNA probes in Rapid-Hyb buffer at 65° C. for one hour and washed to high stringency in 0.1× at 65° C. for 15 minutes as described (Lake, B. B. & Kao, K. R. Pygopus is required for embryonic brain patterning in *Xenopus*. Dev. Biol. 261, 132-148 (2003)).

(c) Protein extraction and Western blotting: For protein extraction, 80-90% confluent transfected or untransfected cell monolayers were washed with cold Phosphate Buffered Saline (PBS), lysed immediately in 2× Sodium Dodecyl Sulfate (SDS) loading buffer, passed through 21G syringe needle to shear the viscous DNA and loaded onto 10-12% SDS-denaturing polyacrylamide gel. The fractionated proteins were then transferred to Hybond enhanced chemiluminescent (ECL) nitrocellulose membrane (Amersham Pharmacia Biotech, PQ, CANADA) under semi-dry condition. Immunodetection was performed using the ECL system (Amersham Pharmacia Biotech, PQ, CANADA). Anti-hPygo2 polyclonal antisera were raised in New Zealand White rabbits as described (Reynolds et al. Developmental expression of functional GABAA receptors containing the gamma 2 subunit in neurons derived from embryonal carcinoma (P19) cells. *Brain Res. Mol. Brain Res.* 35, 11-18 (1996)) using an in vitro synthesized polypeptide corresponding to amino acid residues 89-328, lacking both NHD and PHD conserved (Kramps, T. et al. Wnt/wingless signaling requires BCL9/legless-mediated recruitment of pygopus to the nuclear beta-catenin-TCF complex. Cell 109, 47-60 (2002)) regions of hPygo2, which was generated by subcloning hPygo2 cDNA sequences derived by PCR from a human EST clone (I.M.A.G.E.) into pGex4T1 (Amersham) and tested by immunoprecipitation and western analysis. Anti β-Catenin, anti c-Myc and anti Erk-1 antibodies were purchased from Santa Cruz. Anti GSK-3β and anti phospho-GSK-3α/β antibodies were purchased from Cell Signaling Technology.

(d) Immunohistochemistry: Archived, paraffin embedded tumors were sectioned at 5 microns, mounted on glass slides (Surgipath) and processed using a citrate-based antigen recovery protocol (Rorke, S., Murphy, S., Khalifa, M., Chernenko, G., & Tang, S. C. Prognostic significance of BAG-1 expression in nonsmall cell lung cancer. *Int. J. Cancer* 95, 317-322 (2001)) with hPygo2 primary antisera (diluted 1000×) β-catenin mouse monoclonal primary antibodies (Santa Cruz, diluted 2000×), anti-mouse and anti-rabbit HRP-linked secondary antibodies diluted 1/250× (Amersham), counterstained with hematoxylin and mounted in Permount (Fisher) as described (supra). The concentration of primary antibody used was determined by level at which there was no staining, either background or non-specific observed using both pre-immune serum and secondary antibody alone.

(e) Immunofluorescence: Cells were plated onto glass chamber slides and fixed in 4% paraformaldehyde for 30 minutes, rinsed in Phosphate buffered saline (PBS) twice, followed by 0.2% triton-X100 in PBS (tPBS) for 10 minutes. Cells were blocked in 10% normal donkey or goat serum and incubated overnight at 4° C. with primary antibodies in 1.5% normal serum in PBS. The next day the slides were washed for 30 to 40 minutes in 0.2% tPBS and incubated for 30 minutes at room temperature with biotinylated donkey anti-rabbit (Amersham) or Cy3 donkey anti-mouse (Jackson ImmunoResearch Laboratories, Inc.) secondary antibodies in 1.5% normal sera. After a 30 to 40 minute wash in 0.1-0.2% tPBS, cells were incubated in streptavidin fluorescein (Amersham) in 1.5% normal sera/PBS for 30 minutes, washed in 0.1-0.2% tPBS 30 to 40 minutes mounted in 10% glycerol/PBS or the mounting medium Vectashield™ (Vector Laboratories, Inc.) and viewed under confocal microscopy using filters optimized for fluorescein and Cy3.

(f) Knockdown Assays: Antisense oligonucleotides were designed against hPygo2 (Table 2).

TABLE 2

Antisense oligonucleotides against hPygo2

| Oligo name | Sequence (5'-3') | Target region (SEQ ID NO: 1) |
|---|---|---|
| Hpy1 | GAGCTGCAGCAACCACAAAG (SEQ ID NO: 5) | 55-74 |
| Hpy2 | GGACCCGGGTTAGCGGCAGCG (SEQ ID NO: 6) | 144-164 |
| Hpy3 | CCACCTCCCTCCAGCTTGTCC (SEQ ID NO: 7) | 198-219 |
| Hpy4 | GGAGGACTAAAGTTTTGAC (SEQ ID NO: 8) | 687-705 |
| Hpy5 | GGCTGAGCAAATCGTTGGG (SEQ ID NO: 9) | 807-825 |
| Hpy6 | GAAAAGCAGTAGAAGCAGGT (SEQ ID NO: 10) | 967-986 |
| Hpy7 | CTCACGGATGTAGACAGA (SEQ ID NO: 11) | 1340-1357 |
| Hpy8 | CCTCTGGCCAGAAACCTTT (SEQ ID NO: 12) | 1817-1835 |

TABLE 2-continued

Antisense oligonucleotides against hPygo2

| Oligo name | Sequence (5'-3') | Target region (SEQ ID NO: 1) |
|---|---|---|
| Hpy9 | CTCTTCTACCTTTGAGTAC (SEQ ID NO: 13) | 2434-2452 |
| Hpy10 | CACTGTATCTTGAGCTGG (SEQ ID NO: 14) | 2720-2737 |

$5 \times 10^4$ of SK-OV-3 cells and $6 \times 10^4$ of NIH-OVCAR-3 cells were seeded into 12-well plates 24 hrs before transfection. 100-200 nM of 19 mer oligonucleotides containing 3 phosphorothioated bonds (*) at each terminus (5'-G*G*C*TGAGCAAATCGTT*G*G*G-3'; Hpy5) from the coding region (nt no. 807-825) of hPygo2 (SEQ ID NO:1) and its mismatched sequence (5'-G*C*C*TGAGCTAATCATT*G*G*T-3'; SEQ ID NO:20) or anti-*Xenopus* pygo2 oligonucleotides (5'-T*T*T*GCGCCGTTTCTT*C*T*C-3'; SEQ ID NO:21) was transfected into NTH-OVCAR-3 using the Oligofectamine™ Transfection Kit (Invitrogen, CA, USA) and SK-OV-3 using Effectene™ Transfection Kit (Qiagen, QP, CANADA). The culture medium was changed after 24 and 48 hours transfection.

β-Catenin siRNA, consisting of 4 pooled siRNAs was purchased from Upstate. hPygo2 siRNA was chemically synthesized from Qiagen. Individual siRNAs were tested for their ability to knock down hPygo2 as assayed by western analysis.

Hpy2A:
5'-r(CGAUGACCAGGAUGCCAUU)d(TT)-3'  SEQ ID NO: 15

Hpy2B:
5'-r(AGAAGCGAAGGAAGUCAAA)d(TT)-3'  SEQ ID NO: 16

Hpy2C:
5'-r(UGGGAACCAGCCCAGUUUC)d(TT)-3'  SEQ ID NO: 17

Hpy2D:
5'-r(CCAGCCUCUGGGUCAAAAC)d(TT)-3'  SEQ ID NO: 18

Hpy2E:
5'-r(CUUUCCCAGCCAACCCUUC)d(TT)-3'  SEQ ID NO: 19

Two (Hpy2A and Hpy2D) out of 5 of the siRNAs were effective in knocking down hPygo2.

Transfection of siRNA was performed as for the antisense ON, using either Oligofectamine™ or RNAiEasy (Qiagen). Cells were washed in PBS 6 hours after transfection of 100 nM of siRNA and replaced with fresh medium, followed by an additional transfection of 100 nM of siRNA 24 hours later. The cells were then fixed and stained with propidium iodide and counted for DNA content using a Fluorescence Activated Cell Sorter.

(2) Specificity of Anti-hPygo2 Antibody

Different regions of hPygo2 were fused to Gal-4 and the constructs were transiently transfected into HeLa cells. Protein was extracted and analyzed for the expression of the transfected constructs. The same amount of protein was loaded and transferred for both blots. FIG. 3(*a*) depicts Gal-4-hPygo2 fusion protein constructs that were transfected into HeLa cells. FIG. 3(*b*) shows a Western blot of Gal-4-hPygo2 constructs using anti-hPygo2 antiserum; see Example 1(1). FIG. 3(*c*) shows a Western blot of Gal-4-hPygo2 constructs using an anti-Gal-4 antibody. The Gal-4 antibody recognizes all Gal-4-hPygo2 protein constructs.

Figure 3A:
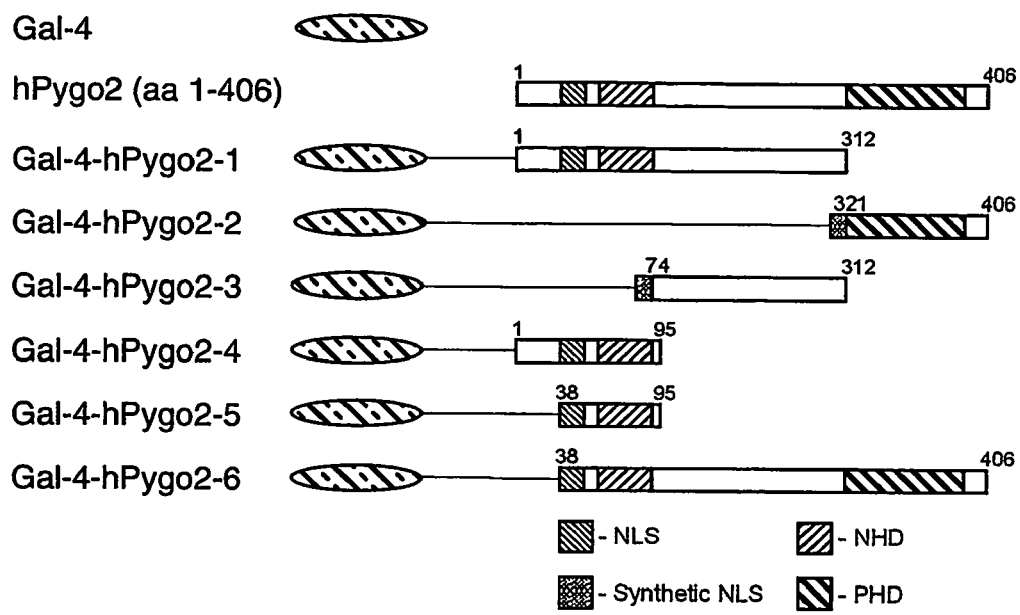
FIG. 3: Ability of anti-hPygo2 immune serum to recognize different regions of hPygo2.
(a) Gal-4-hPygo2 fusion protein constructs.
(b) Western analysis of Gal-4-hPygo2 constructs transiently transfected into HeLa cells using anti-hPygo2 antiserum.
(c) Western analysis of Gal-4-hPygo2 constructs using an anti-Gal-4 antibody.
(d) and (e) Similar experiments conducted with fusions to Flag peptide.
(f) Immunocytochemical analyses of four OvCa cell lines using anti-hPygo2 antibodies and beta-catenin.
(g) Antisense oligonucleotides mapped to the full hPygo2 cDNA sequence. (h) Antisense oligonucleotides transfected into HeLa cells and RT-PCR analysis performed to assess the relative knockdown of hPygo2 RNA levels. Densitometric scan shows the relative hPygo2 levels compared to the relative GAPDH levels. RT−, negative control, without reverse transcriptase.
Figure 3B:
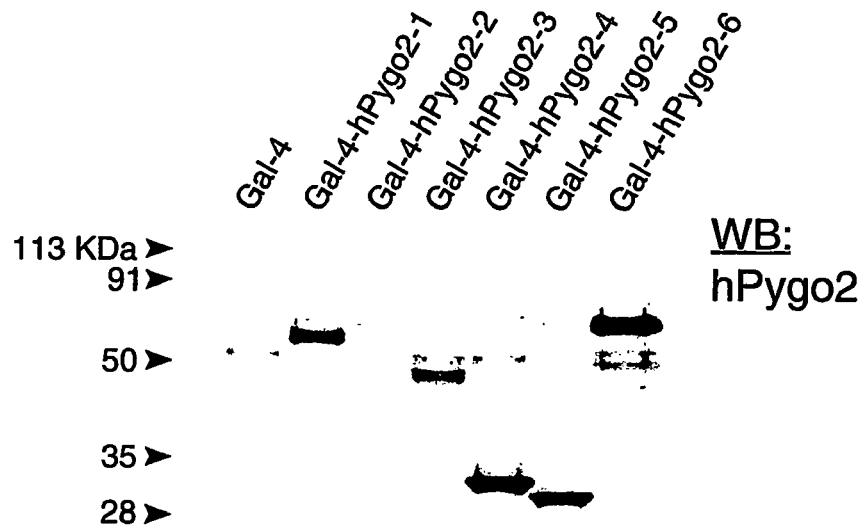
Figure 3C:
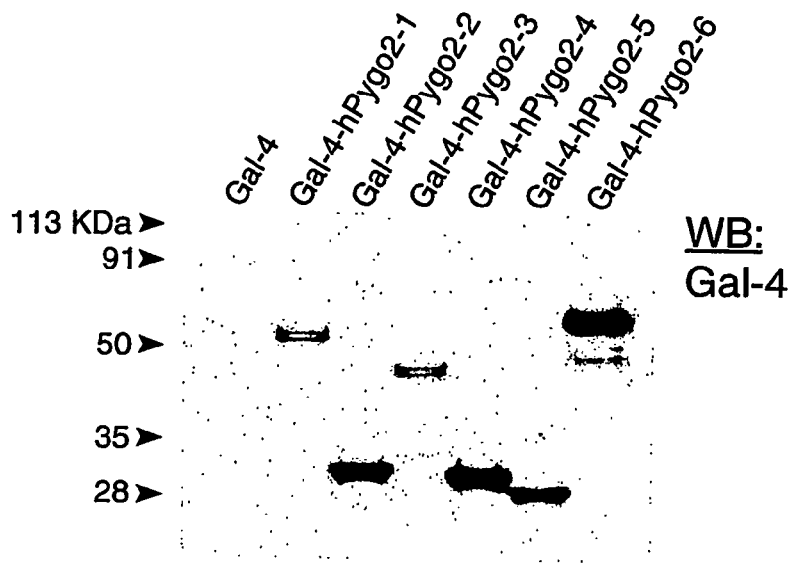
Figure 3D:
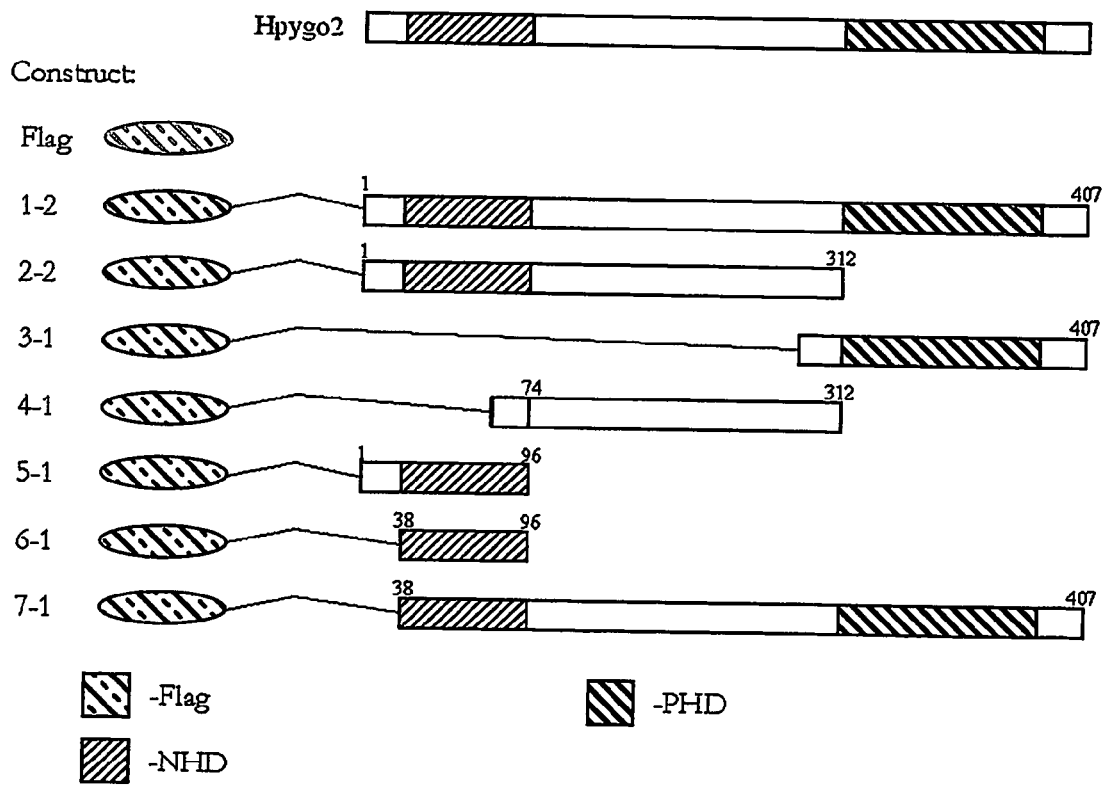
Figure 3E:
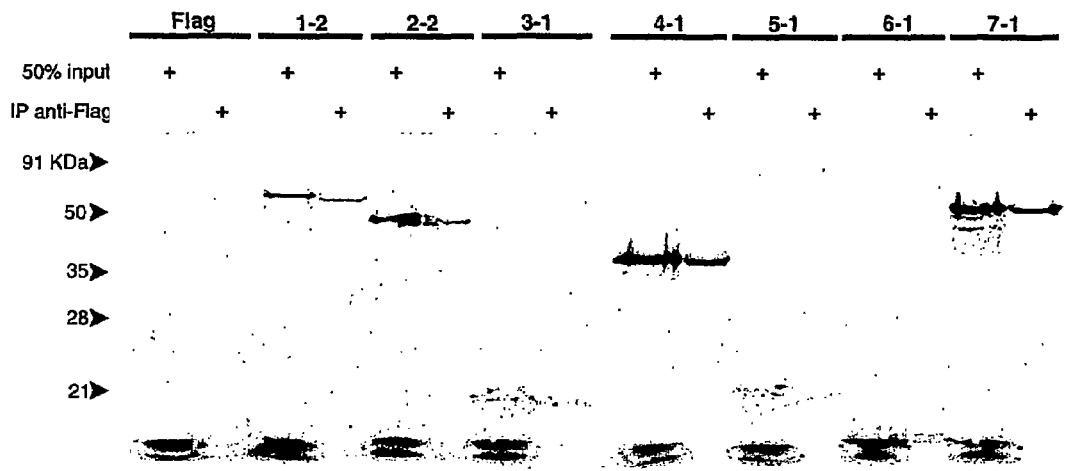

FIGS. 3(d) and (e) show similar experiments conducted using fusions to Flag peptide.

Figure 3F:
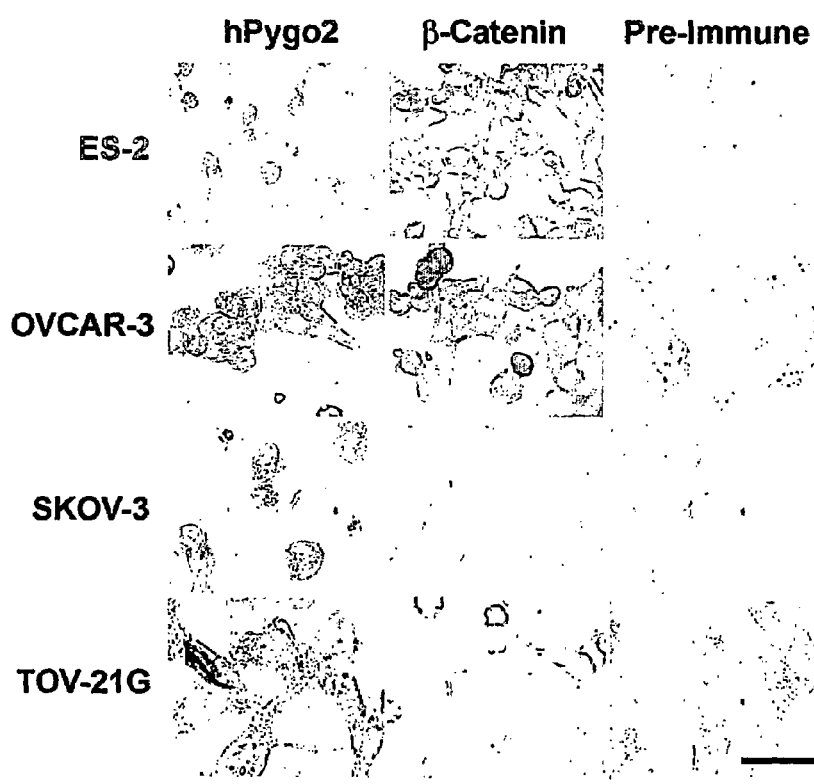

FIG. 3(f) depicts immunocytochemical analyses of four OvCa cell lines using anti-hPygo2 antibodies and beta-catenin. The results show that all four lines express hPygo but only two express beta-catenin. Thus Pygopus is more closely correlated with malignant epithelial ovarian cancer cells than other wnt signaling components.

(3) Overexpression of hPygo2 in EOC Cell Lines

We initially surveyed β-catenin and GSK-3β expression in six malignant EOC cell lines (OV-90, NIH-OVCAR-3, TOV-21G, TOV-112D, SK-OV-3 and ES-2) to determine the role of canonical Wnt signaling in this malignancy (FIG. 4a). β-catenin was overexpressed in TOV-112D cells but underexpressed or not expressed in the other lines, relative to normal ovarian surface epithelial (OSE) cells. Also, only two EOC lines, TOV21G and SKOV-3, expressed the activated, phosphorylated form of GSK3-β. Thus, β-catenin expression and that of its regulatory factor, GSK3-β is variable in these EOC cell lines.

Figure 4A:
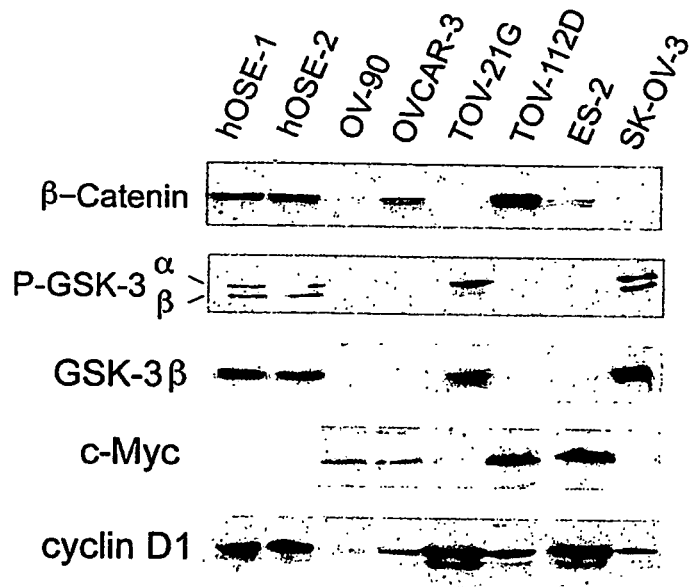
FIG. 4: Consistent overexpression of hPygo2 in epithelial ovarian cancer.
(a) Western analysis of normal (hOSE-1, -2) and malignant cell lines indicates that expression of Wnt signaling components is variable across different cell lines.
(b) expression of hPygo2 RNA on northern blots (NB) and protein on immunoblots (IB) indicates that they are highly overexpressed in malignant EOC cell lines. In vitro synthesized hPygo2 (IVT) was used as a positive control.
(c) hPygo2 protein expression in tumors was graded according to intensity and frequency of tumor cell nuclei stained with hPygo2 antiserum as compared to underlying stromal cells. Non-malignant ovarian epithelial adenomas are negative (−) for hPygo2. Staining of malignant tumors ranged from weak (+) to moderate (++) to strong (+++).
(d) Examples of hPygo2 and β-catenin expression in adjacent tumor sections. Upper pair shows strong nuclear staining of hPygo2 coincident with weak nuclear and moderate cytoplasmic β-catenin staining. Lower pair indicates coincident moderate hygo2 nuclear staining and negative β-catenin staining.
Figure 4B:
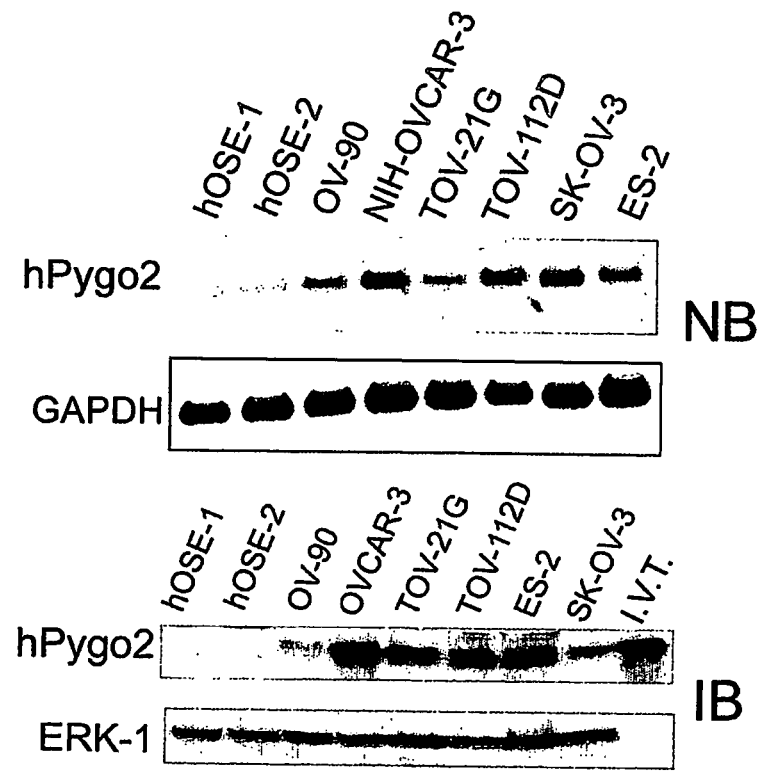

Deregulation of the Wnt pathway in cancer results largely from inactivating mutations in genes encoding β-catenin regulatory factors, or activating mutations in β-catenin itself. In either case, the result of pathway hyperstimulation is an increase in expression of target genes involved in cell cycle progression, including cyclin D1 and c-myc. We did not, however, find consistent coordinate expression of β-catenin with these targets across the EOC lines (FIG. 4a). This lack of correlation in the expression of Wnt pathway components upstream and downstream of Pygopus does not support a general role for canonical Wnt signaling in EOC, so we determined whether this inconsistency also was true for hPygo2. In contrast to the other components, hPygo2 mRNA and protein (FIG. 4b) were overexpressed in every EOC cell line we examined. The levels of hPygo2 mRNA were significantly higher in the cancer cell lines relative to that of normal surface epithelial cells. In addition, while hPygo2 protein was very highly expressed in the cancer cell lines, it was undetectable in the normal cells. These observations suggested that overexpression of Pygopus is a characteristic of EOC.

(4) Pygopus, but not β-catenin is Consistently Over-Expressed in Patient Tumors

Figure 4C:
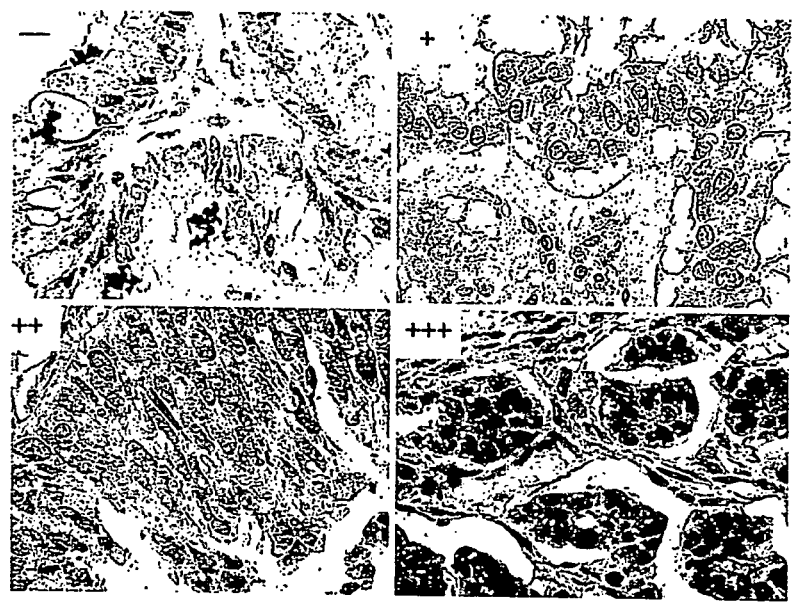
Figure 4D:
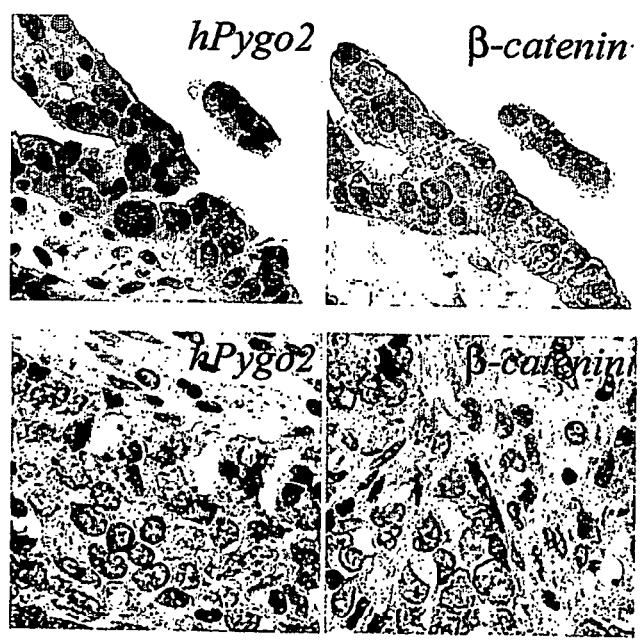

To assess the involvement of Pygopus in disease, we determined the in situ expression of hPygo2 protein in 125 tumors from archived surgical samples. We semi-quantitatively assessed expression based on intensity and percentage of tumor cells stained in both the cytoplasm and nuclei (FIG. 4c). We looked at all EOC tumor subtypes, including serous, mucinous, clear cell, endometrioid, and undifferentiated but the majority, as expected, were of the serous subtype. hPygo2 was not expressed in the nuclei of benign tumors such as endometriosis (data not shown) or was very weakly expressed in non-invasive tumors such as benign cystadenomas (FIG. 4c). On the other hand, 82% of the tumors with a pathological diagnosis consistent with malignant EOC had moderate to strong nuclear accumulation of hPygo2 protein (Table 3) and the staining occurred exclusively in tumor cells but not in the surrounding stroma. Fewer EOC tumors displayed strong cytoplasmic staining and there was no preferential expression of hPygo2 in any tumor subtype. These analyses are consistent with a role for Pygopus in malignant disease.

We also compared β-catenin expression with hPygo2 in adjacent sections from 87 of the 125 tumor specimens from patients diagnosed with malignant EOC collected above (FIG. 4c, Table 4). Eighty-four, or 97% of the tumors stained positive for nuclear hPygo2. Of these, only 8 (9%) of the tumors also stained for nuclear β-catenin. More than half (56%), or 49 of the tumors stained positive for cytoplasmic β-catenin and of these, 47 (54%) stained positive for nuclear hPygo2. None of the tumors stained exclusively for nuclear β-catenin while only 2 tumors had cytoplasmic P-catenin staining without any hPygo2 staining. Only one tumor did not stain for either protein. These observations indicated that the high frequency of excess nuclear accumulation of hPygo2 is largely unaccompanied by nuclear staining of β-catenin in EOC tumors.

(5) Antisense Oligonucleotides and siRNA Specifically Target hPygo2 for Knockdown The high frequency of expression of hPygo2 we observed relative to β-catenin in tumors and cell lines, suggested that Pygopus has a more generalized role in EOC and may therefore be an important therapeutic target.

We used phosphorothioated antisense oligonucleotides (ON) to knockdown hPygo2 in EOC cell lines. We identified antisense oligonucleotides capable of knocking down hPygo2 expression. FIG. 3(g) maps antisense oligonucleotides designed against the full hPygo2 cDNA sequence, avoiding conserved sequences such as the NHD and PHD domains. In FIG. 3(h), antisense oligonucleotides were transfected into HeLa cells at a concentration of 250 nM. RNA was extracted 24 hours later and RT-PCR analysis was performed to assess the relative knockdown of hPygo2 RNA levels. Densitometry was performed, standardizing the relative hPygo2 levels to the relative GAPDH levels. RT−, negative control, without reverse transcriptase.

TABLE 3

Immunohistochemical nuclear and cytoplasmic staining of hPygo2 in EOC tumors distributed by tumor subtype. Numbers in parentheses indicate percentages of totals shown in bottom row.

| | | Tumor Subtype | | | | | | |
| --- | --- | --- | --- | --- | --- | --- | --- | --- |
| | | Benign | Mucinous | Endometrioid | Serous | Clear cell | Undifferentiated | Total |
| Nuclear | − | 7(100) | 3(21) | 0 | 2(2) | 0 | 0 | 12(10) |
| | + | 0 | 1(7) | 1(12) | 8(9) | 0 | 0 | 10(8) |
| | ++ | 0 | 7(50) | 5(63) | 46(53) | 4(80) | 3(75) | 65(52) |
| | +++ | 0 | 3(21) | 2(25) | 31(36) | 1(20) | 1(25) | 38(30) |
| Cytoplasmic | − | 5(72) | 4(29) | 0 | 12(14) | 0 | 0 | 21(17) |
| | + | 0 | 6(43) | 5(63) | 53(61) | 5(100) | 1(25) | 70(56) |
| | ++ | 1(14) | 3(21) | 3 | 21(24) | 0 | 2(50) | 30(24) |

TABLE 3-continued

Immunohistochemical nuclear and cytoplasmic staining of hPygo2 in EOC tumors distributed by tumor subtype. Numbers in parentheses indicate percentages of totals shown in bottom row.

| | | | Tumor Subtype | | | | |
|---|---|---|---|---|---|---|---|
| | Benign | Mucinous | Endome-trioid | Serous | Clear cell | Undiffer-entiated | Total |
| +++ | 1(14) | 1(7) | 0(37) | 1(1) | 0 | 1(25) | 4(3) |
| Total | 7(100) | 14(100) | 8(100) | 87(100) | 5(100) | 4(100) | 125(100) |

TABLE 4

Distribution of EOC tumors based on nuclear and cytoplasmic β-catenin staining in relation to nuclear staining of hPygo2.

| | | Nuclear hPygo2 | | | | |
|---|---|---|---|---|---|---|
| | | − | + | ++ | +++ | Total |
| Nuclear β-catenin | − | 3 | 8 | 43(90) | 25(93) | 79(91) |
| | + | 0 | 1 | 4(8) | 1(4) | 6(7) |
| | ++ | 0 | 0 | 1(3) | 1(4) | 2(2) |
| Cytoplasmic β-catenin | − | 1 | 4 | 22(46) | 11(41) | 38(44) |
| | + | 2 | 3 | 21(44) | 11(41) | 37(43) |
| | ++ | 0 | 2 | 5(10) | 5(19) | 12(14) |
| Total number of tumors | | 3 | 9 | 48(100) | 27(100) | 87(100) |

β-Catenin staining was assessed as either negative (−), weak (+) or moderate to strong (++). Numbers in parentheses indicate percent of totals shown in bottom row.

Of the 10 Ons spanning hPygo2 and the eight ONs spanning the length of the coding region of hPygo2 (Table 2; FIGS. 3(g) and (h)), three significantly knocked down endogenous hPygo2 (Hpy5, Hpy8 and Hpy10), the most effective one of which we used for experiments (Hpy5).

Figure 5A:
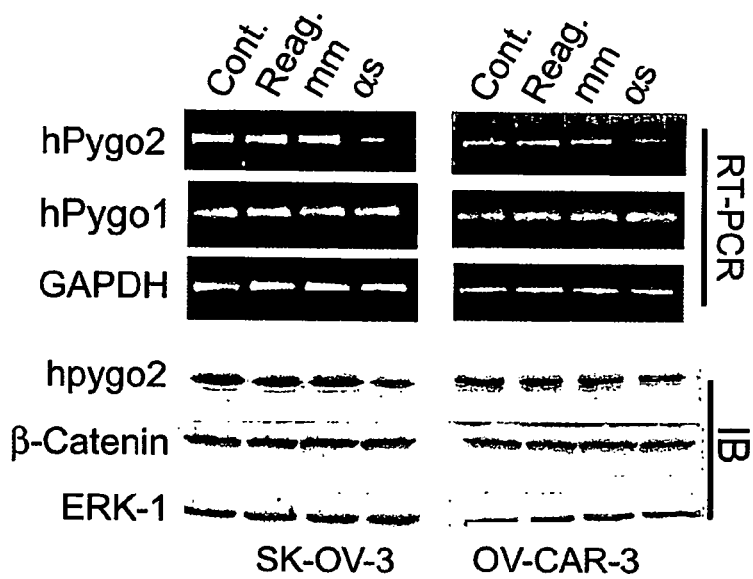
FIG. 5: Demonstration of knockdown of protein in SK-OV-3 and OV-CAR-3 EOC cell lines.
(a) Cells were transfected with either antisense hPygo2 (αs) or mismatched control (mm) oligonucleotides and compared to untransfected (Cont.) or mock transfected (Reag.) cells. Expression of either hPygo1 or β-catenin was unaffected indicating specificity of the ON. GAPDH expression was used as a loading control for RT-PCR and ERK-1 for immunoblots.
(b) Both SK-OV-3 and OV-CAR-3 cells were transfected with β-catenin-specific siRNA and two siRNAs (Hpy2A, D) for hPygo2. Expression of hPygo2 and β-catenin was assayed by immunoblot, using ERK-1 as a loading control and in vitro synthesized hPygo2 (IVT) was used as a positive.

Both hPygo2 mRNA and protein levels were significantly reduced by the antisense ON as compared to controls, without affecting the expression of hPygo1 RNA or β-catenin protein (FIG. 5a). Of the two cell lines tested, the ON reduced endogenous hPygo2 protein by about 40% in SK-OV-3 cells while there was a reduction by approximately 30% of the endogenous hPygo2 level in OVCAR-3 cells (FIG. 5a).

Figure 5B:
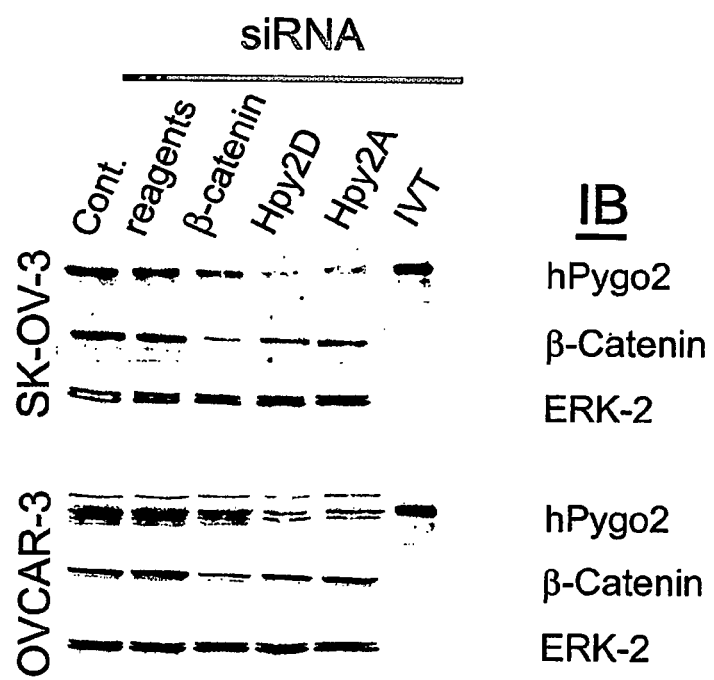

We next tested small interfering RNAs (siRNA) to provide an alternative means to knockdown hPygo2. Out of five siRNA sequences, two (Hpy2A and Hpy2D) were effective in reducing hPygo2 levels to 50% (Hpy2A) and 32% (Hpy2D) of the mock transfected control levels in both OVCAR-3 and SK-OV3 cells (FIG. 5b). This reduction was specific to hPygo2, as the levels of β-catenin were not significantly different from that of cells transfected with the negative control siRNA. The requirement of β-catenin was also tested using commercially available anti-β-catenin siRNA, which caused a significant reduction of endogenous β-catenin to less than 10% in both cell lines, while not affecting the levels of hPygo2. These experiments indicated that both antisense ON and siRNA are effective ways to knockdown hPygo2 in EOC.

(6) hPygo2 and β-Catenin do not Colocalize

Figure 6A:
FIG. 6: Visualization of hPygo2 and β-catenin knockdown in EOC cell lines by confocal microscopy.
Control transfected SK-OV-3 cells shows b-catenin associated primarily with the plasma membrane while hPygo2 is exclusively in the nucleus.
(b) Cells stained with pre-immune hPygo2 serum.
(c) SK-OV-3 cells transfected with mismatched control ON.
(d) SKOV-3 cells transfected with antisense hPygo2 ON.
(e) Control OV-CAR-3 cells with plasma membrane-associated β-catenin and nuclear hPygo2.
(f) & (j) OV-CAR-3 cells stained with pre-immune serum.
(g) OV-CAR-3 cells transfected with mismatched ON.
(h) OV-CAR-3 cells transfected with with antisense hPygo2 ON.
(i) Non-specific siRNA does not affect β-catenin or hPygo2 expression in OV-CAR-3 cells.
(k) Knockdown of β-catenin in OV-CAR-3 cells does not affect hPygo2 expression.
(l) Knockdown of hPygo2 in OV-CAR-3 cells. Arrowhead indicates a single cell with normal hPygo2 expression.
Figure 6B:
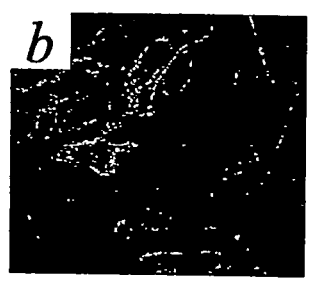
Figure 6C:
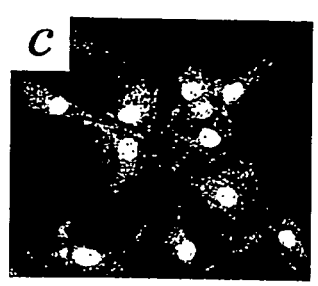
Figure 6D:
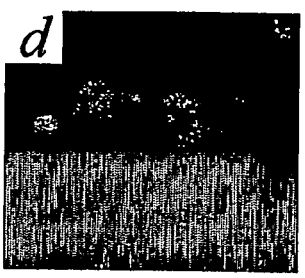
Figure 6E:
Figure 6F:
Figure 6G:
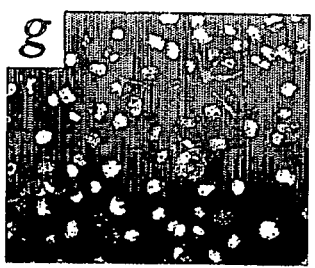
Figure 6H:
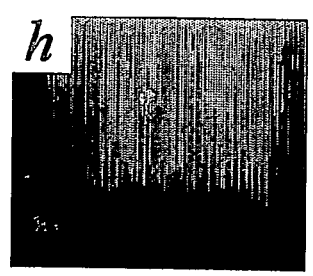
Figure 6I:
Figure 6J:
Figure 6K:
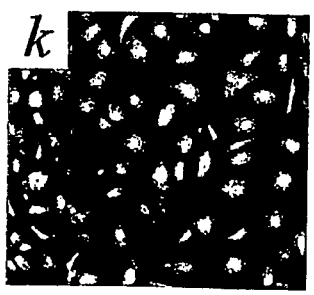
Figure 6L:
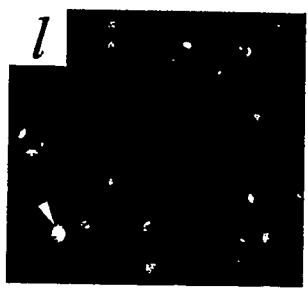

Based on our immunoblot data (FIG. 4a), β-catenin is expressed in both SKOV-3 cells and OVCAR-3 cells. Demonstration of nuclear co-localization of hPygo2 with β-catenin, therefore, would provide evidence that hPygo2 is involved in canonical Wnt signaling in EOC cell lines. Studies using conventional fluorescence microscopy may be confounded by high autofluorescence levels and low resolution associated with conventional fluorescence microscopy. So we used confocal microscopy to unambiguously visualize the normal expression and knockdown by ONs and siRNA of hPygo2 and β-catenin in SK-OV-3 and OVCAR-3 EOC cell lines in situ (FIG. 6). In the colour version of this Figure, not shown, red fluorescence indicates expression of b-catenin and green fluorescence indicates hPygo2 expression). In the untreated (FIG. 6a, e, i) and control transfected (FIG. 6c, g) cells, β-catenin was localized to the plasma membrane, whereas hPygo2 was always concentrated in nuclei. In cells transfected with both antisense ONs and siRNA specific for hPygo2, however, the concentration of hPygo2 in nuclei was noticably reduced (FIG. 6d, h, l). In these cases β-catenin was still often expressed and continued to be localized at points of cell-to-cell contact (FIG. 6d, h). Interestingly, knockdown of β-catenin in the SK-OV-3 cells resulted in a slight dispersion of hPygo2 protein from nuclei, but the cells clearly continued to overexpress hPygo2 (FIG. 6k). Thus, the lack of co-localization of hPygo2 and β-catenin suggests that the activities and functions of these proteins are not coupled in EOC cell lines.

(7) Requirement of hPygo2 for EOC Cell Survival

Figure 7A:
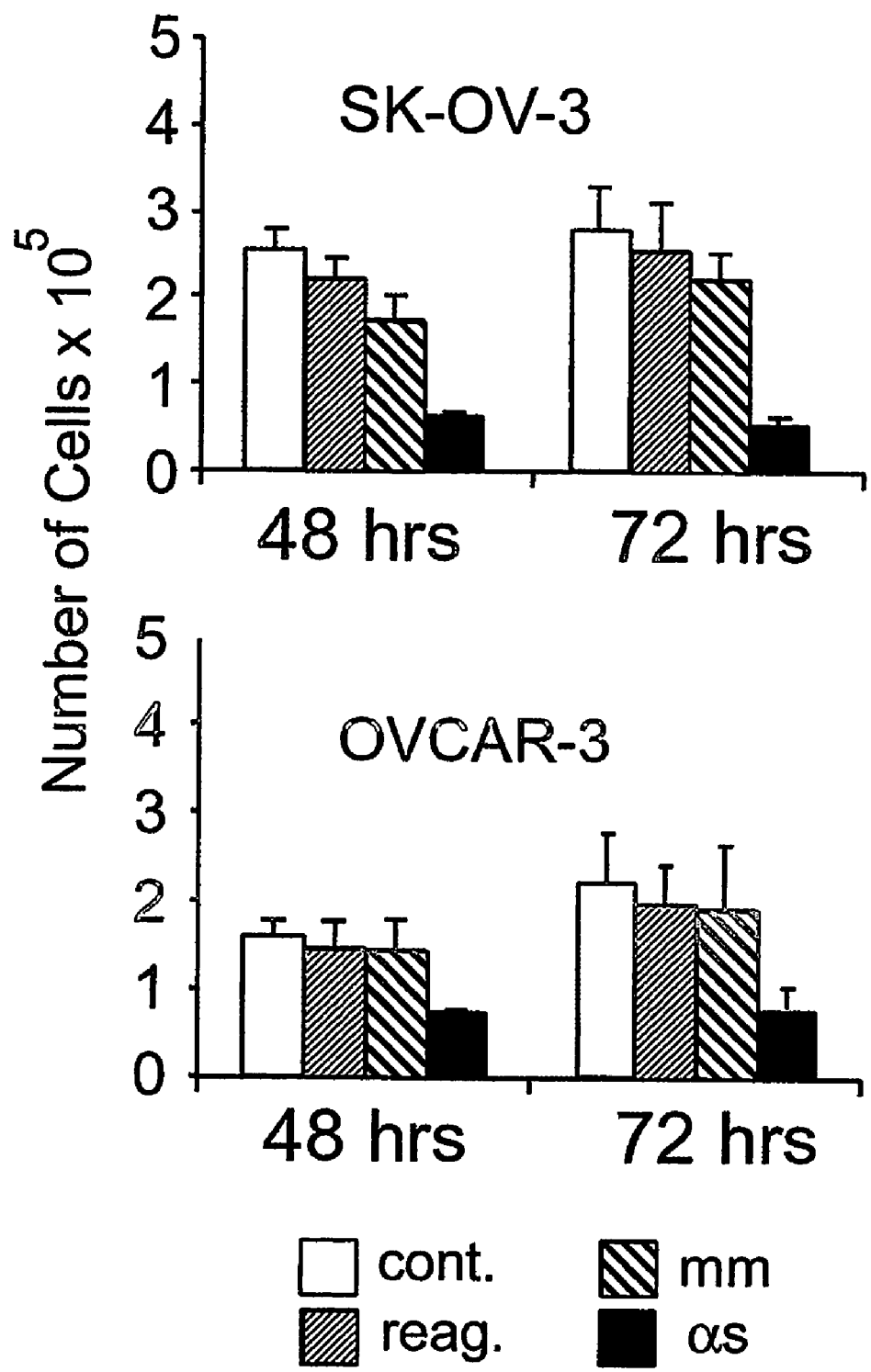
FIG. 7: hPygo2 is required for EOC cell survival
(a) Growth assays of SK-OV-3 and OV-CAR-3 cells transfected with antisense hPygo2 (αs) and mismatched (mm) control ONs, 48 and 72 hours after transfection.
(b) DNA content of SK-OV-3 cells transfected with β-catenin and hPygo2 siRNA compared to control and mock transfected (reagents) cells indicates a higher proportion of sub-G1 cells in hPygo2-depleted cells, as measured by the areas under the curves.

We established the cellular requirement for Pygopus after knockdown of hPygo2 and β-catenin in SKOV-3 and OVCAR-3 cell lines. Significantly, both of these EOC lines underwent growth reduction 48 and 72 hours after antisense hPygo20N transfection as compared to untreated cells and cells transfected with control ONs (FIG. 7a). hPygo2 siRNA also caused marked reduction in cell numbers of both cell lines 48 and 72 hours post-transfection (FIG. 7b). β-catenin siRNA, on the other hand, caused a significant reduction in OVCAR-3 but only a slight reduction in SK-OV-3 cell numbers. Interestingly, knockdown of β-catenin in SK-OV-3 cells resulted in a modest reduction in hPygo2 and a consequent partial decrease in cell numbers. Whether or not the effects on cell growth in this instance are due to the loss of β-catenin or partial reduction in hPygo2 is unclear but it is possible that EOC cell survival is dependent on the expression of hPygo2, which in turn is partially dependent on Wnt signaling, consistent with previous findings that TCF/LEF is a Wnt target.

Figure 7B:
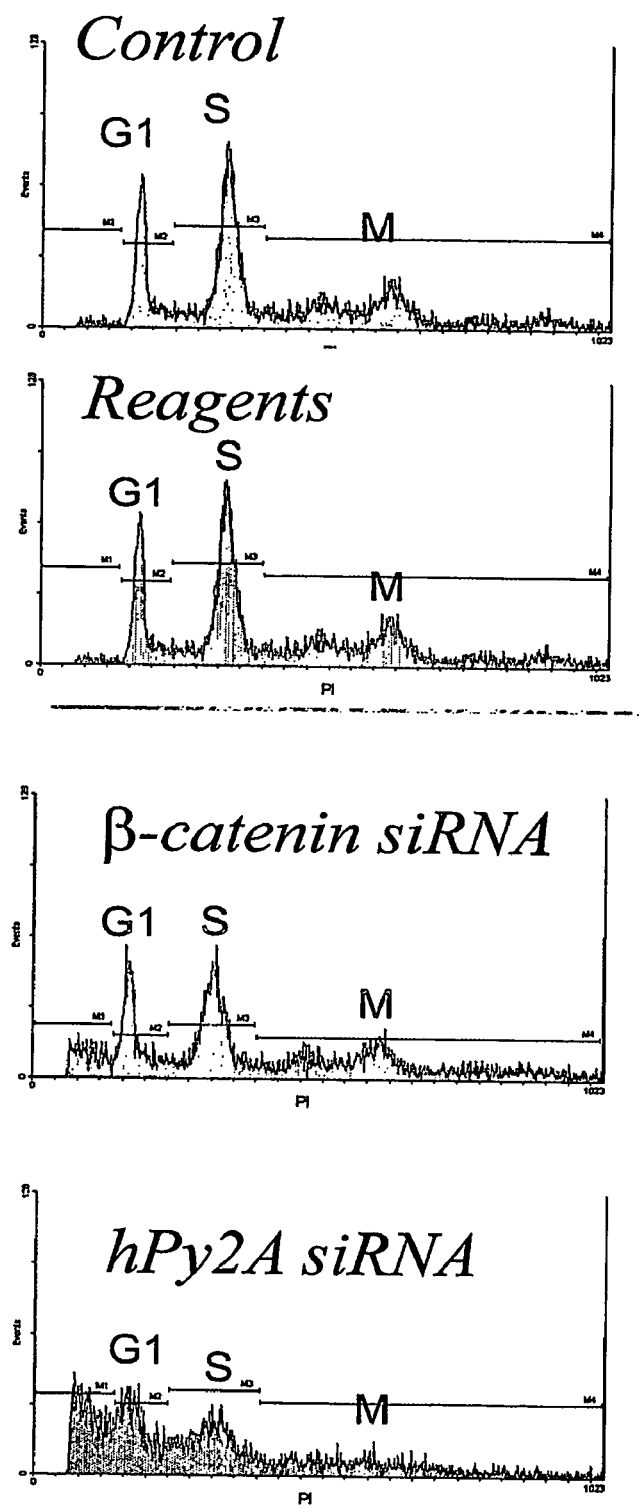
Figure 8A:
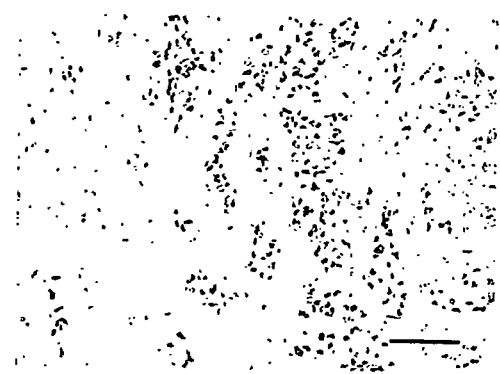
FIG. 8: Immunohistochemical analysis of hPygo2 in breast tumors.
(a) Normal breast tissue negatively stained for hPygo2.
(b-d) Infiltrating ductal carcinomas stained with hPygo2. Weak cytoplasmic hPygo2 staining (b), strong cytoplasmic hPygo2 staining (c), Strong nuclear and moderate cytoplasmic hPygo2 staining. Scale=100 micrometers.
Figure 8B:
Figure 8C:
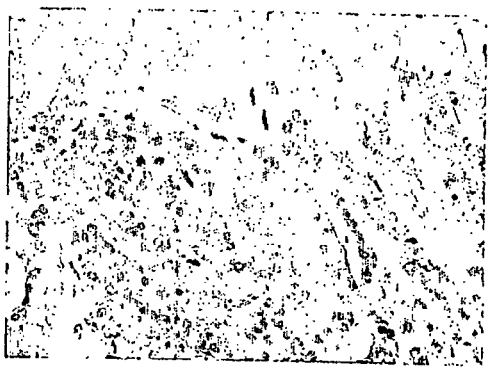
Figure 8D:
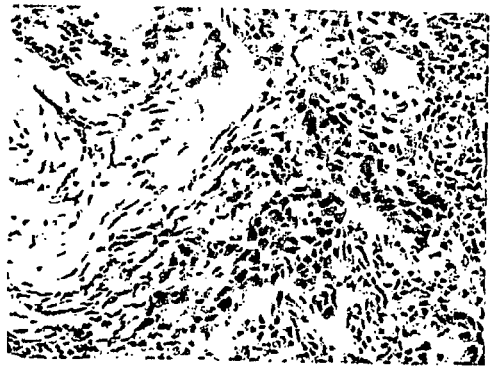

The loss of EOC cell numbers could result either from the siRNA-transfected cells undergoing cell death or from cell cycle arrest. Accumulation of cells with DNA content less than that of cells in G1, for instance, would signify loss of DNA, resulting from death, while a reduction in cell numbers in M and S-phase would indicate growth arrest. To distinguish these possibilities, we processed cells in which hPygo2 or β-catenin was knocked down, for fluorescence activated cell sorting (FACS) using propidium iodide to monitor DNA content (FIG. 7b). After 48 hours, untreated and control treated cells showed modest differences in the distribution of cells in G1, S-phase and M-phase of the cell cycle. There was a significant increase in the fraction of sub G1 phase cells in both SKOV-3 and OVCAR-3 cells treated with hPygo2 siRNA. Consistent with the counting assays, we found that only the OVCAR-3 cells were most sensitive to β-catenin siRNA, while the SKOV-3 cells treated with β-catenin siRNA showed a modest increase in the proportion of sub G1 cells compared to the untreated controls. These findings indicate that removal of hPygo2 from EOC cells causes them to die, indicating a role of Pygopus in EOC cell survival.

(8) Hypothesis on Mechanism

Pygopus was proposed to be dedicated to the canonical Wnt/β-catenin pathway but our results now indicate that it can also function independently of β-catenin in EOC. Pygopus either has non-Wnt activity, therefore, or its sole overexpression in cancer is sufficient to activate Wnt target gene expression, making β-catenin dispensable, perhaps by causing localized chromatin remodeling effects either alone, or in combination with other partnering proteins. Other non-canonical Wnt components, such as Plakoglobin (γ-catenin) can bind to TCF/LEF and therefore might be recruited by Pygopus. Alternatively, Pygopus may be involved in other non-canonical Wnt processes such as the Wnt/Ca2+ and planar cell polarity (PCP) pathways that are important for embryogenesis, but not yet defined in cancer. These alternatives, however, do not preclude the possibility that the interaction between overexpressed Pygopus and other Wnt components may be still intact in the absence of β-catenin and may be sufficient for Wnt target gene expression.

We have found that hPygo2 knockdown suppresses the growth of breast (MCF-7), two additional ovarian (TOV-112D, TOV21G) and cervical (HeLa) cancer cell lines (see below) supporting the hypothesis that Pygopus plays a generalized role in malignancy.

The high frequency of expression of Pygopus in malignant tumors, coupled with its requirement for EOC cell survival suggests that inhibition of Pygopus activity is a feasible strategy against cancer.

EXAMPLE 2

Pygopus is a Diagnostic and Therapeutic Target in Breast Cancer, as Well as Ovarian and Cervical Cancer (1) Detailed Protocols (a) hPygo2 clones and antibody production: The region encoding amino acids 89-328 of hPygo2 lacking both the NHD and PHD conserved sequences was PCR amplified (F: 5'-GCATCCAACCCTTTTGAAGATGAC SEQ ID NO:22; R: 5'-TCAGCCAGGGGGTGCCAAGCTGTTG SEQ ID NO:23) from I.M.A.G.E. Consortium (LLNL) hPygo2 cDNA clones (CloneIDs: 41570072 and 3627860) obtained from Incyte Genomics Inc. and ligated into pGEX-4T1 (Amersham). Purified proteins were synthesized and isolated from BL-21 (RIL) cells (a gift from Dr. G. Paterno) using the GST Gene Fusion System (Amersham), as per manufacturers protocol. Preimmune serum was collected from rabbits (Charles River Laboratories) which were subsequently injected with 500 μg of purified GST-hPygo2 fusion protein resuspended in phosphate buffered saline. Serum collection and boosting was performed as described (Ryan P J and Gillespie L L. (1994). *Dev Biol*, 166, 101-111).

(b) Northern blotting and RT-PCR: Total RNA was extracted from cell lines using the RNA extraction kit Nucleospin™ RNA II Kit (Clontech). Northern blot analysis was performed as previously described (Lake and Kao 2003) using radioactively labeled probes generated by random labeling (Prime-a-Gene; Promega) of the PCR product of hPygo2 used in antibody preparation. Blots were washed at high stringency (60OC in 0.1% SDS and 0.1×SSC) and reprobed with GAPDH (pTRI-GAPDH; Ambion) under the same hybridization conditions.

Semiquantitative RT-PCR was performed as previously described (Lake B B and Kao K R. (2003). *Dev Biol*, 261, 132-148) using hPygo2 oligonucleotide primers described above. Primers for hPygo1 (Kramps et al. (2002). *Cell*, 109, 47-60) (F: 5'-GCCACGACAACCAAGAGGTG SEQ ID NO:24; R: 5'-CCAGTACAGATCCGATGAAACC SEQ ID NO:25), Bcl-9 (Willis et al. (1998). *Blood*, 91, 1873-1881) (F: 5'-GATGTTGTCCTGGTGTCTTG SEQ ID NO:26; R: 5'-GGTCACGACACTGCAGTGCTC SEQ ID NO:27) and GAPDH (Ju et al. (1995). *Nature*, 373, 444-448) were synthesized by Invitrogen.

(c) Western blotting: Monoclonal and polyclonal β-catenin antibodies were purchased from Santa Cruz Biotechnology, monoclonal β-actin antibodies from Sigma, and Cyclin D1 monoclonal antibodies from BD Biosciences. Total protein from tissue culture cells was extracted in protein sample buffer. As a positive control, in vitro translated hPygo2 protein was prepared using the transcription/translation coupled cell-free system (Promega). Approximately 50 μg of total cell lysate was separated by SDS-PAGE, transferred to nitrocellulose membranes (Hybond-ECL™; Amersham) and visualized by enhanced chemiluminescence (Amersham). Blots were reprobed with β-actin to confirm equal loading of protein.

(d) Immunocytochemistry and Immunohistochemistry: For immunofluorescence analysis, Hs-574-mg, Bt-474 and Mcf-7 cells were fixed in 4% paraformaldehyde (30 minutes) rinsed in PBS twice and 0.2% triton-X 100/PBS (tPBS) for 10 minutes. Cells were blocked in 10% normal donkey/goat serum prior to an overnight incubation with primary antibodies in 1.5% normal serum/PBS. After a 30 to 40 minute wash in 0.2% tPBS, cells were incubated 30 minutes with secondary antibodies in 1.5% normal sera. For hPygo-2, biotinylated donkey anti-rabbit (Amersham) and for β-Catenin, Cy3 donkey anti-mouse (Jackson ImmunoResearch Laboratories, Inc.) was used. After a 30 to 40 minute wash in 0.1-0.2% tPBS, cells were incubated in streptavidin fluorescein (Amersham) in 1.5% normal sera/PBS for 30 minutes. Cells were washed in 0.1-0.2% tPBS 30 to 40 minutes before mounting in 10% glycerol/PBS or Vectashield™ (Vector Laboratories, Inc.). Images were collected using confocal microscopy (Olympus).

Immunohistochemistry was carried out essentially as previously described (Rorke et al. (2001). Int j Cancer, 95, 317-322). Breast tumor sections were obtained from the Memorial University Division of Laboratory Medicine.

(e) Antisense oligos and siRNA: Antisense oligonucleotides (Invitrogen) against hPygo2 were designed to contain three phosphorothioate bonds at each terminus as indicated by asterisks to enhance nuclease resistance. The sequences used were as follows: hPygo2 antisense oligo; 5'-G*G*C*TGAGCAAATCGTT*G*G*G (Hpy5; SEQ ID NO:9), *Xenopus* Pygo2-specific control oligo; 5'-T*T*T*GCGCCGTTTCTT*C*T*C SEQ ID NO:21, 4 base mismatch oligo; 5'-G*U*C*TGAGCUAATCATT*G*G*T (mismatches underlined; SEQ ID NO:28). All oligonucleotides were designed avoiding G quartets and repeated CG sequences which may result in non-specific antisense effects. β-Catenin siRNA and non-specific control siRNA were purchased as a β-Catenin siRNA/siAB™ (siRNA knockdown). Assay Kit (Upstate). hPygo2 siRNA was synthesized using the (Xeragon-Qiagen) sense sequences:

```
Hpy2A;
5'-r(CGAUGACCAGGAUGCCAUU)dTT-3'    (SEQ ID NO: 15)

Hpy2D;
5'-r(CCAGCCUCUGGGUCAAAAC)dTT-3'.   (SEQ ID NO: 18)
```

(f) Cell culture and transfection: All cell lines, except normal endocervical (HEN) and normal ectocervical (HEC) cell lines (Tsutsumi et al. 1992), were purchased from the American Type Culture Collection. T98G and Sk-N-Sh cells were maintained in Minimal Essential Media (Gibco) supplemented with 10% fetal bovine serum. HEN and HEC cells were maintained in Keratinocyte Serum Free Media (Gibco). All remaining cells were maintained in Dulbecco's modified Eagle's medium supplemented with 10% fetal bovine serum (Gibco).

All transfections utilized Oligofectamine™ (Invitrogen) as per the manufacturer's instructions, replacing the growth media every 24 hours. hPygo2 antisense/control oligonucleotides were transfected to a final concentration of 250 nM and all siRNAs were transfected at a final concentration of 100 nM. siRNA was transfected again 24 hours after the first transfection. For RT-PCR analysis, cells were seeded at a density of $1.5 \times 10^5$ cells/well in six-well plates and were harvested 24 hours after transfection for RNA extraction. For western analysis cells were seeded at a density of $10^5$ cells/well in twelve-well plates and were harvested 48 hours after transfection. For cell growth analysis cells were seeded in triplicate at a density of $7.5 \times 10^4$ cells/well in twelve-well plates, and were counted 48 and 72 hours after transfection using trypan blue exclusion (Sigma) with a hemacytometer.

(2) Pygopus is Expressed in Malignant Breast Cancer

The expression of hPygo2 in archived surgical breast tumor specimens was determined by immunohistochemical analysis using antiserum we developed to react with non-conserved domains of the hPygo2 protein. We obtained 22 archived breast tumor sections and 1 normal breast section and stained them with hPygo2 (FIG. 8). In 14 tumors, there was staining of hPygo2 in malignant cells, but not in the surrounding non-tumor cells. Of the 14 positively stained specimens, 6 had distinct nuclear/cytoplasmic hPygo2 staining, whereas 8 had cytoplasmic hPygo2 staining. hPygo2 could not be detected in the normal breast tissue section. We also obtained 4 lymph node sections from breast tumor patients. Two out of four contained metastatic tumor cells which stained positive for hPygo2, the other two did not contain tumor cells and did not stain with hPygo2. The consistent expression of hPygo2 in the malignant cells of these tumors suggested that Pygopus plays an important role in breast cancer.

Figures 9E, 9F:
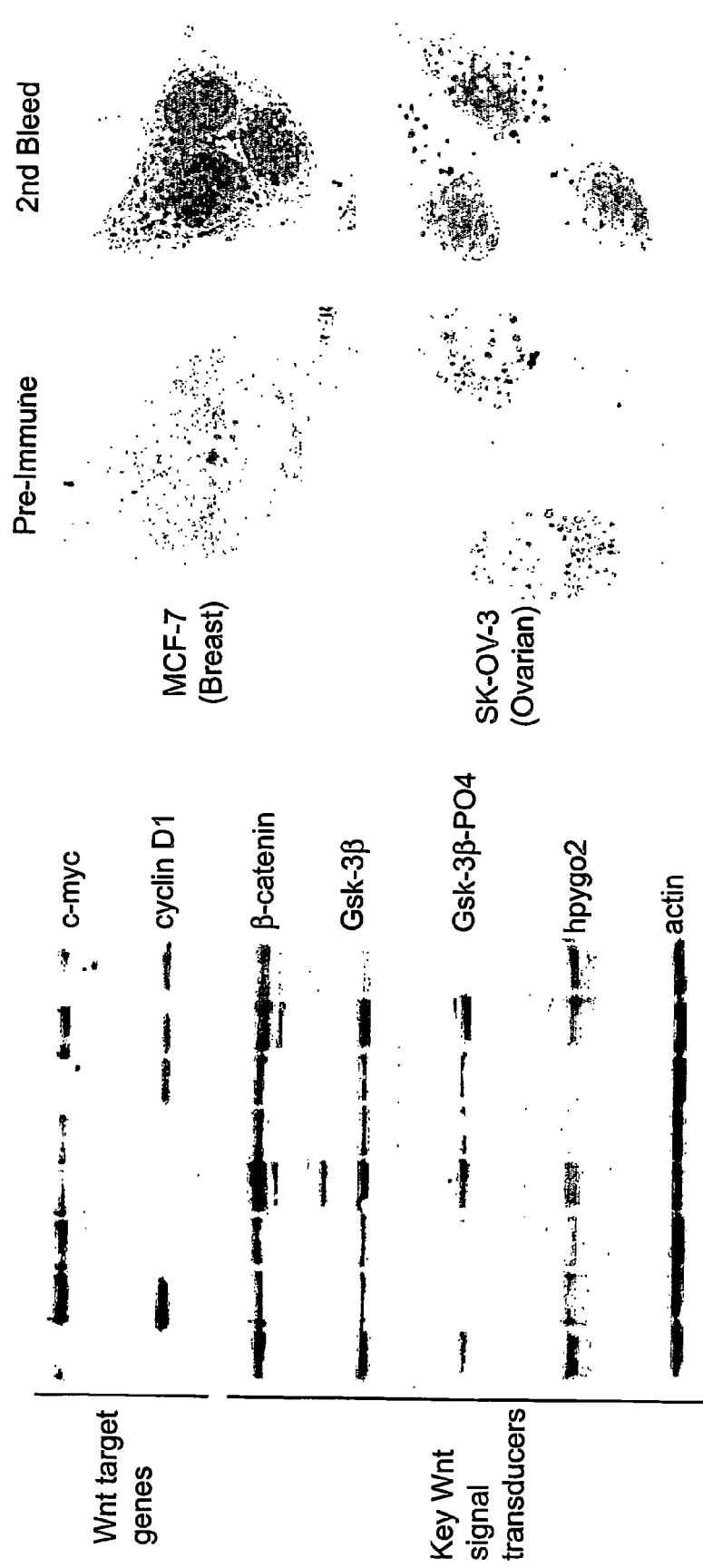
FIG. 9: Expression of hPygo2, β-Catenin and Bcl-9 in cell lines. Levels of RNA and protein were standardized using GAPDH and β-Actin.
(a) Expression of hPygo2 mRNA by northern analysis of total RNA. The positions of the 28s and 18s ribosomal RNAs are indicated.
(b) Immunoblot showing specificity of antibody for the hPygo2 protein. The approximate size of hPygo2 protein is 50 KDa, as indicated by molecular weight markers are shown on the left. In vitro transcribed and translated full length hPygo2 protein (hPygo2) was used as a positive control.
(c) Expression of hPygo2 and β-Catenin by western blot analysis of total cell lysate of the various cell lines used.

To study the role of Pygopus in malignant breast cancer cell lines, the expression of hPygo2 mRNA was determined in the breast cancer cell lines Bt-474 and Mcf-7 and compared to a variety of cell lines derived from normal tissues and other malignancies using northern blot analyses (FIG. 9a). Messages were highly expressed in both ovarian cancer (Sk-Ov-3, Es-2), cervical cancer (HeLa, CaSki), breast cancer cell lines (BT-474, Mcf-7), and normal ectocervical (HEC) cells. Alternatively, hPygo2 mRNA expression was very low or absent in neuroblastoma (T98G, Sk-N-Sh), normal endocervical (HEN) and normal breast (Hs-574) cell line.

The hPygo2 protein migrates to the predicted size of approximately 50 KDa (FIG. 9b). Expression of hPygo2 protein in the cell lines was consistent with the expression of hPygo2 mRNA (FIG. 9c), with higher expression in ovarian, cervical, normal ectocervical and breast cancer cells and lower expression in neuroblastoma, normal endocervical and normal breast cells. Examination of β-Catenin protein expression demonstrated that it very closely resembled that of hPygo2 in most of the cell lines (FIG. 9c). Notably, hPygo2 expression was absent in the normal breast cell line (Hs-574), but was expressed at very high levels in two breast cancer cell lines (Bt-474, Mcf-7).

(3) β-Catenin and hPygo2 do not co-Localize in Mcf-7 and Bt-474 Cells

We next used indirect immunofluorescence and confocal microscopy to determine the subcellular localization of Pygopus and β-Catenin in normal and malignant breast cell lines. Endogenous hPygo2 protein was predominantly localized to nuclei of both breast cancer cell lines analyzed (Bt-474 and Mcf-7) (FIG. 10). In contrast, hPygo2 was predominantly localized to the cytoplasm of the normal breast cell line (Hs-574) (FIG. 10). Unexpectedly, unlike hPygo2, β-Catenin was consistently found in the cytoplasm and associated with the inner cell membrane of the normal and cancer cell lines and only weakly in the nucleus. Therefore, Pygopus and β-Catenin showed a preferential localization to different compartments in the breast cancer cells.

(4) Bcl-9 is not Expressed in Breast Cancer Cell Lines and does not Correlate with Pygopus The interaction of Pygopus proteins with β-Catenin was shown to be mediated by Legless/Bcl-9. The lack of correlation between hPygo2 and β-Catenin subcellular localization, however, would predict that the Wnt/β-Catenin complex is, unexpectedly, uncoupled from hPygo2 in breast cancer. Given that Pygopus interacts with the β-catenin complex through Bcl-9, we assessed the relative expression levels of Bcl-9 by RT-PCR in a variety of cell lines (FIG. 9d). Bcl-9 mRNA was expressed highly in one cervical (HeLa), two ovarian (Sk-Ov-3, Es-2), and two neuroblastoma (T98G, Sk-N-Sh) cell lines, while it was expressed at lower levels in all the other cell lines examined. Surprisingly, there was little correlation in the expression of Bcl-9 with the expression of hPygo2 and β-Catenin. In addition, Bcl-9 was expressed at lower levels in the breast cancer cell lines as compared to the normal breast cells. These results suggest that the function of hPygo2 in breast cancer may not require its interaction with the β-catenin transcription complex.

(5) β-Catenin is not Required for Growth of MCF-7 Cells

Figure 11A:
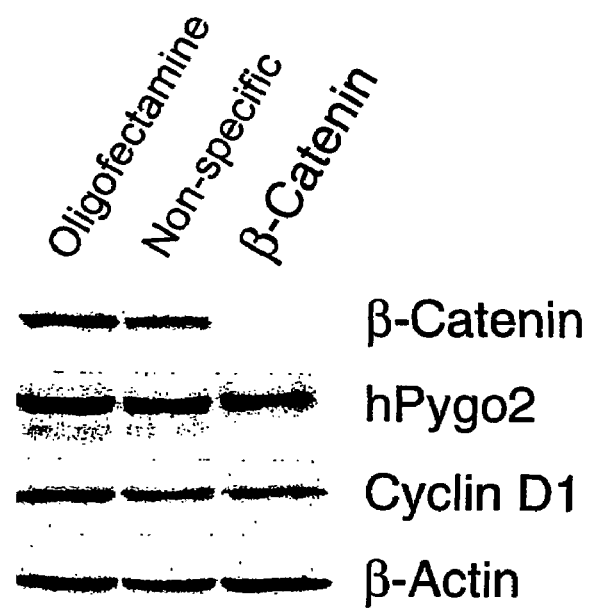
Figure 11B:
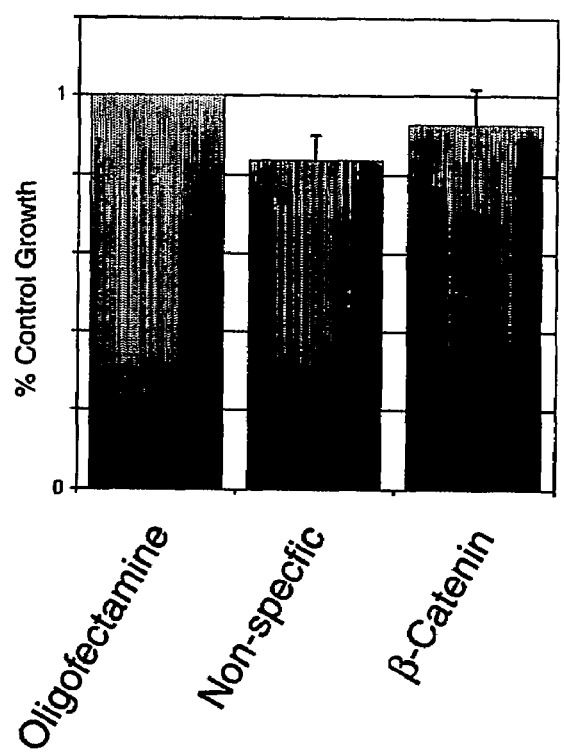

It was previously shown that Mcf-7 cells exhibit Wnt dependent transcription and expression of the Wnt target gene, Cyclin D1. We analyzed, therefore, the requirement of β-Catenin for cell growth in Mcf-7 cells by knocking down its expression with siRNA. Knockdown of β-Catenin with siRNA resulted in a significant decrease of β-Catenin protein, which was not detectable by immunoblotting (FIG. 11a). However, this was accompanied by no apparent change in cell numbers compared to transfection reagent and non-specific siRNA controls (FIG. 11b). Protein levels of both hPygo2 and Cyclin D1 remained unchanged after β-Catenin knockdown compared to a non-specific siRNA (FIG. 11a). These results provide direct evidence that β-Catenin is not required for cell proliferation, nor the expression of the Wnt target gene Cyclin D1 in Mcf-7 cells.

(6) Pygopus is Required for the Proliferation of Mcf-7 Cells

Figure 12A:
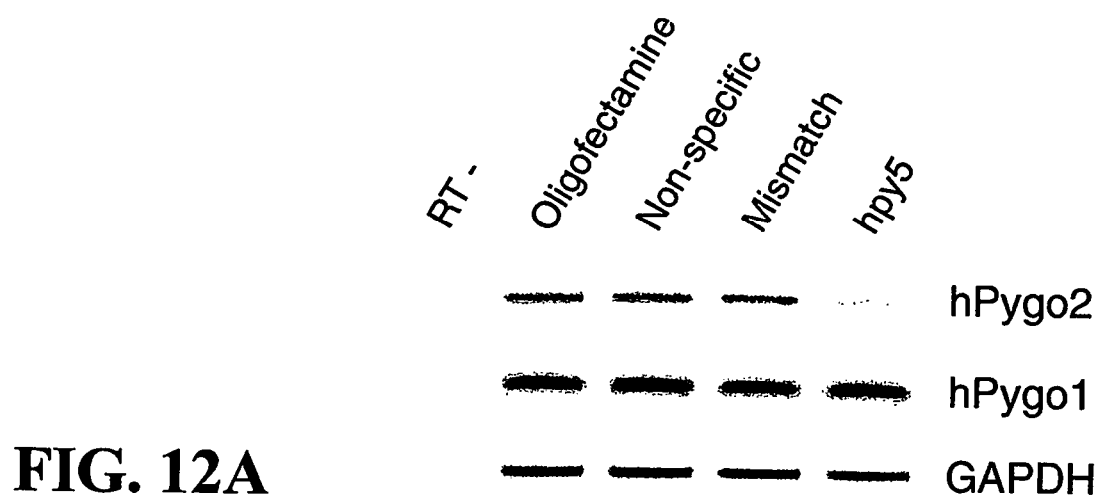
Figure 12B:
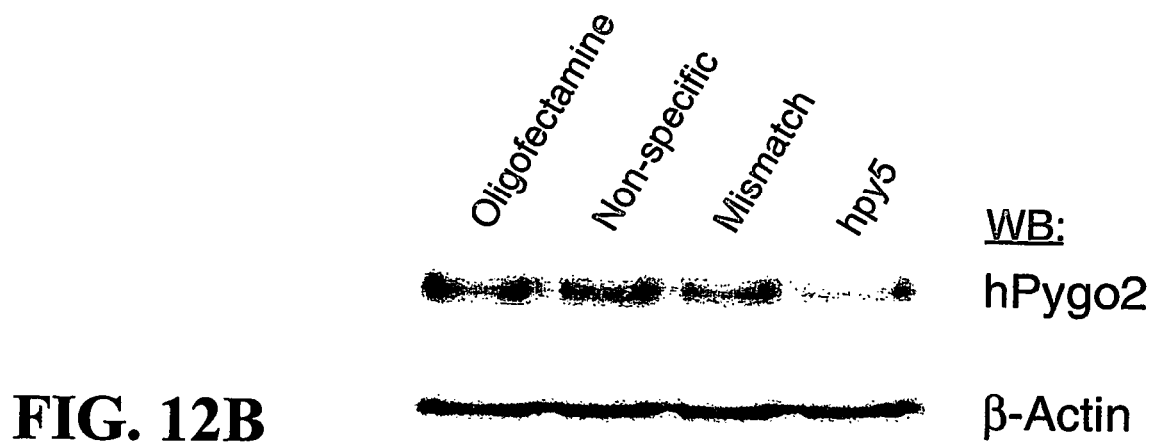

The lack of requirement of β-Catenin for growth of Mcf-7 cells is consistent with our observation that it is predominantly localized to the membrane compartment of Mcf-7 and Bt-474 cells (FIG. 10). On the other hand, since hPygo2 consistently localized to the nucleus it is possible that, in Mcf-7 cells, its requirement for growth is distinct from a function associated with β-Catenin. To test this possibility, we determined the requirement for Pygopus in cell growth in RNA antisense knockdown experiments. In preliminary experiments we designed a vector encoding antisense RNA complementary to hPygo2 that was able to suppress exponential growth of HeLa cells. We also designed a number of antisense ONs specific to hPygo2 mRNA (FIG. 3). A single oligonucleotide (hpy5), which had the greatest ability to knock down hPygo2 mRNA expression, was chosen for further analysis in HeLa cells. We used two controls ONs, one complementary to *Xenopus* Pygo2 (Non-specific) and the other complementary to (hpy5) with a 4 base-pair sequence change (Mismatch). Specific knock down of hPygo2 mRNA expression 24 hrs after transfection of (hpy5) compared to the control ONs was achieved without affecting the expression of the alternate, but related Pygo family member hPygo1 (FIG. 12a). Hpy5 also knocked down endogenous hPygo2 protein to less than 50% of the controls (FIG. 12b).

Figure 13A:
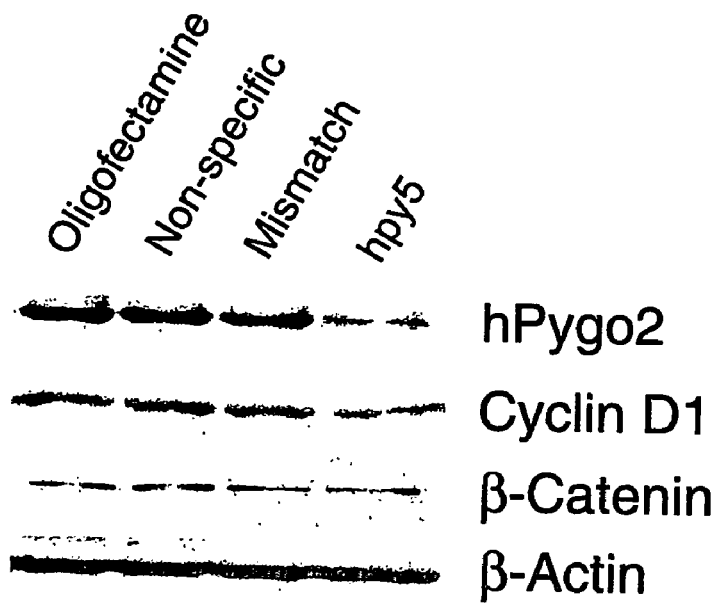
Figure 13B:
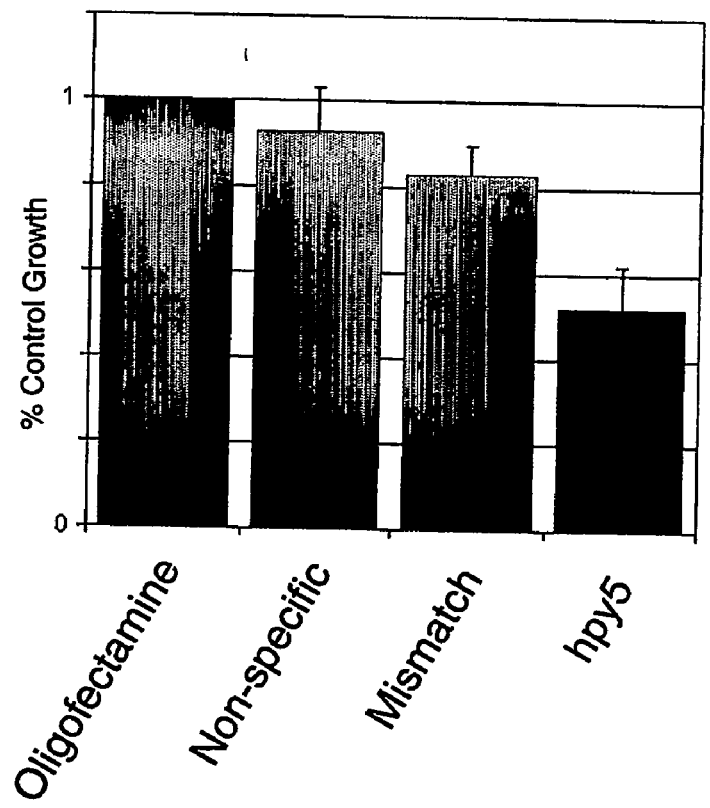

As in the HeLa cells, transfection of the (hpy5) ON into Mcf-7 cells resulted in a significant knockdown in hPygo2 protein levels as compared to the non-specific and mismatch control ONs while β-Catenin levels remained unaltered (FIG. 13a). Most significantly, there was a considerable reduction of Mcf-7 cell growth (FIG. 13b) after transfection with the hPygo-specific ON, as compared to the cells transfected with the non-specific and mismatch control ONs. Cell numbers were reduced to 52%, as compared to 93% with the non-specific control and 83% for the mismatch control as compared to the reagent (Oligofectamine™) control. These results demonstrate that the ability of the hpy5 oligonucleotide to knockdown hPygo2 protein is specific and results in a reduction in cell proliferation. This reduction in cell number was accompanied by a decrease in the cell cycle regulatory protein Cyclin D1 (FIG. 13a), implying that the reduction of cell growth is likely due to cell cycle arrest. These results demonstrate that hPygo2 is required independently of β-Catenin in the growth of Mcf-7 cells.

To confirm that knockdown of hPygo2 by antisense ON results in a decrease of Mcf-7 cell proliferation we used siRNAs specific for hPygo2. Two (Hpy2A and Hpy2D) out of six siRNAs designed against hPygo2 were found to be effective in reducing hPygo2 protein levels (FIG. 14) without effecting β-Catenin protein levels, and were therefore used for further experimentation. Coincident with this reduction in protein levels, we found that both of the siRNAs alone or in combination, caused a significant reduction in Mcf-7 cell numbers (FIG. 14b), therefore confirming our results with the antisense ON.

(7) Hypothesis on Mechanism

Our results demonstrate that Pygopus is overexpressed in breast and other tumors and is required for Mcf-7 cell growth by a mechanism independent of β-Catenin. Together our observations suggest that Pygopus proteins may be overexpressed in cancer and may play an additional role, other than its previously suggested one in mediating the canonical Wnt signal through β-Catenin/Bcl-9.

Our results demonstrated that the expression levels of Pygopus correlated with the expression of β-Catenin but not its only known binding partner, Bcl-9. The breast cancer cell lines used in this study, were previously shown to exhibit Wnt dependent transcription, Cyclin D1 expression, as well as β-Catenin/Tcf complex formation. Therefore, the lack of Bcl-9 expression in the breast cancer cells is unexpected, since Bcl-9 is required to tether Pygopus to the β-Catenin/Tcf complex. It is possible that Pygopus and Bcl-9 are transcriptionally controlled by different regulatory factors and this is why we see differences in the expression patterns.

Mutations in genes encoding components required for Wnt signaling occur at relatively low frequencies in breast cancer, but it has been hypothesized that the overexpression of Wnt signaling components leads to the overexpression of target genes, and thus may contribute to mammary carcinogenesis. For example, β-Catenin has been reported to have nuclear/cytoplasmic staining in approximately 60% of breast tumor tissues in two independent studies. This phenomenon may be due to Wnt independent regulation of β-Catenin, such as the regulation of β-Catenin by fibroblast growth factor and epidermal growth factor family members, as well as the Wnt independent regulation of GSK3.

Interestingly, Pygopus mRNA and protein were highly expressed in the breast cancer cell lines Bt-474 and Mcf-7 compared to Hs-574 normal breast cells and may indicate a requirement for Pygopus in their proliferation. Pygopus is also known to function as a nuclear protein; we have confirmed this by the examination of endogenous subcellular localization. Its concentration in the nuclei of tumor cells but cytoplasmic preference or absence in normal cells. This indicates that Pygopus overexpression and subcellular localization may play a role in malignancy. The display of nuclear Pygopus expression in some patient tumors is consistent with this role.

It has previously has been shown that Wnt signaling, and expression of the Wnt target gene Cyclin D1 is at relatively high levels in Mcf-7 cells compared to a number of other breast carcinoma cell lines. Because, as we have shown, β-Catenin is not required for the expression of Cyclin D1 in these cells, the expression of Cyclin D1 may not be a true indication of Wnt signaling. Indeed, Cyclin D1 expression has been shown to be required for cell growth and regulated by other non-Wnt dependent proteins in Mcf-7 cells, such as Estrogen receptor and Peroxisome Proliferator-activated Receptor γ(PPARγ). The majority of β-Catenin in Bt-474 and Mcf-7 breast carcinoma cells is likely present in a complex with E-Cadherin, rather than constitutively active in the nucleus. Although, in Mcf-7, it is likely that there are low levels of Wnt dependent transcription, this is clearly not sufficient to have an effect on the expression of the Wnt target gene Cyclin D1. Knockdown of Pygopus, on the other hand, resulted in a reduction in expression of Cyclin D1, which is a critical regulator of G1 to S phase transition of the cell cycle. Therefore, the decrease in numbers of Mcf-7 cells by reduction of Pygopus is possibly a result of effects that cause cell cycle arrest.

Inhibition of β-Catenin by ICAT had no effect on HeLa cell growth, consistent with our observations using β-Catenin siRNA in MCF-7 cells. These data suggest that at least in two cancer cell lines, canonical Wnt signaling does not appear to be important for cell growth. These data imply an additional role of Pygopus independently of β-Catenin and Wnt signaling.

Limited studies to date outline the role of Pygopus proteins in Wnt signaling and normal development. The function of hPygo in Wnt signaling has also been addressed in colorectal cancer cells that display constitutive Wnt signaling due to identified mutations in APC and β-Catenin. It is likely, therefore, that Pygopus knockdown, like β-Catenin, might also inhibit the growth of colorectal cells.

Our data indicate that the decrease in Mcf-7 cell proliferation may be a result of cell cycle arrest and that Pygopus may have important roles independent of β-Catenin. These results provide new insight into the function Pygopus in cancer and suggest that Pygopus is a suitable cancer therapeutic target.

EXAMPLE 3

Pygopus is a Diagnostic and Therapeutic Target in Cervical Cancer

FIG. 16 shows knockdown of endogenous hPygo2 using antisense ON in HeLa cervical cancer cells. Reagent control (Oligofectamine™), antisense Xenopus Pygopus2 (non-specific), and four base mismatch (mismatch) controls are indicated. Knockdown of hPygo2 by antisense ON results in a decrease of HeLa cell numbers 48 and 72 hours after transfection. Cell number was assayed for by direct counting with a hemacytometer using trypan blue exclusion. RT-PCR analysis shows specific knockdown of hPygo2 rnRNA without effecting expression of the related Pygo family member, hPygol. RT—is rho negative control, without reverse transcriptase. Western blot analysis shows knockdown of endogenous hPygo2 protein. Levels of cDNA and protein were standardized using GAPDH and beta-Actin. Experiments were performed in triplicate.

EXAMPLE 4

Figure 15A:
Figure 15B:
Figure 15C:
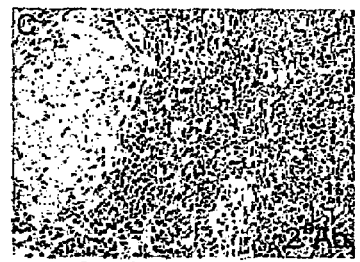
Figure 15D:
Figure 15E:
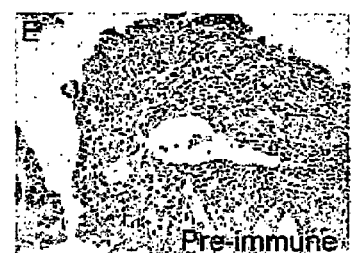
Figure 15F:
Figure 15G:
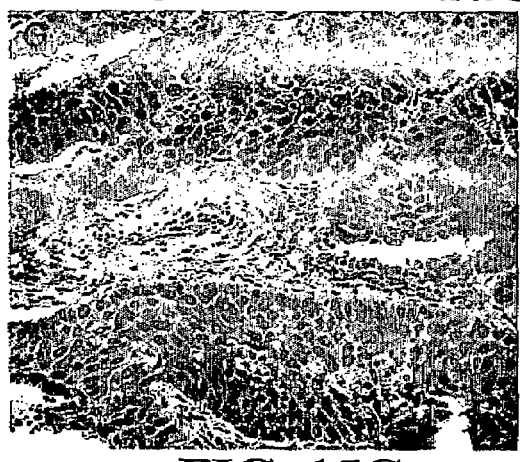
Figure 15H:

Anti-hPygo2 Antibodies Identify Malignant Tumor Cells in Ovarian, Breast and Lung Cancer Anti-hPygo2 antibodies were used in immuno-histochemical analysis to identify malignant tumor cells from ovarian epithelial, breast, and lung cancer. Staining of archived tumors, as determined by a licenced pathologist, using anti-hPygo2 antibodies, indicates that Pygopus is specifically overexpressed in a variety of ovarian epithelial (FIGS. 15 A,C) tumors and in malignant breast (FIG. 15G) and lung cancer (FIG. 15H). Negative staining with pre-immune and secondary antibody alone demonstrates specificity of the antibody.

The invention claimed is

1. A method for determining the presence or absence of a cancer in a patient, wherein the cancer is at least one of cervical cancer, breast cancer, ovarian cancer and lung cancer, the method comprising the steps of:
   (a) determining the level of gene expression of hPygo2 as shown in SEQ ID NO: 1 or 2 in a biological sample obtained from a patient, and
   (b) comparing the level of hPygo2 gene expression in the biological sample to a predetermined cut-off value, wherein the predetermined cut-off value is the level of hPygo2 gene expression in a normal biological sample, to determine whether hPygo2 expression is higher in the biological sample; therefrom determining the presence or absence of cancer in the patient.

2. A method for monitoring the progression of a cancer in a patient, wherein the cancer is at least one of cervical cancer, breast cancer, ovarian cancer and lung cancer, the method comprising the steps of:
   (a) determining the presence or absence of cancer in the patient according to the method of claim 1;
   (b) repeating step (a) using a biological sample obtained from the patient at a subsequent time; and
   (c) comparing the level of hPygo2 gene expression detected in step (b) to the level of hPygo2 gene expression detected in step (a); and therefrom monitoring the progression of the cancer in the patient.

3. The method according to claim 1 wherein the cancer is ovarian cancer, and the biological sample comprises epithelial ovarian cells.

4. The method according to claim 1 wherein the level of hPygo2 gene expression is determined by the amount of hPygo2 protein as shown in SEQ ID NO: 2.

5. The method according to claim 1 wherein the cancer is breast cancer, and the biological sample comprises mammary cells.

6. The method according to claim 1 wherein the cancer is cervical cancer, and the biological sample comprises cervical cells.

7. The method according to claim 4 wherein the level of hPygo2 protein is determined using an antibody or a fragment thereof that binds specifically to hPygo2 protein.

8. The method according to claim 6 wherein the level of hPygo2 gene expression is determined by the amount of hPygo2 protein as shown in SEQ ID NO: 2 and wherein the level of hPygo2 protein is determined using an antibody or a fragment thereof that binds specifically to hPygo2 protein.

9. The method according to claim 2 wherein the level of hPygo2 gene expression is determined by the amount of hPygo2 protein as shown in SEQ ID NO: 2.

10. The method according to claim 9 wherein the level of hPygo2 protein is determined using an antibody or a fragment thereof that binds specifically to hPygo2 protein.

11. The method according to claim 2 wherein the cancer is ovarian cancer, and the biological sample comprises epithelial ovarian cells.

12. The method according to claim 2 wherein the cancer is breast cancer, and the biological sample comprises mammary cells.

13. The method according to claim 2 wherein the cancer is cervical cancer, and the biological sample comprises cervical cells.

14. The method according to claim 13 wherein the level of hPygo2 gene expression is determined by the amount of hPygo2 protein as shown in SEQ ID NO: 2 and wherein the level of hPygo2 protein is determined using an antibody or a fragment thereof that binds specifically to hPygo2 protein.

15. The method according to claim 1 wherein the cancer is lung cancer, and the biological sample comprises lung cells.

16. The method according to claim 2 wherein the cancer is lung cancer, and the biological sample comprises lung cells.

17. The method according to claim 7 wherein the antibody or fragment thereof binds specifically to hPygo2 protein in the region set forth as amino acids 89-328 of SEQ ID NO: 2.

18. The method according to claim 8 wherein the antibody or fragment thereof binds specifically to hPygo2 protein in the region set forth as amino acids 89-328 of SEQ ID NO: 2.

19. The method according to claim 18 wherein the antibody or fragment thereof is a monoclonal antibody or fragment thereof.

20. The method according to claim 6 wherein the level of hPygo2 gene expression is determined by the amount of hPygo2 protein as shown in SEQ ID NO: 2 and wherein the level of hPygo2 protein is determined using a polyclonal antibody that binds specifically to hPygo2 protein in the region set forth as amino acids 89-328 of SEQ ID NO: 2.

* * * * *

UNITED STATES PATENT AND TRADEMARK OFFICE
CERTIFICATE OF CORRECTION

| | | |
|---|---|---|
| PATENT NO. | : 7,635,560 B2 | Page 1 of 1 |
| APPLICATION NO. | : 10/553661 | |
| DATED | : December 22, 2009 | |
| INVENTOR(S) | : Kenneth Kao et al. | |

It is certified that error appears in the above-identified patent and that said Letters Patent is hereby corrected as shown below:

Listed on the Title page, under Item (75) "Inventors":

-- Catherine Popadiuk, St. John's (CA) -- should be

-- Catherine Popadiuk, Burlington (CA) --

On the Title Page:

The first or sole Notice should read --

Subject to any disclaimer, the term of this patent is extended or adjusted under 35 U.S.C. 154(b) by 0 days.

Signed and Sealed this

Fifth Day of October, 2010

David J. Kappos
*Director of the United States Patent and Trademark Office*

SEQUENCE LISTING

```
<160> NUMBER OF SEQ ID NOS: 28

<210> SEQ ID NO 1
<211> LENGTH: 3190
<212> TYPE: DNA
<213> ORGANISM: homosapiens
<220> FEATURE:
<223> OTHER INFORMATION: hPygo-2
<220> FEATURE:
<221> NAME/KEY: CDS
<222> LOCATION: (173)..(1393)

<400> SEQUENCE: 1
gtctggagag agcgcgcagt ttgcgcggcg gctcggcgct tccctgtcgt cgcactttgt      60
ggttgctgca gctcgggggc ctgggctgcc cctgacaccc cttctgggcg atggtgcagc     120
ccaagggcgc ctccatcccc cgccgctgcc gctaacccgg gtcccccact cc atg gcc    178
                                                            Met Ala
                                                              1 gcc tcg gcg ccg ccc cca ccg gac aag ctg gag gga ggt ggc ggc ccc      226
Ala Ser Ala Pro Pro Pro Pro Asp Lys Leu Glu Gly Gly Gly Gly Pro
     5                  10                  15 gca ccg ccc cct gcg ccg ccc agc acc ggg agg aag cag ggc aag gcc      274
Ala Pro Pro Pro Ala Pro Pro Ser Thr Gly Arg Lys Gln Gly Lys Ala
 20                  25                  30 ggt ctg caa atg aag agt cca gaa aag aag cga agg aag tca aat act      322
Gly Leu Gln Met Lys Ser Pro Glu Lys Lys Arg Arg Lys Ser Asn Thr
35                  40                  45                  50 cag ggc cct gca tac tca cat ctg acg gag ttt gca cca ccc cca act      370
Gln Gly Pro Ala Tyr Ser His Leu Thr Glu Phe Ala Pro Pro Pro Thr
                 55                  60                  65 ccc atg gtg gat cac ctg gtt gca tcc aac cct ttt gaa gat gac ttc      418
Pro Met Val Asp His Leu Val Ala Ser Asn Pro Phe Glu Asp Asp Phe
             70                  75                  80 gga gcc ccc aaa gtg ggg gtt gca gcc cct cca ttc ctt ggc agt cct      466
Gly Ala Pro Lys Val Gly Val Ala Ala Pro Pro Phe Leu Gly Ser Pro
         85                  90                  95 gtg ccc ttc gga ggc ttc cgt gtg cag ggg ggc atg gcg ggc cag gta      514
Val Pro Phe Gly Gly Phe Arg Val Gln Gly Gly Met Ala Gly Gln Val
    100                 105                 110
```

```
ccc cca ggc tac agc act gga ggt gga ggg ggc ccc cag cca ctc cgt        562
Pro Pro Gly Tyr Ser Thr Gly Gly Gly Gly Gly Pro Gln Pro Leu Arg
115                 120                 125                 130 cga cag cca ccc ccc ttc cct ccc aat cct atg ggc cct gct ttc aac        610
Arg Gln Pro Pro Pro Phe Pro Pro Asn Pro Met Gly Pro Ala Phe Asn
                135                 140                 145 atg ccc ccc cag ggt cct ggc tac cca ccc cca ggc aac atg aac ttt        658
Met Pro Pro Gln Gly Pro Gly Tyr Pro Pro Pro Gly Asn Met Asn Phe
                150                 155                 160 ccc agc caa ccc ttc aac cag cct ctg ggt caa aac ttt agt cct ccc        706
Pro Ser Gln Pro Phe Asn Gln Pro Leu Gly Gln Asn Phe Ser Pro Pro
                165                 170                 175 agt ggg cag atg atg ccg ggc cca gtg ggg gga ttt ggt ccc atg atc        754
Ser Gly Gln Met Met Pro Gly Pro Val Gly Gly Phe Gly Pro Met Ile
        180                 185                 190 tca ccc acc atg gga cag cct ccc aga gca gag ctg ggc cca cct tct        802
Ser Pro Thr Met Gly Gln Pro Pro Arg Ala Glu Leu Gly Pro Pro Ser
195                 200                 205                 210 ctg tcc caa cga ttt gct cag cca ggg gct cct ttt ggc cct tct cct        850
Leu Ser Gln Arg Phe Ala Gln Pro Gly Ala Pro Phe Gly Pro Ser Pro
                215                 220                 225 ctc cag aga cct ggt cag ggg ctc ccc agc ctg ccg cct aac aca agt        898
Leu Gln Arg Pro Gly Gln Gly Leu Pro Ser Leu Pro Pro Asn Thr Ser
                230                 235                 240 ccc ttt cct ggt ccg gac cct ggc ttt cct ggc cct ggt ggt gag gat        946
Pro Phe Pro Gly Pro Asp Pro Gly Phe Pro Gly Pro Gly Gly Glu Asp
                245                 250                 255 ggg ggg aag ccc ttg aat cca cct gct tct act gct ttt ccc cag gag        994
Gly Gly Lys Pro Leu Asn Pro Pro Ala Ser Thr Ala Phe Pro Gln Glu
        260                 265                 270 ccc cac tca ggc tcc ccg gct gct gct gtt aat ggg aac cag ccc agt       1042
Pro His Ser Gly Ser Pro Ala Ala Ala Val Asn Gly Asn Gln Pro Ser
275                 280                 285                 290 ttc ccc ccg aac agc agt ggg cgg ggt ggg ggc act cca gat gcc aac       1090
Phe Pro Pro Asn Ser Ser Gly Arg Gly Gly Gly Thr Pro Asp Ala Asn
                295                 300                 305 agc ttg gca ccc cct ggc aag gca ggt ggg ggc tcc ggg ccc cag cct       1138
Ser Leu Ala Pro Pro Gly Lys Ala Gly Gly Gly Ser Gly Pro Gln Pro
                310                 315                 320 ccc cca ggc ttg gtg tac cca tgt ggt gcc tgt cgg agt gag gtg aac       1186
Pro Pro Gly Leu Val Tyr Pro Cys Gly Ala Cys Arg Ser Glu Val Asn
                325                 330                 335 gat gac cag gat gcc att ctg tgt gag gcc tcc tgc cag aaa tgg ttc       1234
Asp Asp Gln Asp Ala Ile Leu Cys Glu Ala Ser Cys Gln Lys Trp Phe
340                 345                 350 cac cgt gag tgc aca ggc atg act gag agc gcc tat ggg ctg ctg acc       1282
His Arg Glu Cys Thr Gly Met Thr Glu Ser Ala Tyr Gly Leu Leu Thr
355                 360                 365                 370 act gaa gct tct gcc gtc tgg gcc tgc gat ctc tgc ctc aag acc aag       1330
Thr Glu Ala Ser Ala Val Trp Ala Cys Asp Leu Cys Leu Lys Thr Lys
                375                 380                 385 gag atc cag tct gtc tac atc cgt gag ggc atg ggg cag ctg gtg gct       1378
Glu Ile Gln Ser Val Tyr Ile Arg Glu Gly Met Gly Gln Leu Val Ala
                390                 395                 400 gct aac gat ggg tga cgctggtgaa gtggcccagg gaagtgcaca tgtctctccc       1433
Ala Asn Asp Gly
            405 tgctcttcca gggtgatttt tttgatgttt ggctcttggt ccttgtttcc actggctttc    1493 catccccatg gggcagaaac agtggctcct gggagcagaa aaggaattga ggtgggcagg    1553
```

-continued

```
cagaagagcc tggattgctc actgttttgg gaaacttaca tgttgagatc tacagagatc      1613
caggaaacca aagccctgct gagcagagcc attttgtggc tatttctgga ggcccaggag      1673
tgtggctgca agagaaaagg ggctggagga agatccggag ggcagggggtg ttccctctgc     1733 tgatgatgga tgcccctaac acctgtgcct aacacccta ctgaaccca cagctccagc       1793 cttagttttt ggagtcaagt gttaaaggtt tctggccaga ggaattgggg tcttgccatc     1853
cctgcaatag ccctttatg ggctctggga acagctta gggaataaat ggggattttc       1913 cccttttct acccactcct tgcttcctc aagacttac ccaactcctt ccccctcaga       1973
gaaccaaata gcctgaggaa gcaggagagt tcctggttat ggcagtttct tggtgatttg    2033
gggcttcaag acagtaggtg agagatgctg tcaggacgta tcttcttcat accaaagtca    2093
ctggtccttt ctcagcctct ctcgtgcttt tctcctaatg accatatttt tgccaaaaat    2153
tgggatatgt tatctgacag accagaatat ttgaagtttg ggctgtcctg aaagtctgga    2213
ctttggtggt accctcctcc cccagcccat ctgttgcaca ttatactccg tgtgttcttc    2273
aactttcggc gcccttattc ccctgccttc ctggcttgat tgaaggaaag cttgaaaagg    2333
cgcagagccc tatacctcat ttcctccatg ataaaaggat ccaagtgagg ccctgtcaca    2393
gcctgtgggt aggggatgcg gcgggatcct cattgccatg gtactcaaag gtagaagagc    2453
ctggagtttg ttgcttctct ttgctattct ttcatatcct cttgggcctg gtgattaatt    2513
agcaattctc attcctctca gccaaaggcc tgcactgggc tttatttgtc tttttttatt    2573
ttttaagcac tgcctgccag agatgggcct ggggcctgat gaggaccta gcgctgctcg    2633 ttctcctttt ctgttcatgc acacattcct ccatggggtg gggaaggcag gcatggggtg    2693
tggccctcgg agaagttagg agtccccag ctcaagatac agtggcaaag acctagtggt     2753
cccctacccc cacttctctc agttcctggc atgaggagag aagaccctgc tctggtggag    2813
ctgacaacct tgaggctgg gaggagagca gcctctgggc atcgttccca gtgtccctca     2873
cactaaaacg gcgtagatgg caaccccca ccccacccc gctgctcaac tcttgtgttt     2933
gttgttctgt ttgcccccatt tatctgttgc tgttttttgtg ttgtcttccc ctgctccgca  2993
ttttgtaaaa tggcccctgg gggagtgttt ttgctggatc tgctccctct cgctctctca    3053
ctccactact ttttggacaa agtgatggca gaatgcggtg gtggtgggg tcttttgtac     3113 tgttggatta ataaaatgat tttaaaatcc caaaaaaaa aaaaaaaaa aaaaaaaaa       3173 aaaaaaaaaa aaaaaaa                                                    3190
```

```
<210> SEQ ID NO 2
<211> LENGTH: 406
<212> TYPE: PRT
<213> ORGANISM: homosapiens
<220> FEATURE:
<223> OTHER INFORMATION: hPygo-2

<400> SEQUENCE: 2

Met Ala Ala Ser Ala Pro Pro Pro Asp Lys Leu Glu Gly Gly Gly
1               5                   10                  15

Gly Pro Ala Pro Pro Ala Pro Pro Ser Thr Gly Arg Lys Gln Gly
            20                  25                  30

Lys Ala Gly Leu Gln Met Lys Ser Pro Glu Lys Lys Arg Arg Lys Ser
        35                  40                  45

Asn Thr Gln Gly Pro Ala Tyr Ser His Leu Thr Glu Phe Ala Pro Pro
    50                  55                  60
```

```
Pro Thr Pro Met Val Asp His Leu Val Ala Ser Asn Pro Phe Glu Asp
 65                  70                  75                  80

Asp Phe Gly Ala Pro Lys Val Gly Val Ala Ala Pro Pro Phe Leu Gly
                 85                  90                  95

Ser Pro Val Pro Phe Gly Gly Phe Arg Val Gln Gly Gly Met Ala Gly
            100                 105                 110

Gln Val Pro Pro Gly Tyr Ser Thr Gly Gly Gly Gly Pro Gln Pro
        115                 120                 125

Leu Arg Arg Gln Pro Pro Phe Pro Pro Asn Pro Met Gly Pro Ala
    130                 135                 140

Phe Asn Met Pro Pro Gln Gly Pro Gly Tyr Pro Pro Gly Asn Met
145                 150                 155                 160

Asn Phe Pro Ser Gln Pro Phe Asn Gln Pro Leu Gly Gln Asn Phe Ser
                165                 170                 175

Pro Pro Ser Gly Gln Met Met Pro Gly Pro Val Gly Phe Gly Pro
            180                 185                 190

Met Ile Ser Pro Thr Met Gly Gln Pro Pro Arg Ala Glu Leu Gly Pro
        195                 200                 205

Pro Ser Leu Ser Gln Arg Phe Ala Gln Pro Gly Ala Pro Phe Gly Pro
    210                 215                 220

Ser Pro Leu Gln Arg Pro Gly Gln Gly Leu Pro Ser Leu Pro Pro Asn
225                 230                 235                 240

Thr Ser Pro Phe Pro Gly Pro Asp Pro Gly Phe Pro Gly Pro Gly Gly
                245                 250                 255

Glu Asp Gly Gly Lys Pro Leu Asn Pro Pro Ala Ser Thr Ala Phe Pro
            260                 265                 270

Gln Glu Pro His Ser Gly Ser Pro Ala Ala Ala Val Asn Gly Asn Gln
        275                 280                 285

Pro Ser Phe Pro Pro Asn Ser Ser Gly Arg Gly Gly Gly Thr Pro Asp
    290                 295                 300

Ala Asn Ser Leu Ala Pro Pro Gly Lys Ala Gly Gly Ser Gly Pro
305                 310                 315                 320

Gln Pro Pro Pro Gly Leu Val Tyr Pro Cys Gly Ala Cys Arg Ser Glu
                325                 330                 335

Val Asn Asp Asp Gln Asp Ala Ile Leu Cys Glu Ala Ser Cys Gln Lys
            340                 345                 350

Trp Phe His Arg Glu Cys Thr Gly Met Thr Glu Ser Ala Tyr Gly Leu
        355                 360                 365

Leu Thr Thr Glu Ala Ser Ala Val Trp Ala Cys Asp Leu Cys Leu Lys
    370                 375                 380

Thr Lys Glu Ile Gln Ser Val Tyr Ile Arg Glu Gly Met Gly Gln Leu
385                 390                 395                 400

Val Ala Ala Asn Asp Gly
                405
```

<210> SEQ ID NO 3
<211> LENGTH: 1260
<212> TYPE: DNA
<213> ORGANISM: homosapiens
<220> FEATURE:
<221> NAME/KEY: CDS
<222> LOCATION: (1)..(1260)
<220> FEATURE:
<223> OTHER INFORMATION: hPygo-1

<400> SEQUENCE: 3

-continued

```
atg ccc gcc gag aac tct cca gct ccc gct tac aaa gtt tcc tcg cat      48
Met Pro Ala Glu Asn Ser Pro Ala Pro Ala Tyr Lys Val Ser Ser His
 1               5                  10                  15 ggt ggt gat agt gga ctg gat ggg tta gga gga cca ggt gta caa cta      96
Gly Gly Asp Ser Gly Leu Asp Gly Leu Gly Gly Pro Gly Val Gln Leu
             20                  25                  30 gga agc cca gat aag aaa aag cgc aag gca aat aca cag gga cct tct     144
Gly Ser Pro Asp Lys Lys Lys Arg Lys Ala Asn Thr Gln Gly Pro Ser
         35                  40                  45 ttc cct cca ttg tct gag tat gct cca cca ccg aat cca aac tct gac     192
Phe Pro Pro Leu Ser Glu Tyr Ala Pro Pro Pro Asn Pro Asn Ser Asp
 50                  55                  60 cat cta gtg gct gct aat cca ttt gat gac aac tat aat act att tcc     240
His Leu Val Ala Ala Asn Pro Phe Asp Asp Asn Tyr Asn Thr Ile Ser
 65                  70                  75                  80 tat aaa cca cta cct tcg tca aat cca tat ctt ggc cct ggt tat cct     288
Tyr Lys Pro Leu Pro Ser Ser Asn Pro Tyr Leu Gly Pro Gly Tyr Pro
                 85                  90                  95 ggc ttt gga ggc tat agt aca ttc aga atg cca cct cac gtt ccc cca     336
Gly Phe Gly Gly Tyr Ser Thr Phe Arg Met Pro Pro His Val Pro Pro
            100                 105                 110 aga atg tct tcc cca tac tgt ggt cct tac tca ctc agg aac cag cca     384
Arg Met Ser Ser Pro Tyr Cys Gly Pro Tyr Ser Leu Arg Asn Gln Pro
        115                 120                 125 cac cca ttt cct cag aat cct ctg ggc atg ggt ttt aat cga cct cat     432
His Pro Phe Pro Gln Asn Pro Leu Gly Met Gly Phe Asn Arg Pro His
    130                 135                 140 gct ttt aac ttt ggg cca cat gat aat tca agt ttc ggt aat cca tct     480
Ala Phe Asn Phe Gly Pro His Asp Asn Ser Ser Phe Gly Asn Pro Ser
145                 150                 155                 160 tat aat aat gca cta agt cag aat gtc aac atg cct aat caa cat ttt     528
Tyr Asn Asn Ala Leu Ser Gln Asn Val Asn Met Pro Asn Gln His Phe
                165                 170                 175 aga caa aat cct gct gaa aat ttc agt caa att cct cca cag aat gct     576
Arg Gln Asn Pro Ala Glu Asn Phe Ser Gln Ile Pro Pro Gln Asn Ala
            180                 185                 190 agc caa gtt tct aac ccc gat ttg gca tct aat ttt gtt cct gga aat     624
Ser Gln Val Ser Asn Pro Asp Leu Ala Ser Asn Phe Val Pro Gly Asn
        195                 200                 205 aat tca aat ttt act tct ccg tta gaa tct aat cat tct ttt att cct     672
Asn Ser Asn Phe Thr Ser Pro Leu Glu Ser Asn His Ser Phe Ile Pro
    210                 215                 220 ccc cca aac act ttt ggt caa gca aaa gca cca ccc cca aaa caa gac     720
Pro Pro Asn Thr Phe Gly Gln Ala Lys Ala Pro Pro Pro Lys Gln Asp
225                 230                 235                 240 ttt act caa gga gca acc aaa aac act aat caa aat tcc tct gct cat     768
Phe Thr Gln Gly Ala Thr Lys Asn Thr Asn Gln Asn Ser Ser Ala His
                245                 250                 255 cca cct cac ttg aat atg gat gac aca gtg aat cag agt aat att gaa     816
Pro Pro His Leu Asn Met Asp Asp Thr Val Asn Gln Ser Asn Ile Glu
            260                 265                 270 tta aaa aat gtt aat cga aac aat gca gta aat cag gag aac agc cgt     864
Leu Lys Asn Val Asn Arg Asn Asn Ala Val Asn Gln Glu Asn Ser Arg
        275                 280                 285 tca agt agc act gaa gcc aca aac aat aac cct gca aat ggg acg cag     912
Ser Ser Ser Thr Glu Ala Thr Asn Asn Asn Pro Ala Asn Gly Thr Gln
    290                 295                 300 aat aag cca cga caa cca aga ggt gca gca gat gcc tgc acc aca gaa     960
Asn Lys Pro Arg Gln Pro Arg Gly Ala Ala Asp Ala Cys Thr Thr Glu
305                 310                 315                 320
```

```
aaa agc aat aaa tcc tct ctt cac cca aac cgt cat ggc cat tcg tct    1008
Lys Ser Asn Lys Ser Ser Leu His Pro Asn Arg His Gly His Ser Ser
            325                 330                 335 tct gac cca gtg tat cct tgt gga att tgt aca aac gag gtg aac gat    1056
Ser Asp Pro Val Tyr Pro Cys Gly Ile Cys Thr Asn Glu Val Asn Asp
        340                 345                 350 gat cag gat gcc atc tta tgt gag gcc tct tgt cag aaa tgg ttt cat    1104
Asp Gln Asp Ala Ile Leu Cys Glu Ala Ser Cys Gln Lys Trp Phe His
        355                 360                 365 cgg atc tgt act gga atg act gaa aca gct tat ggc ctc tta act gca    1152
Arg Ile Cys Thr Gly Met Thr Glu Thr Ala Tyr Gly Leu Leu Thr Ala
    370                 375                 380 gaa gca tct gca gta tgg ggc tgt gat acc tgt atg gct gac aaa gat    1200
Glu Ala Ser Ala Val Trp Gly Cys Asp Thr Cys Met Ala Asp Lys Asp
385                 390                 395                 400 gtc cag tta atg cgt act aga gaa act ttt ggt cca tct gca gtg ggc    1248
Val Gln Leu Met Arg Thr Arg Glu Thr Phe Gly Pro Ser Ala Val Gly
                405                 410                 415 agt gat gct taa                                                    1260
Ser Asp Ala <210> SEQ ID NO 4
<211> LENGTH: 419
<212> TYPE: PRT
<213> ORGANISM: homosapiens
<220> FEATURE:
<223> OTHER INFORMATION: hPygo-1

<400> SEQUENCE: 4

Met Pro Ala Glu Asn Ser Pro Ala Pro Ala Tyr Lys Val Ser Ser His
1               5                   10                  15

Gly Gly Asp Ser Gly Leu Asp Gly Leu Gly Gly Pro Gly Val Gln Leu
            20                  25                  30

Gly Ser Pro Asp Lys Lys Lys Arg Lys Ala Asn Thr Gln Gly Pro Ser
        35                  40                  45

Phe Pro Pro Leu Ser Glu Tyr Ala Pro Pro Asn Pro Asn Ser Asp
    50                  55                  60

His Leu Val Ala Ala Asn Pro Phe Asp Asp Asn Tyr Asn Thr Ile Ser
65                  70                  75                  80

Tyr Lys Pro Leu Pro Ser Ser Asn Pro Tyr Leu Gly Pro Gly Tyr Pro
                85                  90                  95

Gly Phe Gly Gly Tyr Ser Thr Phe Arg Met Pro His Val Pro Pro
            100                 105                 110

Arg Met Ser Ser Pro Tyr Cys Gly Pro Tyr Ser Leu Arg Asn Gln Pro
        115                 120                 125

His Pro Phe Pro Gln Asn Pro Leu Gly Met Gly Phe Asn Arg Pro His
    130                 135                 140

Ala Phe Asn Phe Gly Pro His Asp Asn Ser Ser Phe Gly Asn Pro Ser
145                 150                 155                 160

Tyr Asn Asn Ala Leu Ser Gln Asn Val Asn Met Pro Asn Gln His Phe
                165                 170                 175

Arg Gln Asn Pro Ala Glu Asn Phe Ser Gln Ile Pro Pro Gln Asn Ala
            180                 185                 190

Ser Gln Val Ser Asn Pro Asp Leu Ala Ser Asn Phe Val Pro Gly Asn
        195                 200                 205

Asn Ser Asn Phe Thr Ser Pro Leu Glu Ser Asn His Ser Phe Ile Pro
    210                 215                 220
```

```
Pro Pro Asn Thr Phe Gly Gln Ala Lys Ala Pro Pro Lys Gln Asp
225                 230                 235                 240

Phe Thr Gln Gly Ala Thr Lys Asn Thr Asn Gln Asn Ser Ser Ala His
                245                 250                 255

Pro Pro His Leu Asn Met Asp Asp Thr Val Asn Gln Ser Asn Ile Glu
                260                 265                 270

Leu Lys Asn Val Asn Arg Asn Asn Ala Val Asn Gln Glu Asn Ser Arg
                275                 280                 285

Ser Ser Ser Thr Glu Ala Thr Asn Asn Pro Ala Asn Gly Thr Gln
            290                 295                 300

Asn Lys Pro Arg Gln Pro Arg Gly Ala Ala Asp Ala Cys Thr Thr Glu
305                 310                 315                 320

Lys Ser Asn Lys Ser Ser Leu His Pro Asn Arg His Gly His Ser Ser
                325                 330                 335

Ser Asp Pro Val Tyr Pro Cys Gly Ile Cys Thr Asn Glu Val Asn Asp
                340                 345                 350

Asp Gln Asp Ala Ile Leu Cys Glu Ala Ser Cys Gln Lys Trp Phe His
                355                 360                 365

Arg Ile Cys Thr Gly Met Thr Glu Thr Ala Tyr Gly Leu Leu Thr Ala
370                 375                 380

Glu Ala Ser Ala Val Trp Gly Cys Asp Thr Cys Met Ala Asp Lys Asp
385                 390                 395                 400

Val Gln Leu Met Arg Thr Arg Glu Thr Phe Gly Pro Ser Ala Val Gly
                405                 410                 415

Ser Asp Ala

<210> SEQ ID NO 5
<211> LENGTH: 20
<212> TYPE: DNA
<213> ORGANISM: artificial
<220> FEATURE:
<223> OTHER INFORMATION: Hpy1 antisense ON

<400> SEQUENCE: 5
gagctgcagc aaccacaaag                                              20

<210> SEQ ID NO 6
<211> LENGTH: 21
<212> TYPE: DNA
<213> ORGANISM: artificial
<220> FEATURE:
<223> OTHER INFORMATION: Hpy2 antisense ON

<400> SEQUENCE: 6
ggacccgggt tagcggcagc g                                            21

<210> SEQ ID NO 7
<211> LENGTH: 21
<212> TYPE: DNA
<213> ORGANISM: artificial
<220> FEATURE:
<223> OTHER INFORMATION: Hpy3 antisense ON

<400> SEQUENCE: 7
ccacctccct ccagcttgtc c                                            21

<210> SEQ ID NO 8
<211> LENGTH: 19
<212> TYPE: DNA
```

```
<213> ORGANISM: artificial
<220> FEATURE:
<223> OTHER INFORMATION: Hpy4 antisense ON

<400> SEQUENCE: 8
ggaggactaa agttttgac                                                19

<210> SEQ ID NO 9
<211> LENGTH: 19
<212> TYPE: DNA
<213> ORGANISM: artificial
<220> FEATURE:
<223> OTHER INFORMATION: Hpy5 antisense ON

<400> SEQUENCE: 9
ggctgagcaa atcgttggg                                                19

<210> SEQ ID NO 10
<211> LENGTH: 20
<212> TYPE: DNA
<213> ORGANISM: artificial
<220> FEATURE:
<223> OTHER INFORMATION: Hpy6 antisense ON

<400> SEQUENCE: 10
gaaaagcagt agaagcaggt                                               20

<210> SEQ ID NO 11
<211> LENGTH: 18
<212> TYPE: DNA
<213> ORGANISM: artificial
<220> FEATURE:
<223> OTHER INFORMATION: Hpy7 antisense ON

<400> SEQUENCE: 11
ctcacggatg tagacaga                                                 18

<210> SEQ ID NO 12
<211> LENGTH: 19
<212> TYPE: DNA
<213> ORGANISM: artificial
<220> FEATURE:
<223> OTHER INFORMATION: Hpy8 antisense ON

<400> SEQUENCE: 12
cctctggcca gaaaccttt                                                19

<210> SEQ ID NO 13
<211> LENGTH: 19
<212> TYPE: DNA
<213> ORGANISM: artificial
<220> FEATURE:
<223> OTHER INFORMATION: Hpy9 antisense ON

<400> SEQUENCE: 13
ctcttctacc tttgagtac                                                19

<210> SEQ ID NO 14
<211> LENGTH: 18
<212> TYPE: DNA
<213> ORGANISM: artificial
<220> FEATURE:
<223> OTHER INFORMATION: Hpy10 antisense ON

<400> SEQUENCE: 14
cactgtatct tgagctgg                                                 18
```

```
<210> SEQ ID NO 15
<211> LENGTH: 19
<212> TYPE: RNA
<213> ORGANISM: artificial
<220> FEATURE:
<223> OTHER INFORMATION: Hpy2A siRNA

<400> SEQUENCE: 15
cgaugaccag gaugccauu                                                        19

<210> SEQ ID NO 16
<211> LENGTH: 19
<212> TYPE: RNA
<213> ORGANISM: artificial
<220> FEATURE:
<223> OTHER INFORMATION: Hpy2B siRNA

<400> SEQUENCE: 16
agaagcgaag gaagucaaa                                                        19

<210> SEQ ID NO 17
<211> LENGTH: 19
<212> TYPE: RNA
<213> ORGANISM: artificial
<220> FEATURE:
<223> OTHER INFORMATION: Hpy2C siRNA

<400> SEQUENCE: 17
ugggaaccag cccaguuuc                                                        19

<210> SEQ ID NO 18
<211> LENGTH: 19
<212> TYPE: RNA
<213> ORGANISM: artificial
<220> FEATURE:
<223> OTHER INFORMATION: Hpy2D siRNA

<400> SEQUENCE: 18
ccagccucug ggucaaaac                                                        19

<210> SEQ ID NO 19
<211> LENGTH: 19
<212> TYPE: RNA
<213> ORGANISM: artificial
<220> FEATURE:
<223> OTHER INFORMATION: Hpy2E siRNA

<400> SEQUENCE: 19
cuuucccagc caacccuuc                                                        19

<210> SEQ ID NO 20
<211> LENGTH: 19
<212> TYPE: DNA
<213> ORGANISM: artificial
<220> FEATURE:
<223> OTHER INFORMATION: mismatched sequence to Hpy5

<400> SEQUENCE: 20
gcctgagcta atcattggt                                                        19

<210> SEQ ID NO 21
<211> LENGTH: 18
<212> TYPE: DNA
<213> ORGANISM: artificial
<220> FEATURE:
```

-continued

<223> OTHER INFORMATION: anti-Xenopus pygo2

<400> SEQUENCE: 21
tttgcgccgt tcttctc                                                          18

<210> SEQ ID NO 22
<211> LENGTH: 24
<212> TYPE: DNA
<213> ORGANISM: artificial
<220> FEATURE:
<223> OTHER INFORMATION: Forward hPygo2 primer

<400> SEQUENCE: 22
gcatccaacc cttttgaaga tgac                                                  24

<210> SEQ ID NO 23
<211> LENGTH: 25
<212> TYPE: DNA
<213> ORGANISM: artificial
<220> FEATURE:
<223> OTHER INFORMATION: Reverse hPygo2 primer

<400> SEQUENCE: 23
tcagccaggg ggtgccaagc tgttg                                                 25

<210> SEQ ID NO 24
<211> LENGTH: 20
<212> TYPE: DNA
<213> ORGANISM: artificial
<220> FEATURE:
<223> OTHER INFORMATION: Forward hPygo1 primer

<400> SEQUENCE: 24
gccacgacaa ccaagaggtg                                                       20

<210> SEQ ID NO 25
<211> LENGTH: 22
<212> TYPE: DNA
<213> ORGANISM: artificial
<220> FEATURE:
<223> OTHER INFORMATION: Reverse hPygo1 primer

<400> SEQUENCE: 25
ccagtacaga tccgatgaaa cc                                                    22

<210> SEQ ID NO 26
<211> LENGTH: 20
<212> TYPE: DNA
<213> ORGANISM: artificial
<220> FEATURE:
<223> OTHER INFORMATION: Forward Bcl-9 primer

<400> SEQUENCE: 26
gatgttgtcc tggtgtcttg                                                       20

<210> SEQ ID NO 27
<211> LENGTH: 21
<212> TYPE: DNA
<213> ORGANISM: artificial
<220> FEATURE:
<223> OTHER INFORMATION: Reverse Bcl-9 primer

<400> SEQUENCE: 27
ggtcacgaca ctgcagtgct c                                                     21

```
<210> SEQ ID NO 28
<211> LENGTH: 19
<212> TYPE: DNA
<213> ORGANISM: artificial
<220> FEATURE:
<223> OTHER INFORMATION: mismatched sequence to Hpy5

<400> SEQUENCE: 28
gtctgagcta atcattggt                                              19
```